United States Patent
Belousov et al.

(10) Patent No.: US 7,348,146 B2
(45) Date of Patent: Mar. 25, 2008

(54) SINGLE NUCLEOTIDE POLYMORPHISM ANALYSIS OF HIGHLY POLYMORPHIC TARGET SEQUENCES

(75) Inventors: Yevgeniy Belousov, Mill Creek, CA (US); Robert O. Dempcy, Kirkland, WA (US); Sergey G. Lokhov, Kirkland, WA (US); Alexei Vorobiev, Redmond, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 378 days.

(21) Appl. No.: 10/954,955

(22) Filed: Sep. 29, 2004

(65) Prior Publication Data

US 2005/0118623 A1    Jun. 2, 2005

Related U.S. Application Data

(60) Provisional application No. 60/508,792, filed on Oct. 2, 2003.

(51) Int. Cl.
*C12Q 1/68* (2006.01)
*C12P 19/34* (2006.01)
*C07H 21/00* (2006.01)
*C07H 21/02* (2006.01)

(52) U.S. Cl. ................ 435/6; 435/91.1; 536/23.1; 536/24.3; 536/24.33

(58) Field of Classification Search ............ 435/6, 435/91.1; 536/23.1, 24.3, 24.33
See application file for complete search history.

(56) References Cited

U.S. PATENT DOCUMENTS

| | | |
|---|---|---|
| 4,358,535 A | 11/1982 | Palkow et al. |
| 4,458,066 A | 7/1984 | Caruthers |
| 4,683,195 A | 7/1987 | Mullis et al. |
| 4,683,202 A | 7/1987 | Mullis |
| 4,800,159 A | 1/1989 | Mullis et al. |
| 4,835,263 A | 5/1989 | Nguyen et al. |
| 4,868,103 A | 9/1989 | Stavrianopoulos et al. |
| 4,868,105 A | 9/1989 | Urdea et al. |
| 4,883,750 A | 11/1989 | Whiteley et al. |
| 5,124,246 A | 6/1992 | Urdea et al. |
| 5,210,015 A | 5/1993 | Gelfand et al. |
| 5,237,101 A | 8/1993 | Nicolaou et al. |
| 5,419,966 A | 5/1995 | Reed et al. |
| 5,446,137 A | 8/1995 | Maag et al. |
| 5,449,767 A | 9/1995 | Ward et al. |
| 5,492,806 A | 2/1996 | Drmanac et al. |
| 5,512,667 A | 4/1996 | Reed et al. |
| 5,525,464 A | 6/1996 | Drmanac et al. |
| 5,556,752 A | 9/1996 | Lockhart et al. |
| 5,574,142 A | 11/1996 | Meyer, Jr. et al. |
| 5,646,126 A | 7/1997 | Cheng et al. |
| 5,659,022 A | 8/1997 | Kutyavin et al. |
| 5,776,907 A | 7/1998 | Kohn et al. |
| 5,786,138 A | 7/1998 | Swenson |
| 5,801,155 A | 9/1998 | Kutyavin et al. |
| 6,248,518 B1 | 6/2001 | Parkhurst et al. |
| 6,312,894 B1 | 11/2001 | Hedgpeth et al. |
| 6,448,015 B2 | 9/2002 | Parkhurst et al. |
| 6,492,346 B1 | 12/2002 | Hedgpeth et al. |
| 2003/0175728 A1 | 9/2003 | Belousov et al. |

FOREIGN PATENT DOCUMENTS

| | | |
|---|---|---|
| EP | 0 320 308 B1 | 11/1993 |
| EP | 0 336 731 B1 | 5/1994 |
| EP | 0 672 677 A2 | 3/1995 |
| WO | WO 90/03370 | 4/1990 |
| WO | WO 90/14353 | 11/1990 |
| WO | WO 92/00588 | 6/1992 |
| WO | WO 92/20698 | 11/1992 |
| WO | WO 93/03736 | 3/1993 |
| WO | WO 94/17092 | 8/1994 |
| WO | WO 95/29184 | 11/1995 |
| WO | WO 96/17957 | 6/1996 |
| WO | WO 96/32496 | 10/1996 |
| WO | WO 96/40711 | 12/1996 |
| WO | WO 97/12896 | 4/1997 |
| WO | WO 98/02448 | 1/1998 |

OTHER PUBLICATIONS

Alfonina et al., "Efficient priming of PCR with short oligonucleotides conjugated to a minor groove binder." Nucleic Acids Res. 25(13):2657-2660 (1997).

Afonina, et al., "Sequence-specific arrest of primer extension on single-stranded DNA by an oligonucleotide-minor groove binder conjugate." Proc. Natl. Acad. Sci. USA, 93:3199-3204 (1996).

Agrawal, et al., "Pharmacokinetics, biodistribution, and stability of oligodeoxynucleotide phosphorothioates in mice." Proc. Natl. Acad. Sci. USA, RR:7595-7599 (1991).

Animati, et al., "Synthesis of two distamycin analogues and their binding mode to d(CGCAAATTTGCG)2 in the 2:1 solution complexes as determined by two dimensional H-NMR." J. Med. Chem., 38:1140-1149 (1995).

Asseline, et al., "Nucleic acid-binding molecules with high affinity and base sequence specificity: Interacting agents covalently linked to oligodeoxynucleotides." Proc. Natl. Acad. Sci. USA, 81: 3297-3301 (1994).

(Continued)

*Primary Examiner*—Jezia Riley
(74) *Attorney, Agent, or Firm*—Townsend and Townsend & Crew LLP

(57) ABSTRACT

Methods and probes are provided for the analysis of target sequences having two or more polymorphisms wherein one of the polymorphisms is to be distinguished and another polymorphism is to be masked.

14 Claims, 10 Drawing Sheets

OTHER PUBLICATIONS

Atkinson, T., and Smith M., "Solid-phase synthesis of oligodeoxyribonucleotides by the phosphite-triester method." in: *Oligonucleotide Synthesis, A Practical Approach*, M.J. Gait (ed.), IRL Press, Oxford, UK, pp. 35-81 (1984).

Bailly, et al., "DNA Recognition by Intercalator-minor-groove binder hybrid molecules." Bioconjugate Chem. 2(6):379-393 (1991).

Bailly et al., "DNA-binding properties of a distamycin-ellipticine hybrid molecule." Mol. Pharmacol., 41:845-55 (1992).

Bailly et al., "The different binding modes of Hoechst 33258 to DNA studied by electric linear dichroism." Nucl. Acid Res., 21(6):3705-9 (1993).

Boger, et al., "CC-1065 and the duocarmycins: Unraveling the keys to a new class of naturally derived DNA alkylatine agents." Proc. Natl. Acad. Sci. USA, 92:3642-3649 (1995).

Boger, et al., "CC-1065 partial structures: enhancement of noncovalent affinity for DNA minor groove binding through introduction of stabilizing electrostatic interactions." J. Org. Chem., 57:1277-1284 (1992).

Boger et al., "Studies on the total synthesis of CC-1065: preparation of a synthetic, simplified 3-carbamoyl-1,2-dihydro-3H-pyrrolo[3,2-e]indole dimer/trimer/tetramer (CDPI dimer/trimer/tetramer) and development of methodology for DEP-I dimmer methyl ester Formation." J. Org. Chem., 52:1521-1530 (1987).

Bolli, et al., "Watson-Crick base-pairing properties of bicyclo-DNA." Nucleic Acids Res., 24:4660-4667 (1996).

Bruice, et al., "Rational design of substituted tripyrrole peptides that complex with DNA by both selective minor groove binding and electrostatic interaction with the phosphate backbone." Proc. Natl., Acad. Sci. USA, 89:1700-4 (1992).

Caetano-Anolles, et al., "DNA amplification fingerprinting using very short arbitrary oligonucleotide primers." Biotechnology, 9:553-557 (1991).

Cardullo, et al., "Detection of nucleic acid hybridization by nonradiative fluorescence resonance energy transfer." Proc. Natl. Acad. Sci. USA, 85:8790-94 (1988).

Chen, et al., "A new DNA minor groove binding motif: cross-linked lexitropsins." J. Am Chem. Soc., 116:6995-7005 (1994).

Cosstick, et al., "Synthesis of d(GC) and d(CG) octamers containing alternating phosphorothioate linkages: Effect of the phosphorothioate group on the B-Z transiton." Biochemistry, 24:3630-38 (1985).

Demidov, et al., "Kinetics and mechanism of polyamide("peptide") nucleic acid binding to duplex DNA." Proc. Natl. Acad. Sci. USA, 92:2637-41 (1995).

Dempcy, et al., "Synthesis of a thymidyl pentamer of deoxyribonucleic guanidine and binding studies with DNA homopolynucleotides." Proc. Natl. Acad. Sci. USA, 92:6097-101 (1995).

Dervan, "Design of sequence-specific DNA-binding molecules." Science, 232:464-71 (1986).

Don et al., "'Touchdown 'PCR to circumvent spurious priming during gene amplification." Nucleic Acids Res., 19:4008 (1991).

Draper, et al., "A method for linking fluorescent labels to polynucleotides: Application to studies of ribosomes-ribonucleic acid interactions." Biochemistry, 19:1774-1781 (1980).

Eckstein, et al., "Polyribonucleotides containing phosphorothioate backbone." Eur. J. Biochem., 13:558-564 (1970).

Egholm, "Spectrometry senses more than a small difference." Nature Biotech., 15:1346 (1997).

Fagan et al., "Cooperative binding of distamycin-A to DNA in the 2:1 mode." J. Am Chem. Soc., 114:1080-1081 (1992).

Fodor et al., "Light-directed, spatially addressable parallel chemical synthesis." Science, 251:767-773 (1991).

Freiffelder, "Fluorescence Spectroscopy." Physical Biochemistry, Second Edition, W.H. Freeman & Co., San Francisco, pp. 537-542 (1982).

Gamper, et al., "Facile preparation of nuclease resistant 3' modified oligodeoxynucleotides." Nucleic Acids Res., 21(1):145-50 (1993).

Gibson, K.J. and Benkovic, S.J., "Synthesis and application of derivatizable oligonucleotides." Nucleic Acids Res., 15:6455-67 (1987).

Gibson, "A novel method for real time quantitative RT-PCR." Genome Res., 6:995-1001 (1996).

Giovannangeli, et al., "Oligonucleotide clamps arrest DNA synthesis on a single-stranded DNA target." Proc. Natl. Acad. Sci. USA, 90:10013-71 (1993).

Godovikova, et al., "Reactive oligonucleotide derivatives with a Zwitter-ionic terminal phosphate group for affinity reagents and probe construction." Bioorgan. Khim., 15:1246-1259 (1989).

Greenidge, et al., "DNA minor groove recognition properties of pentamidine and its analogs: a molecular modeling study." Molecular Pharmacology. 43(6):982-988 (1993).

Grehn, L., et al., "Novel efficient total synthesis of antiviral antibiotic distamycin-A." J. Org. Chem., 46:3492-3497 (1981).

Griffin, et al., "Genetic analysis by peptide nucleic acid affinity MALDI-TOF mass spectrometry." Nature Biotech., 15:1368-72 (1997).

Gryaznov, et al., "Modulation of oligonucleotide duplex and triplex stability via hydrophobic interactions.," Nucleic Acids Res., 21(25):5909-5915 (1993).

Gryanznov, et al., "Oligodeoxyribonucleotide N3'→ P' phosphoramidates: Synthesis and hybridization properties." J. Am Chem. Soc. 116:3143-3144 (1994).

Heid, et al., "Real Time Quantitative PCR." Genome Res., 6:986-994 (1996).

Holland, et al., "Detection of specific polymerase chain reaction product by utilizing the 5' → 3' exonuclease activity of *Thermus aquaticus* DNA polymerase." Proc. Natl. Acad. Sci. USA, 88:7276-80 (1991).

Huang, et al., "Diagnosis of glucose-6-phosphate dehydrogenase (G6PD) mutations by DNA amplification and allele-specific oligonucleotide probes." Acta Haematol., 88:92-95 (1992).

Hurley, et al., "Approaches toward the design of sequence-specific drugs for DNA." Ann. Rep. Med. Chem., 22(26):259-68 (1987).

Hurley et al., "Reaction of the antitumor antibiotic CC-1065 with DNA: Structure of DNA adduct with DNA sequence specificity." Science, 226(4676):843-844 (1984).

Inoue, et al., "Synthesis and hybridization studies in two complementary nona(2'-O-methyl)ribonucleotides." Nucleic Acids Res., 15(15):6131-6148 (1987).

Jones, "Preparation of protected deoxyribonucleotides." in: *Oligonucleotide Synthesis, A Practical Approach*, M.J. Gait (ed.), IRL Press, Oxford, UK, pp. 23-34 (1984).

Jost, et al., "Quantitative precipitation of short oligonucleotides with low concentrations of cetyltrimethylammonium bromide." Nucleic Acids Res., 17(5):2143 (1989).

Kazimierczuk, et al., "Synthesis of 2'-deoxytubercidin, 2'-deoxyadenosine, and related 2-deoxynucleosides via a novel direct stereospecific sodium salt glycosylation procedure." J. Am Chem. Soc., 106:6379-6382 (1984).

Kenten, et al., "Rapid electrochemiluminescence assays of polymerase chain reaction products." Clin. Chem., 37(9):1626-32 (1991).

Kessler, (ed.), *Nonradioactive Labeling and Detection of Biomolecules*, Springer-Verlag, Berlin, pp. 13-14 (1992).

Kim, et al., "Helix-stabilizing agent, CC-1065, enhances suppression of translation by an antisense oligodeoxynucleotide." Antisense Res. Dev., 5:149-154 (1995).

Kim, et al., "Helix-stabilizing compounds CC-1065 and U-71, 184 bind to RNA-DNA and DNA-DNA duplexes containing modified intermucleotide linkages and stabilize duplexes against thermal melting." Antisense Res. Dev., 5:49-57 (1995).

Kopka, et al., "Bindig of antitumor drug to DNA netropsin and C-G-C-G-A-A-T-T-C-G-C-G." J. Mol. Biol., 183:553-63 (1985).

Kubista, et al., "Characterization of interaction between DNA and 4',6-diamidino-2-phenylindole by optical spectroscopy." Biochemistry, 26:4545-4553 (1987).

Kutyavin, I. V. et al., "3—minor groove binder-DNA probes increase sequence specificity at pcr extension temperatures", *Nucleic Acids Research, Oxford University Press*, Surrey, GB, vol. 28, No. 2, 2000, pp. 655-661 (XP002318952).

Lamm, et al., "Antisense probes containing 2-aminoadenosine allow efficient depletion of U5 snRNP from HeLa splicing extracts." Nucleic Acids Res., 19(12):3193-3198 (1991).

Lander, "The new genomics: Global views of biology." Science, 274:536-39 (1996).

Laplanche et al., "Phosphorothioate-modified oligodeoxyribonucleotides. III. NMR and UV spectroscopic studies of the Rp-Rp, Sp-Sp, and Rp-Sp duplexes, d(GG$_S$AATCC)$_2$, derived from diasteromeric O-ethyl phosphorothioates." Nucleic Acids Res., 14(22):9081-9093 (1986).

Larhammar, et al., "Exon-intron organization and complete nucleotide sequence of a human major histocompatibility antigen DCβ gene." Proc. Natl. Acad. Sci. USA, 80:7313-7317 (1983).

Lee, et al., "Allelic discrimination by nick-translation PCT with fluorogenic probes." Nucleic Acids Res., 21(16):3761-66 (1993).

Lee, et al., "Mapping of DNA alkylation sites induced by adozelesin and bizelesin in human cells by ligation-mediation polymerase chain reaction." Biochemistry, 33:6024-6030 (1994).

Liang, et al., "Differential display of eukaryotic messenger RNA by means of the polymerase chain reaction." Science, 257:967-971 (1992).

Little, et al., "Mass spectrometry from miniaturized arrays for full comparative DNA analysis." Nature Med., 3(12):1413-16 (1997).

Livak, et al., Oligonucleotides with fluorescent dyes at opposite ends provide a quenched probe system useful for detecting pcr product and nucleic acid hybridization, PCR Meth. and App., 4:357-362 (1995).

Lokhov, et al., "Synthesis and high stability of complementary complexes of N-(2-hydroxyethyl)phenazinium derivatives of oligonucleotides." Bioconjugate Chem., 3:414-419 (1992).

Lukhtanov, et al., "Direct, solid phase assembly of dihydropyrroloindole peptides with conjugated oligonucleotides." Bioconjugate Chem., 7:564-567 (1996).

Lukhtanov, et al., "Oligodeoxyribonucleotides with conjugated dihydropyrroloindole oligopeptides: preparation and hybridization properties," Bioconjugate Chem., 6:418-426 (1995).

Lutz, et al., "Recognition of uncharged polyamide-linked nucleic acid analogs by DNA polymerases and reverse transcriptases." J. Am. Chem. Soc., 119:3177-78 (1997).

Marck, et al., "Specific interaction of netropsin, distamycin-3 and analogs with I.C duplexes: reversion towards the B form of the 2'deoxy-.2'deoxy-2'-fluoro-hybrid duplexes upon specific interaction with netropsin, distamycin-3 and analogs." Nucleic Acids Res., 10(19):6147-6161 (1982).

Marky, et al., "Origins of netropsin binding affinity and specificity: Correlations of thermodynamic and structural data." Proc. Natl. Acad. Sci. USA, 84:4359-63 (1987).

Marsch, et al., "Non-covalent DNA groove-binding by 2-amino-1-methyl-6-phenylimidazo[4,5-b]pyridine." Nucl. Acid Res., 22(24):5408-15 (1994).

Marshall, "'Playing chicken' over gene markers." Science, 278:2046-48 (1997).

Marshall, "Snipping away at genome patenting." Science, 277:1752-53 (1997).

Mohan, et al., "Flexibility of DNA in 2:1 drug-DNA complexes-simultaneous binding of two DAPI molecules to DNA." J. Biomol. Struct. Dyn., 9(3):695-704 (1994).

Monia, et al., "Evaluation of 2'-modified oligonucleotides containing 2'-deoxy gaps as antisense inhibitors of gene expression." J. Biol. Chem., 268(19):14514-14522 (1993).

Moon, et al., "DNA structural features responsible for sequence-dependent binding geometries of Hoescht 33258." Biopolymers, 38:593-606 (1996).

Moran, et al., "A thymidine triphosphate shape analog lacking Watson-Crick pairing ability is replicated by high sequence selectivity." Proc. Natl. Acad. Sci. USA, 94:10506-511 (1997).

Mullis, et al., "Specific synthesis of DNA in vitro via a polymerase-catalyzed chain reaction." Meth. Enzymol., vol. 155:335-50, Academic Press, New York (1987).

Nielsen, et al., "Peptide nucleic acid (PNA) A DNA mimic with a peptide backbone." Bioconjugate Chem., 5:3-7 (1994).

Nielsen, et al., "Sequence-selective recognition of DNA by strand displacement with a thymine-substituted polyamide." Science, 254:1497-1500 (1991).

Ørum, et al. "Single base pair mutation analysis by PNA directed PCR clamping." Nucleic Acid Research, 21(23):5332-5336 (1993).

Parris, et al., "A signature clement distiguishes sibling and independent mutations in a shuttle vector plasmid." Gene, 117:1-5 (1992).

Pastinen, et al., "Minisequencing: A specific tool for DNA analysis and diagnosis on oligonucleotid arrays." Genome Res., 7:606-14 (1997).

Patel, "Antibiotic-DNA Interactions: Intermolecular nuclear Overhauser effects in the netropsin-d(C-G-C-G-A-A-T-T-C-G-C-G) complex in solution." Proc. Natl. Acad. Sci. USA, 79:6424-28 (1982).

Petrie, et al., "An improved CPG support for the synthesis of 3'-amine- tailed oligonucleotides." Bioconjugate Chemistry, 3:85-~n (1992).

Rao, et al., "Synthesis of novel thiazole-containing DNA minor groove binding oligopeptides related to the antibiotic distamycin." 1. Org. Chem., 55:728-737 (1990).

Reed, et al "Acridine- and cholesterol-derivatized solid supports for improved synthesis of 3'-modified oligonucleotides," Bioconjugate Chem., 2:217-225 (1991).

Remers, et al., "Conformations of complexes between pyrrol[1,4]benzodiazepines and DNA segments." J. Med. Chem, 29:2492-503 (1986).

Reynolds, et al., "Reaction of the antitumor antibiotic cc-1065 with DNA. Location of the site of thermally induced strand breakage and analysis of dna sequence specificity." Biochemisty, 24:6228-6237 (1985).

Risch, "The future of genetic studies of complex human diseases." Science, 273:1516-17 (1996).

Robins, et al., "Nucleic acid related compounds. 38. Smooth and high-yield iodination and chlorination at C-5 or uracil bases and p-toluyl-protected nucleosides." Can. .T. Chem., 60:554-557 (1982).

Robins, et al., "Nucleic acid related compounds. 39. Efficient conversion of 5-iodo to 5-alkynyl and derived 5-substituted uracil base and nucleosides." J. Org. Chem., 48:1854-1862 (1983).

Rougeon, et al., "Insertion of a rabbit β-globin gene sequence into an E. coli plasmid." Nucleic Acids Res, 2(12):2365-2378 (1975).

Saiki, et al., "Enzymatic amplification of β- globin genomic sequences and restriction site analysis for diagnosis of sickle cell anemia." Science, 230:1350-1354 (1985).

Saiki, "The Design and Optimization of the PCR." in: PCR Technology: Principles and Applications for DNA Amplification. Erlich, H.A. (ed.), Chapter 1, pp. 7-16, Stockton Press, (1989).

Sanger, et al., "DNA sequencing with chain-terminating inhibitors." Proc. Natl. Acad. Sci. USA., 74:5463-5467 (1977).

Scahill, et al., "An NMR study of the covalent and noncovalent interactions of CC-1065 and DNA." Biochemistry, 29:2852-2860 (1990).

Schaffer, et al., "DNA variation and the future of human genetics." Nature Biotechnology, 16:33-39 (1998).

Seela, et al., "Alternating d(G-C)$_3$ and d(C-G)$_3$ hexenucleotides containing 7-deaza-2'-deoxyguanosine or 8-aza-7-deaza-2'-deoxyguanosine in place of dG." Nucl. Acid Res., 17(3):901-10 (1989).

Seela, et al., "2'-deoxiribofuranosides of 6-oxoallopurinol and of related 4,6-disubstituted pyrazolo[3,4-d] pyrimidines" Liebigs Ann. Chem. 1986, 1214-21 (1986) (in German, with English Abstract).

Seela, et al., "Synthesis of 2'-deoxyribofuranosides of 8-aza-7-deazaguanine and related pyrazolo[3,4-d]pyrimidines" Helv. Chim. Acta, 69(7):1602-1613 (1986).

Shabarova, et al., "DNA-like duplexes with repetitions. III. Efficient template-guided chemical polymerization of d(TGGCCAAGCTp)." Nucleic Acids Res., 9:5747-5761 (1981).

Shuber, et al., "High throughput parallel analysis of hundreds of patient samples for more than 100 mutations in multiple disease genes." Hum. Mol. Genet., 6(3):337-47 (1997).

Singh, et al., "Isoelicity and strand selectivity in the minor groove binding of chiral (1R,2R)- and (1S,2S)- bis(netropsin)1,2-cyclopropanedicarboxamide ligands to duplex DNA." J. Am. Chem. Soc., 116:7006-20 (1994).

Singh, et al., "Synthesis and sequence-specific DNA binding of a topoisomerase inhibitory analog of Hoechst 33258 designed for altered base and sequence recognition." Chem. Res. Toxocol., 5:597-607 (1992).

Sinyakov, et aL, "Exceptional and selective stabilization of A-T rich DNA-DNA duplexes by N-methylpyrrole carboxamide peptides conjugated to oligodeoxynucleotides." J. Am Chem. Soc., 117:4995-4996 (1995).

Smits, et al., "Detection and typing of human papillomaviruses present in fixed and stained archival cervical smears by a consensus polymerase chain reaction and direct sequence analysis allow the identification of a broad spectrum of human papillomavirus types." J. Gen. Virol., 73:3263-3268 (1992).

Sonyeaux. "The organic chemistry underlying DNA synthesis." Bioinorgan. Chem., 14:274-325 (1986).

Spielman, et al., "Transmission test for linkage disequilibrium: The insulin gene region and insulin-dependent diabetes mellitus (IDDM)." Am. J. Hum. Genet. 52:506-16 (1993).

Sproat, et al., "2'-O-alkyloligoribonucleotides." in: *Antisense Research and Applications*, Crooke, ST. and Lebleu, B. (eds), pp. 351-362, CRC Press, Boca Raton, Fla. (1993).

Stein, et al., "Physiochemical properties of phosphorothioate oligodeoxynucletides." Nucleic Acids Res., 16(8):3209-3221 (1988).

Suggs, et al., "Evidence for sequence-specific conformational changes in DNA from the melting temperatures of DNA posphorothiate derivates." Nucleic Acids Res., 13(15):5707-5716 (1985).

Tabone, et al., "Factors influencing the extent and regiospecificity of cross-link fonnation between single stranded DNA and reactive complementary oligodeoxynucleotides." Biochemistry, 33:375-383 (1994).

Tautz, "Notes on the definition and nomenclature of tandemly repetitive DNA sequences." in: *DNA Fingerprinting: State of the Science*, Pena et al. (ed.), pp. 21-28, Birkhauser, Basel, (1993).

Trotta, et al., "¹H NMR study of [d(GCGATCGC)]₂ and its interaction with minor groove binding 4',6-diaminido-2-phenylindole." J. Biol. Chem., 268(6);3944-51 (1993).

Tung, et al., "PCR Amplification of Specific Sequences from a cDNA Library." in: *PCR Technology: Principles and Applications for DNA Amplification*, Erlich, H.A. (ed.), Chapter 9, pp. 99-104, Stockton Press(1989).

Turner, et al., "The mutagenic properties of DNA minor-groove binding ligands." Mutation Research. 355:141-169 (1996).

Uhlmann, et al., "Synthesis and properties of PNA/DNA chimeras." Angew. Chem. Int. Ed., Engl., 35(22):2632-35 (1996).

Uhlmann, et al., "Synthesis of polyamide nucleic acids (PNAs), PNA/DNA-chimeras and phosphonic ester nucleic acids (PHONAs)." Nucleosides & Nucleotides, 16(5&6):603-8 (1997).

Van Der Laan, et al., "A convenient automated solid-phase synthesis of PNA-(5')-DNA-(3')-PNA chimera." Tetrahedron Lett, 38(13): 2249-52 (1997).

Van Der Laan, et al., "Solid support synthesis of a PNA-DNA hybrid." Recl. Trav. Chim. Pays-Bas, 114:295-7 (1995).

Van Ness, et al., "The use of oligodeoxynucleotide probes in chaotrope-based hybridization solution", Nucleic Acids Res., 19:5143-5151 (1991).

Wagner, et al., "Antisense gene inhibition by oligonucleotides containing C-5 propyne pyrimidines." Science, 260:1510-1513 (1993).

Wartell, et al., "Netropsin: A specific probe for A-T regions of duplex deoxyribonucleic acid." J. Biol. Chem., 249(21):6719-6731 (1974).

Webb, et al., "Hybridization triggered cross-linking of deoxyoligonucleotides." Nucleic Acids Res., 14:7661-7674 (1986a).

Webb, et al.; "Sequence-Specific Cross-Linking of Deoxyoligonucleotides via Hybridization-Triggered Alkylation." J. Am Chem. Soc., 108:2764-2765 (1986b).

Wemmer, et al., "Targeting the minor groove of DNA." Curr. Opin. Struct. Biol. 7(3):355-361 (1997).

Wiederholt, et al., "DNA-tethered Hoechst groove-binding agents: Duplex stabilization and fluorescence chararcteristics." J. Am Chem. Soc., 118:7055-7062 (1996).

Wiederholt, et al., "Oligonucleotides tethering Hoechst 33258 derivatives: Effect of the conjugation site on duplex stabilization and fluorescence properties." Bioconjugate Chem., 8:119-126 (1997).

Williams, et al., "Genetic analysis using random amplified polymorphic DNA markers." i Methods in Enzymology, 218(1):704-740, Academic Press, New York (1993).

Wittwer, et al., "Continuous fluorescence monitoring of rapid cycle DNA amplification." Biotechniques, 22(1):130-138 (1997).

Wittwer, et al., "The LightCycler™: A microvolume multisample fluorimeter with rapid temperature control." Biotechniques, 22(1):176-181 (1997).

Seela et al., "7-Deazapurin-2,6-Diamine and 7-Deazaguanine: Synthesis and Property of 7-Substituted Nucleosides and Oligonucleotides", *Nucleosides, Nucleotides and Nucleic Acids*, 24 (5-7):839-841 (2005).

Seela et al., Propynyl Groups in Duplex, Hairpin and Triplex DNA: 7-Deazapurines and 9-Deazapurines, *Nucleosides, Nucleotides, and Nucleic Acids*, 24(5-7):851-854 (2005).

Seela et al., Stabilization of Tandem dG-dA Base Pairs in DNA-Hairpins: Replacement of the Canonical Bases by 7-Deaza-7-Propynylpurines, *Org. Biomol. Chem.*, 3: 4221-4226 (2005).

Amplicon
*ATATTCTTTGCCAGGTATT*<u>CCTCTCTN[G/T]CATCTC</u>ATCTTGTAAAATTATA
TCCANAGGATGTAATATTATGCCCATG*CGATACTAAGGCGAGAAGTT*

Primers
    AaCTTCTCGCCTTAGTATCG
    ATaTTCTTTGCCaGGTATT
Probes
    MGB-Q-GAGATGCU$_{40}$AGAGAGG-Fa    (Probe Fa)
    MGB-Q-GAGATGAU$_{40}$AGAGAGG-Fb    (Probe Fb)

| | $\Delta G°$ | $T_m$ |
|---|---|---|
| -AgG- | | |
| #25, g/T | -8979 | 37.14 |
| #26, g/A | -9366 | 38.70 |
| #27, g/G | -9186 | 37.94 |
| #28, g/C | -13055 | 50.35 |
| -AgC- | | |
| #30, g/T | -9969 | 40.70 |
| #31, g/A | -10414 | 42.54 |
| #32, g/G | -10613 | 43.02 |
| #33, g/C | -13849 | 53.09 | a) -AgN- (5' -A-) thermodynamic data

| | $\Delta G°$ | $T_m$ |
|---|---|---|
| -AgA- | | |
| #10, g/T | -8785 | 36.47 |
| #11, g/A | -8793 | 36.49 |
| #12, g/G | -8493 | 35.47 |
| #13; g/C | -12608 | 48.50 |
| -AgA- | | |
| #15, g/T | -7845 | 32.71 |
| #16, g/A | -8018 | 33.33 |
| #17, g/G | -7737 | 32.26 |
| #18, g/C | -11673 | 46.08 |
| -AgT- | | |
| #20, g/T | -7937 | 33.50 |
| #21, g/A | -8080 | 33.87 |
| #22, g/G | -8222 | 34.52 |
| #23, g/C | -12061 | 46.89 |

SINGLE NUCLEOTIDE POLYMORPHISM ANALYSIS OF HIGHLY POLYMORPHIC TARGET SEQUENCES

CROSS-REFERENCES TO RELATED APPLICATIONS

This application claims the benefit of U.S. Provisional Application Ser. No. 60/508,792, filed Oct. 2, 2003, the contents of which are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention is directed to a process to analyze single nucleotide polymorphisms (SNPs) in highly polymorphic nucleic acids, particularly in those targets that contain one or more additional polymorphisms close to the SNP of interest.

Typically genotyping of a single nucleotide polymorphism is performed using a probe or a primer containing a single mismatch. This simplifies the analysis of alleles tremendously. However, the presence of more than one polymorphism in a probe region complicates genotyping and makes detection very difficult if not impossible for many SNP detection methods. Most SNP detection methods present difficulties in genotyping a polymorphism of interest if the probe sequence spans another polymorphism.

Single nucleotide polymorphisms (SNPs) are the most abundant of variations in the human genome, accounting for >90% of sequence polymorphisms. They occur on average once every 1000 nucleotides so that, as a rule of thumb, there is a 0.1% chance of any base position being heterozygous in a particular individual. Nucleotide diversity is not constant over the entire genome, with areas of extremely low diversity, for example, the X chromosome, and areas of extremely high diversity, for example, up to 10% in the human leukocyte antigen (HLA) loci (Twyman and Primrose, *Pharmacogenomics* 4: 1-13 (2002)). Highly polymorphic SNP target sequences are also known in other species, e.g., plants (Ching A, Caldwell K S, Jung M, Dolan M, Smith O S, Tingey S, Morgante M, Rafalski A J. *BMC Genet.* 3: 19 (2002)) and viruses (Miller V, Larder B A. *Antivir Ther.* 6 Suppl 3:25-44 (2001)). Many SNP detection methods have been described to detect a single polymorphism in a nucleic acid target in absence of another polymorphism in close proximity (Twyman and Primrose, supra; Gerome Breen, *Psychiatric Genetics,* 12: 83-88 (2002)). Genotyping by melting curve analysis has been developed (see, U.S. Pat. Nos. 6,569,627; 6,506,568; 6,448,015 and U.S. application Ser. No. 10/165,410, each of which is hereby incorporated herein by reference).

Others have not designed probes or used universal bases to identify a polymorphism of interest when a second polymorphism resides within the length of the probe, such that the probe incorporates a universal base in a location to pair with the second polymorphism. For instance, in a summary of applications for universal base analogues, David Loakes, *Nucl. Acids Res.,* 29: 2437-2447 (2001), discusses SNP analysis, but not when more than one polymorphism is covered by the probe. Bergstrom et al, *J. Amer. Chem. Soc.,* 117: 1201-1209 (1995) disclose the synthesis of 1-(2'-deoxy-β-D-ribofuranosyl)-3-nitropyrrole. The melting temperatures ($T_m$s) of 15-mer oligonucleotides containing a single universal base hybridized to a complement containing either A, C, G or T at that position were within 3° C. However, the $T_m$s were significantly lower than that of fully matched oligonucleotides. Guo et al, (*Nat. Biotech.,* 15: 331-335 (1997) and U.S. Pat. No. 5,780,233)), disclose the use of 3-nitropyrrole to increase mismatch discrimination by the introduction of this base as an artificial mismatch. U.S. Patent Publication 2003/0165888 discloses probe and primers that contain at least two juxtaposed universal bases. Bowden et al (*Thromb. Heamost.,* 80: 32-36 (1998)) disclose the simultaneous detection of multiple SNPs using a probe that contains a microdeletion or microinsertion of natural bases in the vicinity of established mutation sites. WO 03/040395 discloses universal nucleotides referred to as extendable nucleotides that can be incorporated into a polynucleotide strand by a polymerase during a primer extension reaction. EP 1314734 discloses a limited number of LNA substituted phosphoramidite reagents. WO 02/062816 discloses a large number of universal base triphosphate derivatives for pharmaceutical applications.

Several publications disclose universal bases without discussing their application in SNP analysis. For example, Lin, PKT and Brown, D M, *Nucl. Acids Res.,* 20: 5149-5152 (1992) disclose two new degenerated bases that can be used in probes and primers, 6H,8H-3,4-dihydropyrmido[4,5-c][1,2]oxazin-7-one (P) and 2-amino-6-methoxyaminopurine (K), but do not disclose their use in mismatch discrimination or genotyping. Due to their ability of both base P and base K to exist in their amino and imino tautomers, they base pair with both A and G, and C and T, respectively. McMinn et al, *J. Amer. Chem. Soc.,* 121: 11585-11586 (1999) and Ogawa et al, *J. Amer. Chem. Soc,* 122, 3274-3287 (2000) disclose the synthesis of unnatural nucleobases based on an isocarbostyryl core structure. Matsuda et al, *J. Amer. Chem. Soc.,* 125: 6134-6139 (2003), disclose the synthesis of four unnatural bases, each of which hybridize with all four natural bases relatively similarly. Kim et al, *Biorg. Med. Chem. Let.,* 12: 1977-1980 (2002) disclose the base pair properties of 8-oxo-7,8-dihyroadenosine. Henry et al, *J. Amer. Chem. Soc.,* 125: 9638-9646 (2003) disclose six new unnatural bases, but did not investigate SNP analysis. Seela and Debelak (*Nucleosides, Nucleotides & Nucl. Acids,* 20: 577-585 (2001); Seela and Debelak (*Nucl. Acids Res.,* 28: 3224-3232 (2000) and WO 01/72764 disclose three universal bases which showed no significant structural discrimination with natural analogs A, C, G and T. EP 1314734 discloses a limited number of LNA substituted phosphoramidite reagents. WO 02/062816 discloses a large number of universal base triphosphate derivatives for pharmaceutical applications.

Nucleic acid target amplified-based analyses are disclosed in U.S. Pat. Nos. 4,800,159; 6,197,563; 5,210,015; 5,312,728; and 6,221,603, each of which is hereby incorporated by reference.

Natural modified base analogs and their properties have been disclosed in WO 01/65958, U.S. Pat. Nos. 6,127,121;

6,660,845; and RE 38,416 and Seela et al, *Helv. Chim., Acta,* 69:1602-1613 (1986) each of which is incorporated herein by reference.

Accordingly, there is a need for primers/probes that can distinguish a first SNP of interest that is located within the length of a probe of a second SNP, and methods for designing and using such primer/probes. The present invention fulfills this and other needs.

BRIEF SUMMARY OF THE INVENTION

The present invention provides, in one aspect, a method for continuous monitoring of polynucleotide amplification of a target nucleic acid sequence having at least two single nucleotide polymorphisms wherein a first single nucleotide polymorphism is to be distinguished and a second single nucleotide polymorphism is not distinguished, each of said polymorphisms being in a probe region of said target nucleic acid, the method comprising:

(a) combining a sample containing said target nucleic acid with one or more oligonucleotide primers adjacent to or overlapping with said probe region of the target sequence, a polymerizing enzyme, nucleotide substrates, and an oligonucleotide conjugate having a formula:

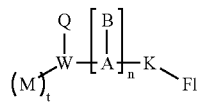

wherein M is a minor groove binder; the subscript t is 0 or 1; Q is a quencher; W is a linking group; K is a bond or a linking group; Fl is a fluorophore; and [A-B]$_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In some embodiments, the probe has the formula:

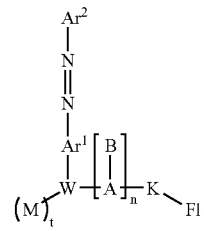

in which M, W, A, B, K, Fl, t and n have the meanings provided above, and Ar$^1$ and Ar$^2$ are substituted aromatic rings, typically substituted benzene rings, wherein the substituents are selected from those generally provided for aryl groups below, and additionally, Ar$^2$ can be substituted with an arylazo group or styryl group to provided a further extended bis-azo dye or analog thereof. Preferred substituents for mono-azo and bis azo dyes are provided below.

In still further preferred embodiments, the methods of the invention employ oligonucleotide probes/conjugates having the formula:

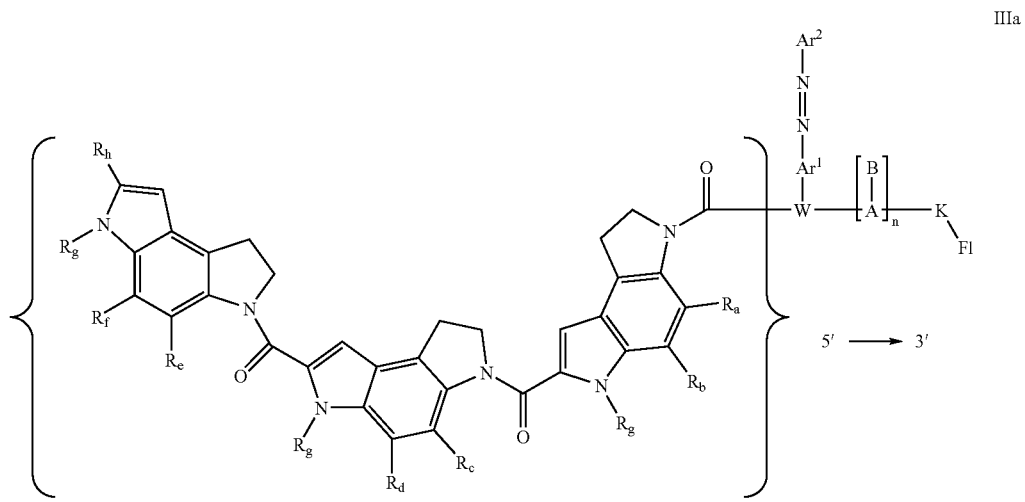

-continued

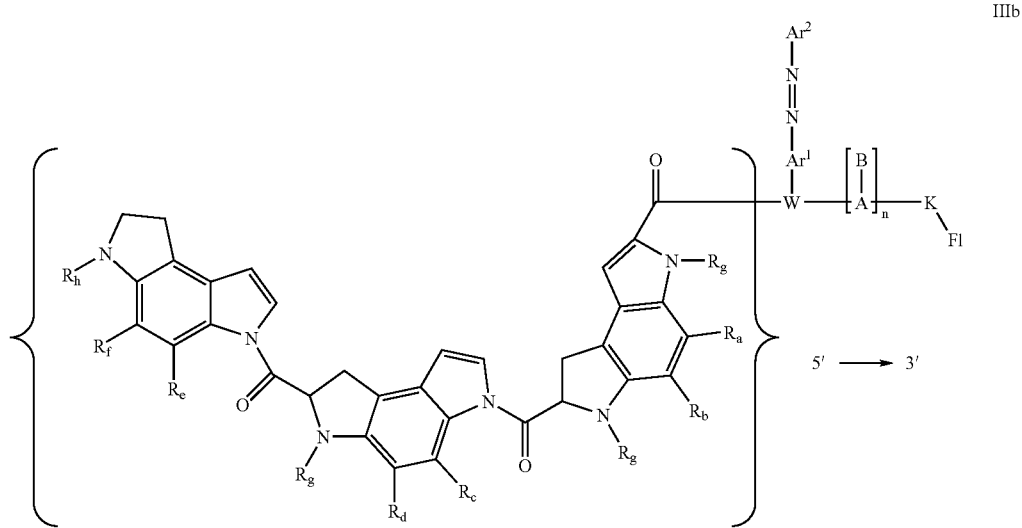

wherein $Ar^1$, $Ar^2$, W, K, Fl, A, B, and the subscript n have the meanings provided above, and wherein the symbols $R_a$, $R_b$, $R_c$, $R_d$, $R_e$ and $R_f$ represent substituents selected from H, halogen, $(C_1$-$C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_m$ $OPO_3^{-2}$, and $NHC(O)(CH_2)_mCO_2^-$, and esters and salts thereof, wherein each $R_g$ is independently H or $(C_1$-$C_8)$alkyl, and the subscript m is an integer of from 0 to 6. The symbol $R_h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences.

In still further preferred embodiments, the oligonucleotide probes/conjugates have the formula:

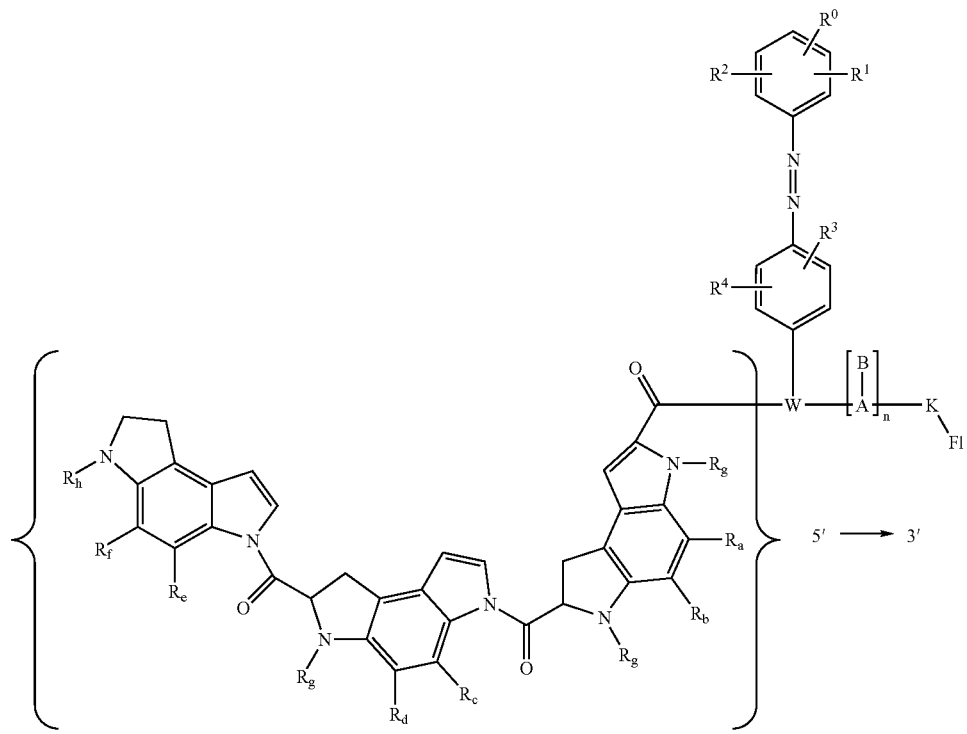

wherein W, K, Fl, A, B, $R_a$ through $R_h$, and the subscript n have the meanings provided above, and wherein the symbols $R^0$, $R^1$ and $R^2$ represent H or preferably electron-withdrawing groups (wherein electron-withdrawing refers to groups that have greater electronegativity than a hydrogen atom, e.g., nitro, cyano, acetyl and the like and one of $R^0$, $R^1$ and $R^2$ can represent an extended arylazo or styryl moiety) and, the symbols $R^3$ and $R^4$ represent H or preferably electron-donating groups (wherein electron-donating refers to groups that are more electropositive than a hydrogen atom, e.g., alkyl, alkoxy, alkylamino and the like). For those embodiments in which a bis-azo dye or extended system (e.g., wherein $R^0$ is —N=N—$Ar^3$ or —CH=CH—$Ar^3$), the terminal aromatic ring ($Ar^3$) will be unsubstituted or preferably substituted with electron-withdrawing substituents and $Ar^1$ and $Ar^2$ rings will be unsubstituted or preferably substituted with electron-donating substituents. In a particularly preferred embodiment, W is —(CH$_2$)$_3$N(-)—(CH$_2$)$_3$—; $R^0$=NO$_2$; $R^1$=Cl; $R^2$=$R^3$=$R^4$=H; and K is a (C$_1$-C$_6$)alkylene linker. In one embodiment, M and Fl each can be independently attached at either the 5'- or 3'-end of the probe.

Related methods are provided in the Detailed Description below, for the use of oligonucleotide probes/conjugates having a promiscuous base at the site of a SNP that is to be masked during the associated assay. The methods are drawn to distinguishing between wild-type, mutant and heterozygous target polynucleotides in a sample, wherein the target contains a SNP that is to be distinguished and a SNP that is not to be distinguished.

DETAILED DESCRIPTION OF THE INVENTION

Definitions and Abbreviations

Figures 1, 2:
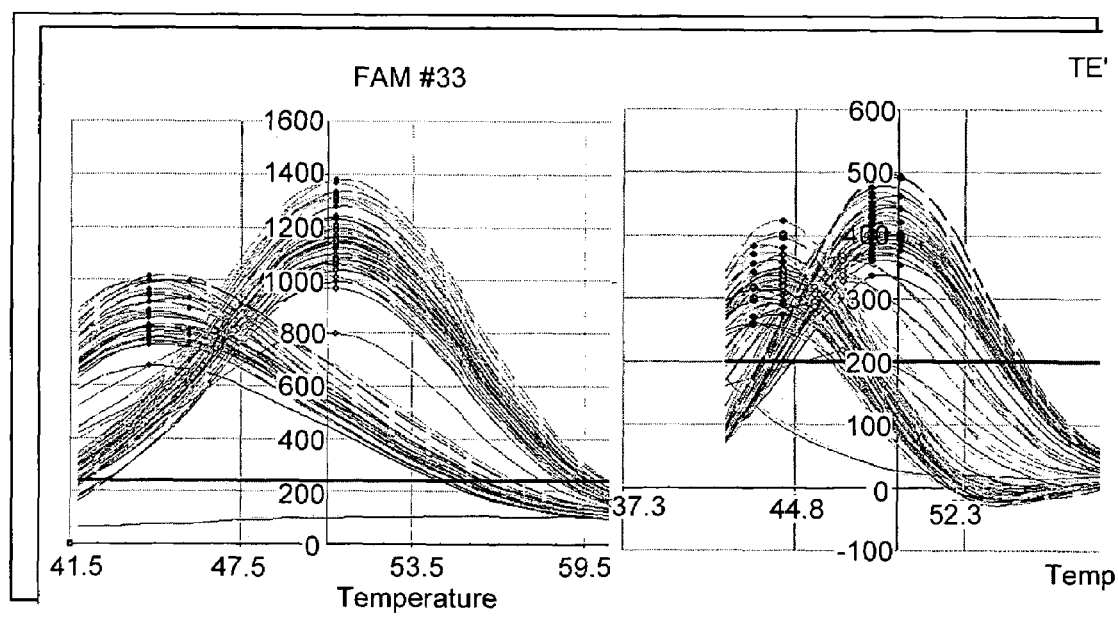
FIG. 1. Sequence of amplicon (SEQ ID NO:1), primers (SEQ ID NO:2 and 3) and probes (SEQ ID NO:4 and 5). Fa is fluorescein and Fb is tetrachlorofluorescein. "a" is Super A™. MGB is a substituted dihydrocyclopyrroloindole triamide (DPI$_3$), the MGB™ ligand is a trademark of Epoch Biosciences, Bothell, Wash., primers are in bold italics and the probe is bold underlined. N represents the second natural polymorphism. [G/T] represents the polymorphism of interest. $U_{40}$ is 6-Amino-2-(4-hydroxy-5-hydroxymethyl-tetrahydro-furan-2-yl)-2,5-dihydro-pyrazolo[3,4-d]pyrimidin-4-one (40).
FIG. 2. Melting curves analysis of the sample 4188 DNA containing a double polymorphism in the probe binding area, with probes labeled with fluorescein and tetrachlorofluorescein, complementary to the wild-type and mutant targets of the first polymorphism, respectively. The base corresponding to the second polymorphism was substituted with universal base 40.
Figure 3:
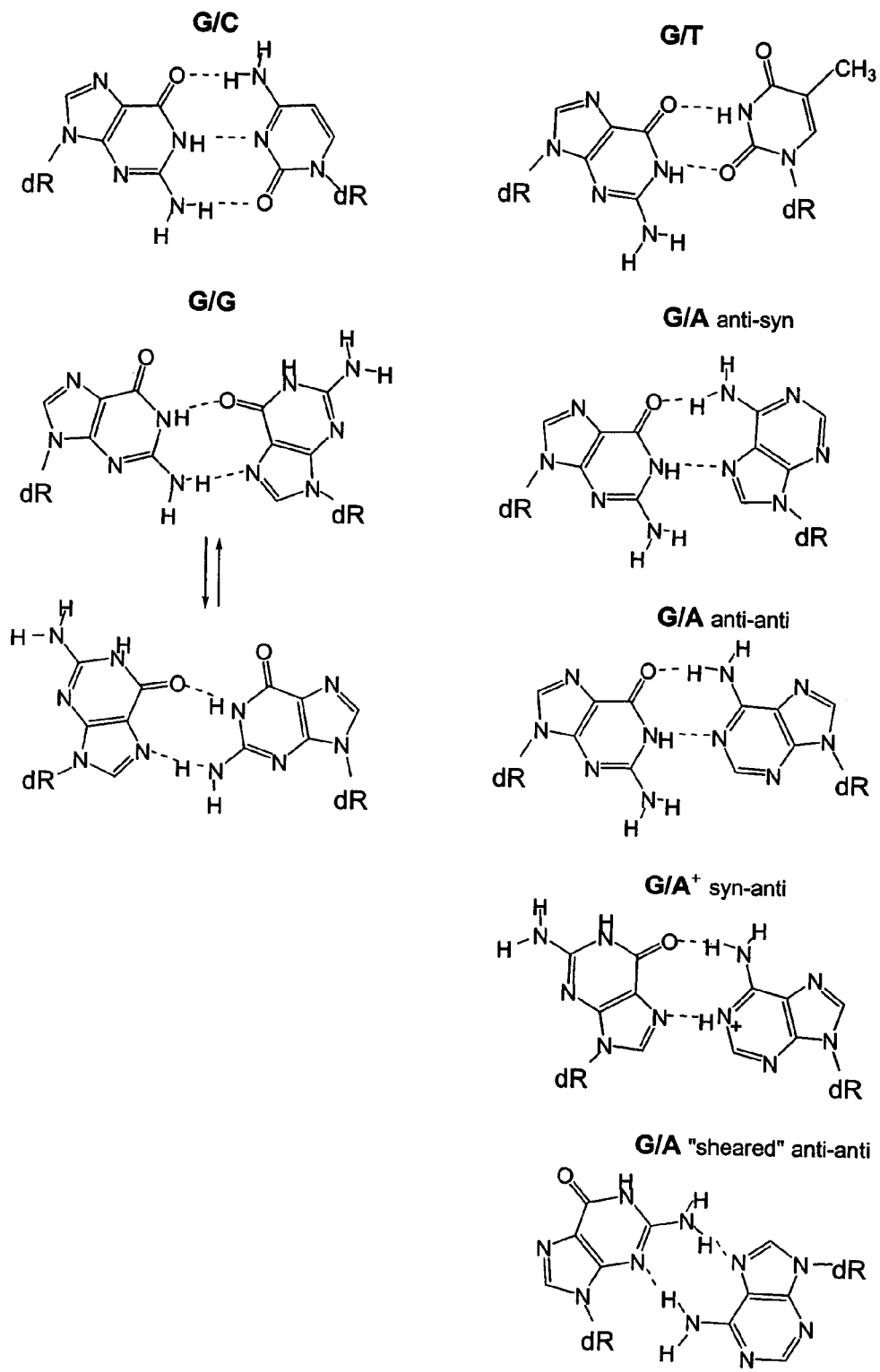
FIG. 3. Provides guanine base pairing geometry with cytidine, guanine, thymine and adenine bases.
Figure 4:
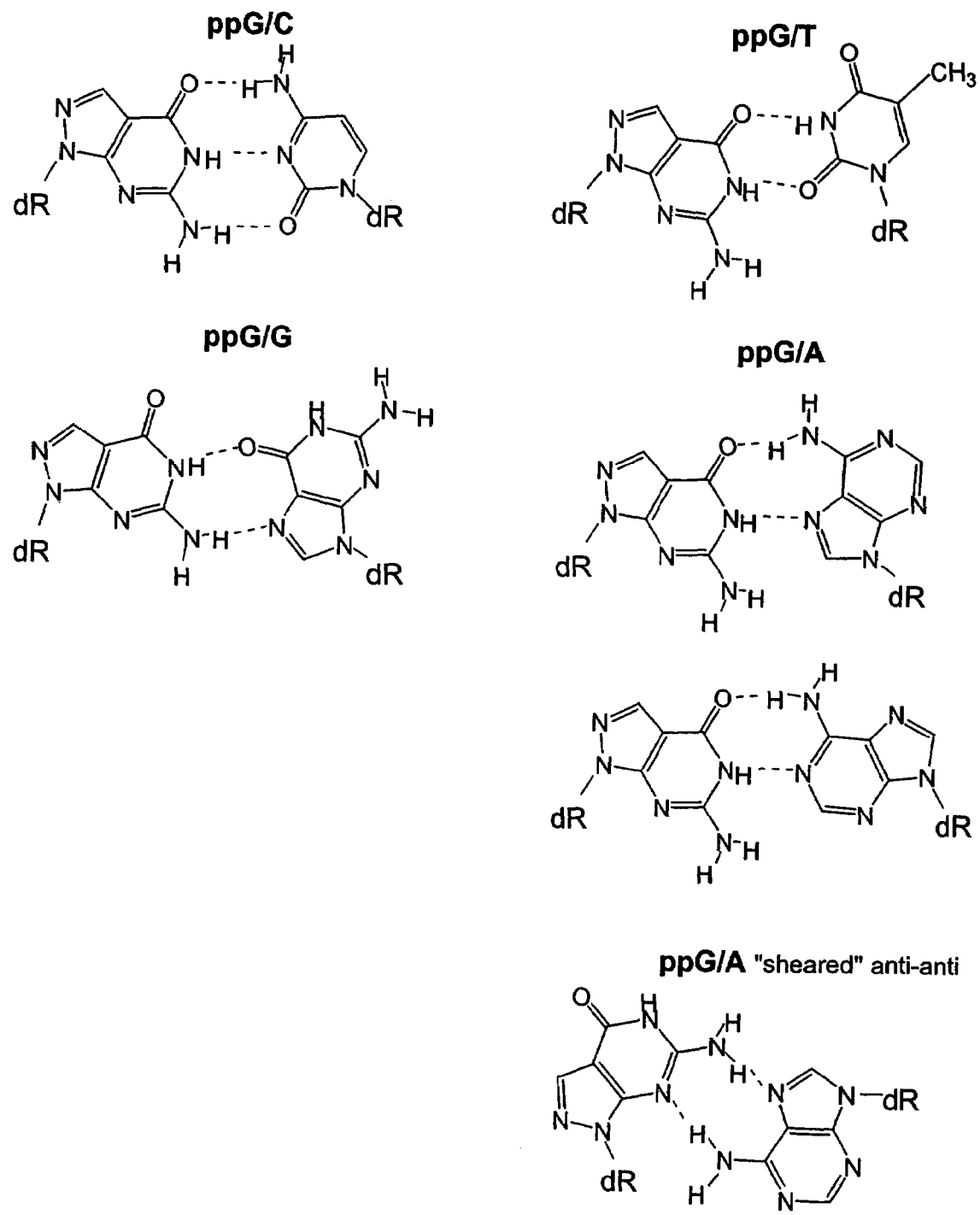
FIG. 4. Provides PPG (Super G) base pairing geometry with cytidine, guanine, thymine and adenine bases.
Figure 5:
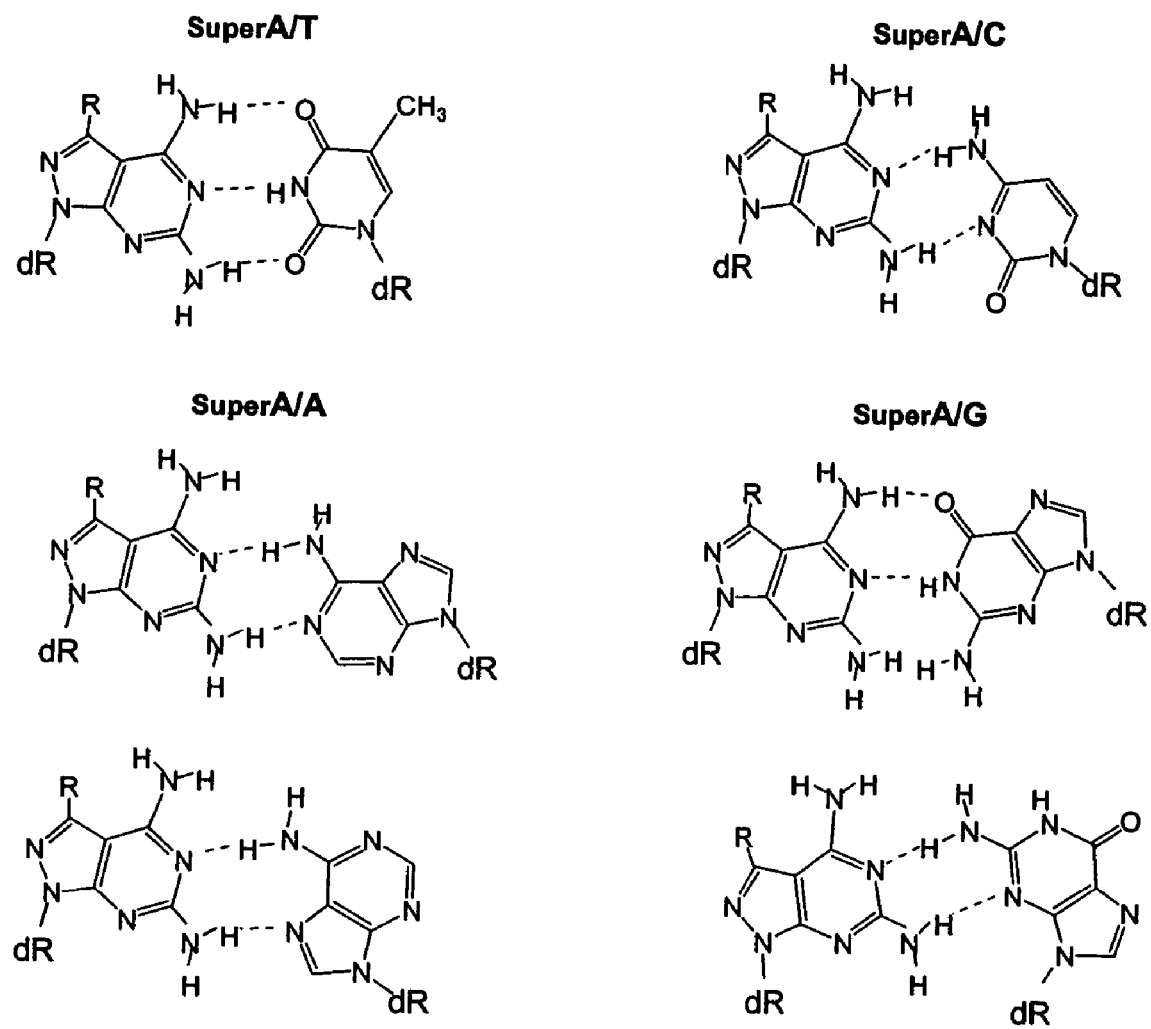
FIG. 5. Provides Super A base pairing geometry with cytidine, guanine, thymine and adenine bases.

The following abbreviations are used in the specification: M,="minor groove binder", MGB™ ligand is a substituted dihydrocyclopyrroloindole triamide (DPI$_3$); Fl="fluorescent label" or "fluorophor"; Q="quencher"; CPG="controlled pore glass" (as an example of a solid support); and ODN="oligonucleotide" moieties or molecules.

In certain formulae, the group [A-B] is used to refer to a monomer unit in an oligonucleotide, modified oligonucleotide or peptide-nucleic acid having multiple bases (B) and being linked along a backbone of multiple sugars, modified sugars or amino acids (A). B refers to normal and modified bases (including, where appropriate, a universal or promiscuous base).

The terms "probe" and "conjugate" are used interchangeably and refer to an oligonucleotide having an attached minor groove binder, fluorophore and quencher.

The term "universal base" refers to a base analog that forms "base pairs" with each of the natural DNA or RNA bases with little discrimination between them.

The term "promiscuous (indiscriminative) base" refers to a natural base or a natural base analog that in addition to the perfect complement match base, forms two hydrogen bonds with two or more natural mismatched bases in DNA or RNA with little discrimination between them.

The terms "fluorescent label" or "fluorophore" refers to compounds with a fluorescent emission maximum between about 400 and 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO®-1 (533), JOE (548), BODIPY® 530/550 (550), Dil (565), BODIPY®™R (568), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642), C-Phycocyanin (648), TO-PRO™-3 (660), TOTO®-3 (660), DiD DilC(5) (665), Cy5™ (670), Thiadicarbocyanine (671), Cy5.5 (694).

The term "linker" refers to a moiety that is used to assemble various portions of the molecule or to covalently attach the molecule (or portions thereof) to a solid support. Typically a linker or linking group has functional groups that are used to interact with and form covalent bonds with functional groups in the ligands or components (e.g., fluorophores, oligonucleotides, minor groove binders, or quenchers) of the conjugates described and used herein. Examples of functional groups on the linking groups (prior to interaction with other components) include —NH$_2$, —NHNH$_2$, —ONH$_2$, —NHC=(O)NHNH$_2$, —OH, or —SH. The linking groups are also those portions of the molecule that connect other groups (e.g., phosphoramidite moieties and the like) to the conjugate. Additionally, a linker can include linear or acyclic portions, cyclic portions, aromatic rings or combinations thereof.

The term "solid support" refers to any support that is compatible with oligonucleotides synthesis, including, for example, glass, controlled pore glass, polymeric materials, polystyrene, beads, coated glass and the like.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, (C$_1$-C$_8$)alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms. For "heteroalkyl" groups (including "heteroalkenyl" and "heteroalkynyl" groups), the term is meant to include alkyl groups wherein one or two carbon atoms are replaced by O, N, NH or S, with the understanding that the heteroatom occupies an interior position of the alkyl chain (i.e., does not form the point of attachment to the remainder of the molecule and is not at the terminous of the alkyl group). As a result, the heteroalkyl groups will have at least two carbon atoms present and the designated number of carbon atoms refers only to the carbon atoms.

The term "alkylene" means a linear saturated divalent hydrocarbon radical or a branched saturated divalent hydrocarbon radical having the number of carbon atoms indicated in the prefix. For example, (C$_1$-C$_6$) alkylene is meant to include methylene, ethylene, propylene, 2-methylpropylene, pentylene, and the like.

The term "aryl" means a monovalent or bivalent (e.g., arylene) monocyclic or bicyclic aromatic hydrocarbon radical of 5 to 10 ring atoms which is unsubstituted or substituted independently with one to four substituents, preferably one, two, or three substituents selected from those groups provided below. Ther term "aryl" is also meant to include those groups described above wherein one or more heteroatoms or heteroatom functional groups have replaced a ring carbon, while retaining aromatic properties, e.g., pyridyl, quinolinyl, quinazolinyl, thienyl, and the like. More specifically the term aryl includes, but is not limited to, phenyl, 1-naphthyl, 2-naphthyl, thienyl and benzothiazolyl, and the substituted forms thereof.

Substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R'", —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. In some embodiments of the invention, an aryl substituent is, as indicated, an aryl azo group (—N=N—Ar) or a styryl group (—CH=CH—Ar).

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Still further, one of the aryl rings (Ar$^1$ and Ar$^2$, below) can be further substituted with another substituted aryl group to extend the resonance ability of the aromatic system, directly or indirectly through groups such as —(CR'=CR')$_n$— and —(C≡C)$_n$—, where n is 0 to 5, increasing the wavelength absorbance maximum.

The prefix "halo" and the term "halogen" when used to describe a substituent, refer to —F, —Cl, —Br and —I.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention. Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g, $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1991) and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. In general, the preferred protecting groups are those that can be removed under acidic conditions or basic conditions, or those groups that can be removed by the use of a particular light source (e.g., "light sensitive" protecting groups). Additionally, selection of an appropriate protecting group is made with due consideration to other functionality in the molecule so that either the incorporation or removal of the protecting group does not interfere or otherwise significantly affect the remainder of the molecule.

"Optional" or "optionally" in the above definitions means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or disubstituted with an alkyl group and situations where the aryl group is not substituted with the alkyl group.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Third Edition, Cold Spring Harbor Laboratory Press (2001); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Ausubel, et al., SHORT PROTOCOLS IN MOLECULAR BIOLOGY, $5^{th}$ Edition, Current Protocols (2002); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The term "Eclipse™ probe" refers, in general, to a 5'-MGB-Q-ODN-Fl probe. In contrast, a "TaqMan® MGB probe refers to a 3'-MGB-Q-ODN-Fl probe. Eclipse™ and MGB™ are trademarks of Epoch Biosciences, Inc., Bothell, Wash.; and TaqMan® is a registered trademark of Applied Biosystems, Inc., Foster City, Calif.

General

The present invention identifies and employs a universal or promiscuous base in a probe or primer that, when substituted for a base in the location of a polymorphism, has similar stability for pairing with an A, C, G or T nucleotide. Substitution of the base in the probe that is in the location of the second polymorphism (e.g., not intended to be genotyped) with a universal base gives hybridization characteristics independent of A, C, G or T substitution. The universal base in the probe essentially makes the second polymorphism "invisible" and allows the specific identification of the first polymorphism of interest, allowing the use of standard genotyping hybridization based methods.

The present invention also identifies and employs a promiscuous (indiscriminative) base, a natural or a natural base analog, in a probe or primer when substituted for a base in the location of a polymorphism, with the characteristics that except for the perfect matched formed:

a) it forms two hydrogen bonds with at least two or more of any of the mismatched natural A, C, G or T nucleotides, b) has similar thermodynamic properties for pairing with two or more of any of the natural mismatched A, C, G or T nucleotides, taken inconsideration the contribution of the nearest neighbors ($-B^A-N^P-B^B-$; where $B^A$ and $B^B$ are independently G, C, A or T), and c) substitution of the base occurs in the probe in the location of the second polymorphism (e.g., not intended to be genotyped) with a promiscuous (indiscriminative) base gives thermodynamic characteristics of base pairing independent of at least two of the A, C, G or T substitutions.

Description of the Embodiments

Probes and Conjugates

The methods of the present invention utilize oligonucleotide probes (or oligonucleotide conjugates, hereinafter "probes/conjugates", "probes" or "conjugates") comprising, a) a nucleic acid sequence complementary to a target nucleic acid sequence comprising a first single nucleotide polymorphism of interest for distinguishing (typically between wild-type, mutant and heterozygous polynucleotides) and at least one additional single nucleotide polymorphism within the probe sequence length, b) one or more universal of promiscuous (indiscriminative) bases positioned for complementary pairing to each of the one or more additional single nucleotide polymorphisms, wherein the probe is used to distinguish the first single nucleotide polymorphism.

Broadly, the present method provides oligonucleotide probes (or oligonucleotide conjugates, hereinafter "probes/conjugates", "probes" or "conjugates") which are most generally noted as $M_t$-Q-[A-B]$_n$-K-Fl probes or conjugates. As noted above, this linear depiction of the probes is meant to indicate that a minor groove binder and a quencher or quenching agent are attached to either the 3' of 5' end of the oligonucleotide portion, and a fluorophore is attached to the other end of the oligonucleotide portion. For any of these covalently attached portions, connection can be either direct or via a linking group. In some embodiments, linking groups (W and K in formula I) are preferred to provide sufficient spacing between interactive portions (e.g., fluorophore and quencher) or reactive portions (e.g., minor groove binders that are meant to bind non-covalently in the minor groove formed by probe hybridization to a target sequence).

Accordingly, in one group of embodiments, the probe or conjugate has the formula:

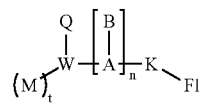

(I)

wherein M is a minor groove binder, Q is a quencher with an absorption spectra between about 400 to 800 nm, W is a linking group, K is a bond or a linking group, Fl is a fluorophore with emission between about 400 to 800 nm, [A-B] represents a monomer unit in a nucleic acid oligomer (e.g., DNA, RNA, PNA or any combination thereof, including those with modified bases and sugars), wherein A represents a sugar phosphate backbone, modified sugar phosphate backbone, locked nucleic acid backbone, peptidic backbone or a variant thereof used in nucleic acid preparation; and B represents a nucleic acid base, a modified base or a base analog as described in more detail below. At least one B is replaced with a universal or promiscuous (indiscriminative) base substituted at the site of a single nucleotide polymorphism which is intended to be masked (or rendered invisible) by the probe. More particularly, the oligonucleotide portion of the probe is designed to have a combination of natural bases or modified bases that are complementary to non-SNP sites on the target of interest, and at least one universal or promiscuous (indiscriminative) base at a SNP site of a multiple SNP-containing target, leaving one SNP of the target "unmasked" for genotyping. The subscript t is an integer of from 0 to 1 and the subscript n is an integer of from 5 to 50.

More particularly, when K is a linking group, it will generally have from 1 to 30 main chain atoms (counting only those atoms between the oligonucleotide portion and the Fl component that are joined in a continuous line, including all ring atoms, but not including any pendant atoms or groups) that are selected from C, O, N, S, P and Si. The linking group W will generally represent a trivalent linker having up to about 100 main chain atoms, selected from C, O, N, S, P and Si. Additionally, W can contain a branched aliphatic chain, a heteroalkyl chain, one or more substituted ring structures, or combinations thereof. In some embodiments, W represents a trivalent moiety such as an amino group with or without pendent functionalized linking groups such that Q-W represents a quencher from, for example, commercial sources (see Table 3 of quenchers below). Accordingly, while W is provided as a linking group, it will in some embodiments be an amino group that may be considered a part of Q. Each of the linking groups, as well as other components, will be discussed in more detail below.

In some embodiments, the oligonucleotide probes used in the present invention have the formula:

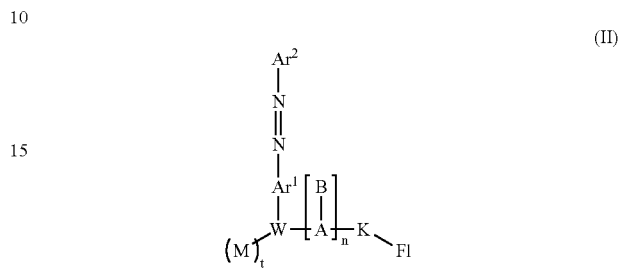

(II)

in which M, W, A, B, K, Fl, t and n have the meanings provided above, and $Ar^1$ and $Ar^2$ are substituted aromatic rings, typically substituted benzene rings. In general, $Ar^1$ will be unsubstituted or substituted with groups that are electron-donating groups (e.g., groups that have an electropositive character relative to hydrogen, such as alkyl, alkoxy, alkylamino and the like). Similarly, $Ar^2$ will preferably be unsubstituted or substituted with one, two or three electron-withdrawing groups (e.g., nitro, cyano, halogen, acyl and the like). In some embodiments, $Ar^2$ will be substituted with a group having the formula —U=U—$Ar^3$, wherein $Ar^3$ is an aryl or heteroaryl moiety, preferably a benzene ring having from 0 to 3 electron-withdrawing groups as substituents and each U is N or CH. In this latter group of embodiments, when $Ar^3$ is substituted with electron-withdrawing groups, each of $Ar^1$ and $Ar^2$ will be independently unsubstituted or substituted with electron-donating groups.

In other preferred embodiments of formula II, the symbol $Ar^1$ represents an aryl group (preferably a benzene ring) which is substituted with one or more electron-donating groups, such as, for example, alkyl, alkoxy, hydroxy, amino, alkylamino, dialkylamino, and the like, and $Ar^2$ represents an aryl group (e.g., a benzene ring) which is substituted with one or more electron-withdrawing groups, such as, for example, nitro, cyano, carboxy, sulfonyl, halogen, and the like.

In still other preferred embodiments, $Ar^2$ is substituted with a group having the formula —U=U—$Ar^3$, wherein each U is independently selected from CH, C(R) and N, in which R is a ($C_1$-$C_8$)alkyl group and $Ar^3$ is a substituted or unsubstituted aryl group. Preferred aryl groups for each of $Ar^1$, $Ar^2$ and $Ar^3$ are phenyl groups. Within this group of preferred embodiments, $Ar^1$ and $Ar^2$ are preferably phenylene, which is unsubstituted or preferably substituted with electron-donating groups (relative to a hydrogen atom), while $Ar^3$ is phenyl, preferably unsubstituted or substituted with electron-withdrawing groups (relative to a hydrogen atom).

In still further preferred embodiments, the methods of the invention employ oligonucleotide probes/conjugates having the formula:

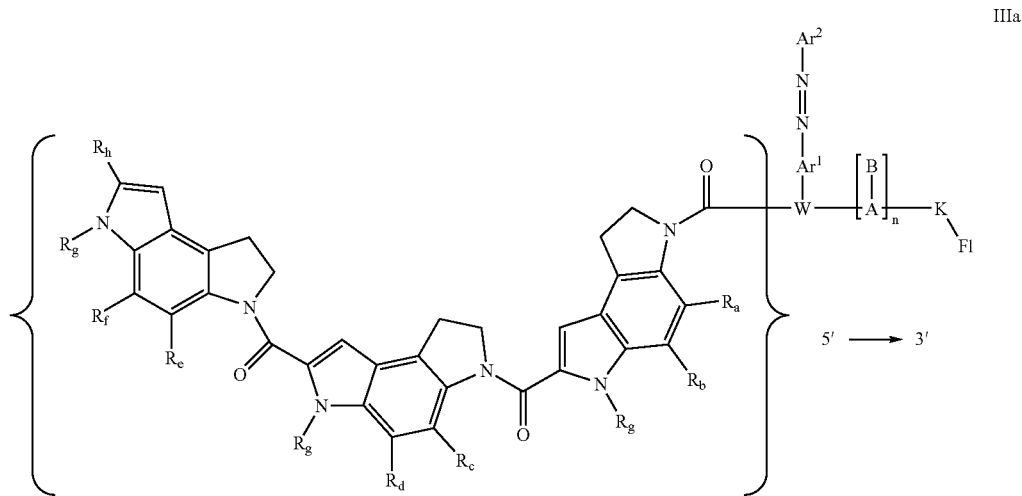

IIIa

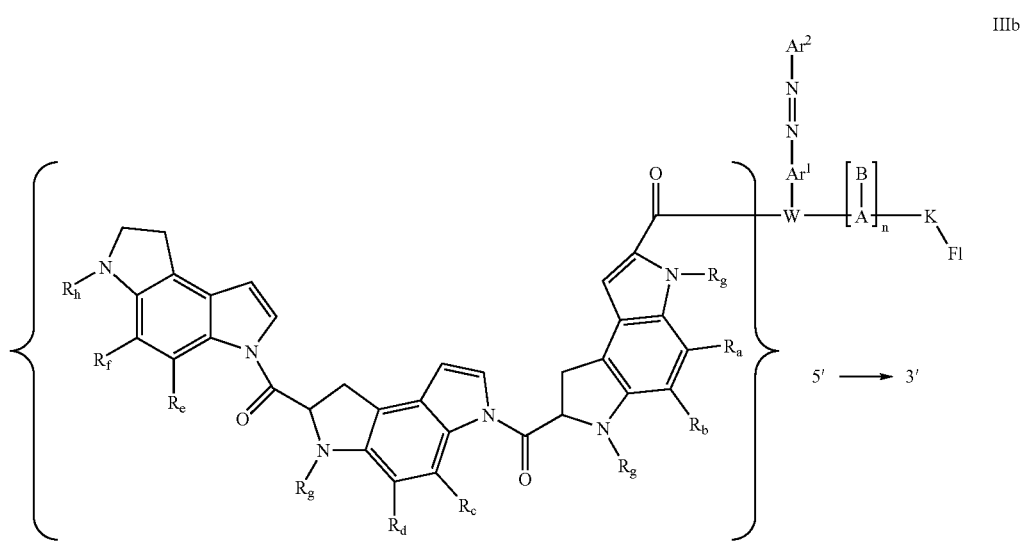

IIIb wherein $Ar^1$, $Ar^2$, W, K, Fl, A, B, and the subscript n have the meanings provided above, and wherein the symbols $R_a$, $R_b$, $R_c$, $R_d$, $R_e$ and $R_f$ represent substituents selected from H, halogen, $(C_1-C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_mOPO_3^{-2}$, and $NHC(O)(CH_2)_mCO_2^-$, and esters and salts thereof, wherein each $R_g$ is independently H or $(C_1-C_8)$alkyl, and the subscript m is an integer of from 0 to 6. The symbol $R_h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences.

In still further preferred embodiments, the oligonucleotide probes/conjugates have the formula:

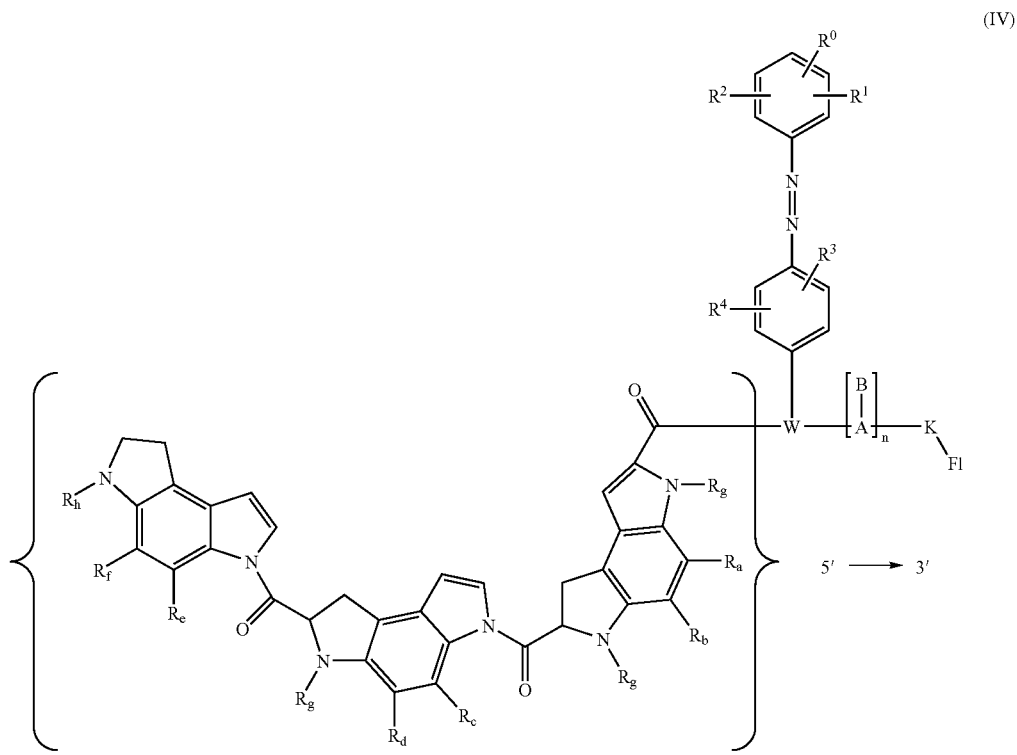

(IV)

wherein W, K, Fl, A, B, and the subscript n have the meanings provided above, and wherein the symbols $R^0$, $R^1$ and $R^2$ represent H or electron-withdrawing groups (wherein electron-withdrawing refers to groups that have greater electronegativity than a hydrogen atom, e.g., nitro, cyano, acetyl and the like) and, the symbols $R^3$ and $R^4$ represent H or electron-donating groups (wherein electron-donating refers to groups that are more electropositive than a hydrogen atom, e.g., alkyl, alkoxy, alkylamino and the like). In a particularly preferred embodiment, W is —(CH$_2$)$_3$N(-)—(CH$_2$)$_3$—; $R^0$=NO$_2$; $R^1$=Cl; $R^2$=$R^3$=$R^4$=H; and K is a (C$_1$-C$_6$)alkylene linker. In one embodiment, M and Fl each can be independently attached at either the 5'- or 3'-end of the probe.

In certain embodiments for each of formulae I, II, IIIa and IIIb, and IV, the linker K is selected to provide particular fluorescence enhancement for the probe/conjugate, and will depend on the length of the oligonucleotide portion of the probe. Accordingly, for probes having 18 or more nucleotides (including modified nucleotides or analogs), K can be a bond or a linking group up to about 20 atoms in length. More preferably, K is a polyalkylene glycol linker or a ribose or deoxy ribose linker (discussed in more detail below). In particularly preferred embodiments, K is a polyalkylene glycol linker such as a polyethylene glycol, polypropylene glycol or polybutylene glycol linker. Most preferred are the polyethylene glycol and functionalized polyethylene glycol linkers that can be obtained from commercial sources.

Other preferred probes or conjugates are those in each of formulae I, II, IIIa and IIIb, and IV wherein the ODN portion is selected to have three or more consecutive guanine bases wherein at least one of the guanine bases is replaced with a modified base, preferably PPG. In other embodiments, the ODN portion is a RNA, a chimera, a PNA or a locked nucleic acid.

Still other preferred probes or conjugates are those in each of formulae I, II, IIIa and IIIb, and IV wherein the ODN portion is selected to be complementary to a target sequence with a polymorphism of interest and at least one additional polymorphism within 20 bases, wherein the additional base or bases involved in the additional polymorphism(s) is substituted with a universal or promiscuous (indiscriminative) base. Still more preferably, the ODN portion is a RNA, a chimera, a PNA or a locked nucleic acid.

Still other preferred probes or conjugates are those in each of formulae I, II, IIIa and IIIb, and IV wherein the ODN portion is selected to be complementary to a target sequence having 30% or more A and T bases, wherein the ODN contains at least one modified base sufficient to provide an increase in stability of the duplex (probe/target hybrid) of at least about 3° C. and a polymorphism of interest and at least one additional polymorphism with in 20 bases, wherein the additional base or bases involved in the additional polymorphism(s) is substituted with a universal or promiscuous (indiscriminative) base. More preferably, the ODN portion is selected to be complementary to a target sequence having 50% or more A and T bases, wherein the ODN contains sufficient modified bases to provide an increase in stability of the duplex (probe/target hybrid) of at least about 5° C. Still more preferably, the ODN portion is a RNA, a chimera, a PNA or a locked nucleic acid.

The probes and conjugates of the present invention are generally prepared using solid phase methods known to those of skill in the art. Assembly can be carried out in either the 5' to 3' direction, or the 3' to 5' direction, using, for example, appropriate phosphoramidite reagents for coupling the ODN monomers, the fluorophores, quenchers and minor groove binders. Other methods for assembly include well known functional group condensations to prepare, for example, ester linkages, amide linkages, disulfide linkages, ether linkages, thioether linkages, and the like. In general, the starting materials are commercially available, or can be prepared in a straightforward manner from commercially available starting materials, using suitable functional group manipulations as described in, for example, March, et al., ADVANCED ORGANIC CHEMISTRY—Reactions, Mechanisms and Structures, 4th ed., John Wiley & Sons, New York, N.Y., (1992).

Returning to the more general provisions for the probes/conjugates of the present invention, the discussion below illustrates the types of oligonucleotides, universal bases, promiscuous (indiscriminative) bases, modified bases, quenching agents or quenchers, minor groove binders, fluorophores and linking groups that can be used herein.

Oligonucleotides and Modified Oligonucleotides

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al. *Science* 254:1497-1500 (1991); bicyclo DNA oligomers (Bolli et al., *Nucleic Acids Res.* 24:4660-4667 (1996)) and related structures. For the conjugates of the present invention, optionally aminor groove binder moiety and/or a quenching agent is attached at the 5' or 3' end of the oligomer and a fluorophore or fluorescent label is attached at the unsubstituted end or in an internal portion of the oligomer.

Preferred in the present invention are DNA oligonucleotides that are single-stranded and have a length of 5-50 nucleotides, more preferably 30 nucleotides or less and most preferably 20 nucleotides or less with a lower limit being approximately 5 nucleotides.

Importantly, the oligonucleotide probes of the present invention contain universal or promiscuous bases at sites of SNPs that are to be masked or rendered "invisible" so the probe can identify the existence of a first polymorphism that is not otherwise masked by the probe.

Universal and Degenerative Bases

Oligonucleotide conjugates containing a fluorophore/quencher pair with an optional minor groove binder will contain at least one universal base and may also comprise one or more modified bases, in addition to the naturally-occurring bases adenine, cytosine, guanine, thymine and uracil.

The most preferred universal bases for use in the present invention include the unsubstituted and substituted pyrazolo pyrimidines that are covalently attached from 2-position on to the polymeric backbone and more specifically the guanine analogue 6-amino-1H-pyrazolo[3,4-d]pyrimidin-4(5H)-one (40), the adenine analogue 4-amino-1H-pyrazolo[3,4-d]pyrimidine (38), as well as 2H-isoquinolin-1-one (25), 6-methyl-2-isoquinoline-1-one (41) and 6,8-dimethylisoquinolin-1(2H)-One (48). The base analogues, when present in an oligonucleotide, improve mismatch discrimination and specifically genotyping. All tautomeric forms of naturally-occurring bases, modified bases and base analogues may be included in the oligonucleotide conjugates of the invention. Other universal bases useful in the present invention include compounds listed in Table 1.

TABLE 1

Universal and Degenerative Bases

Universal and Degenerative Base Structures
ᵃis a degenerative base

1

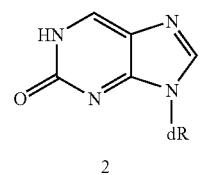

2

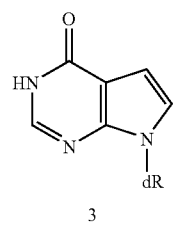

3

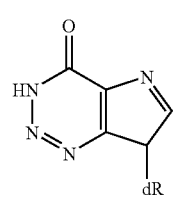

4

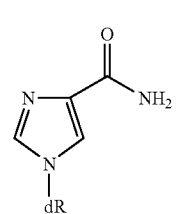

5

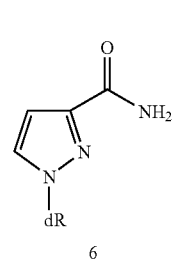

6

TABLE 1-continued

Universal and Degenerative Bases

Universal and Degenerative Base Structures
ᵃis a degenerative base

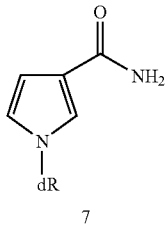

7

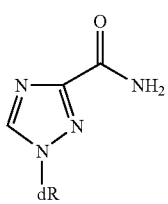

8

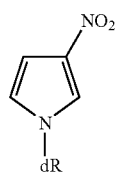

9

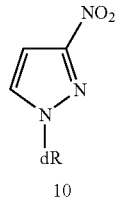

10

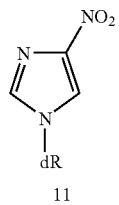

11

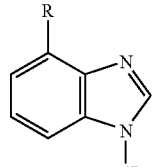

12 (4-NO₂), 13 (5-NO₂), 14 (6-NO₂)

TABLE 1-continued

Universal and Degenerative Bases

Universal and Degenerative Base Structures
ᵃis a degenerative base

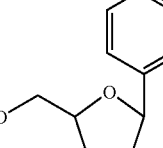

15 (R = NO₂); 16 (R = NH₂)

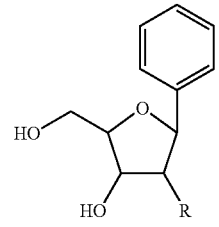

17 (R = OH); 18 (R = H)

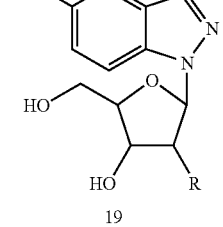

19

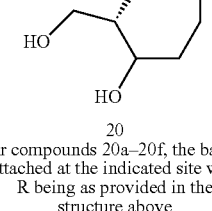

20
For compounds 20a–20f, the base is
attached at the indicated site with
R being as provided in the
structure above

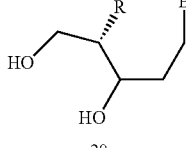

20a (R = H); 20b (R = OMe)

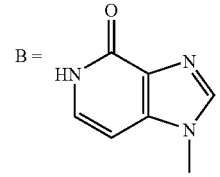

20c (R = H); 20d (R = OMe)

TABLE 1-continued
Universal and Degenerative Bases
Universal and Degenerative Base Structures
[a] is a degenerative base
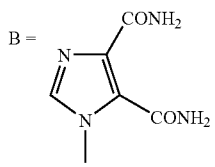
20e (R = OMe)
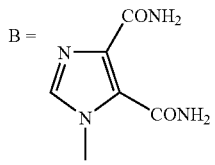
20f (R = OMe)
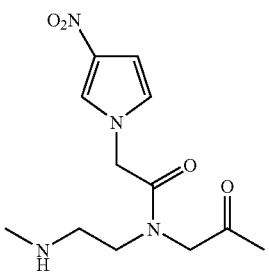
21
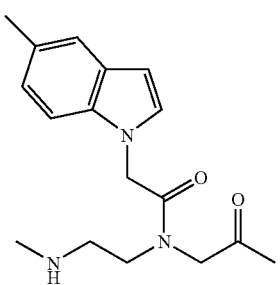
22
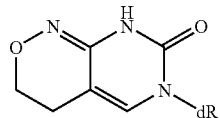
23[a]
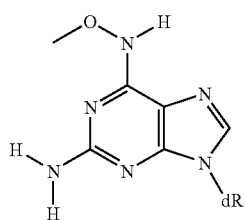
24[a]
TABLE 1-continued
Universal and Degenerative Bases
Universal and Degenerative Base Structures
[a] is a degenerative base
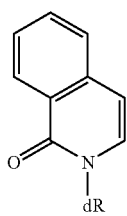
25
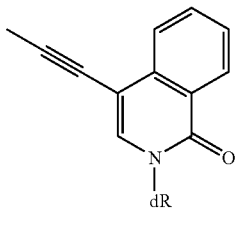
26
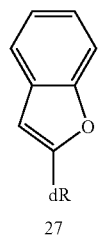
27
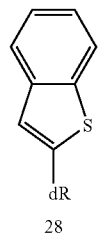
28
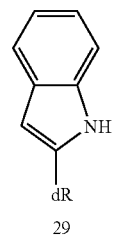
29
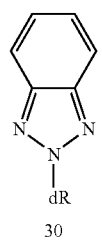
30

TABLE 1-continued
Universal and Degenerative Bases
Universal and Degenerative Base Structures
ᵃis a degenerative base
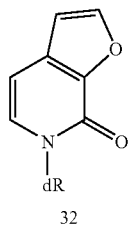
32
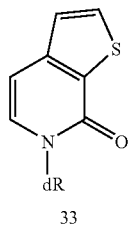
33
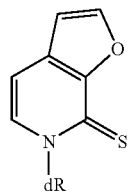
34
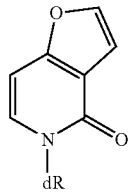
35
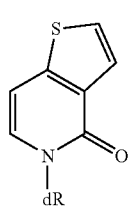
36
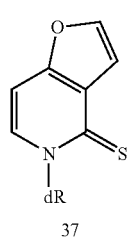
37
TABLE 1-continued
Universal and Degenerative Bases
Universal and Degenerative Base Structures
ᵃis a degenerative base
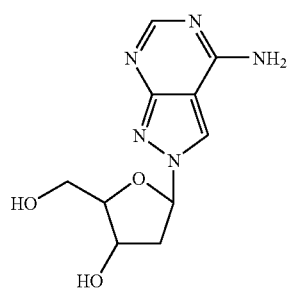
38
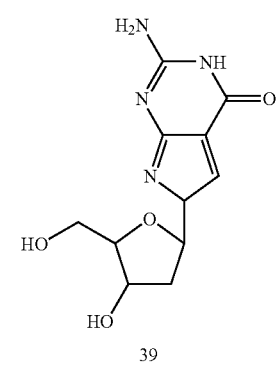
39
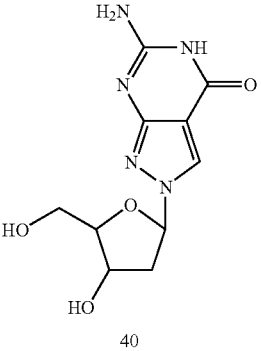
40
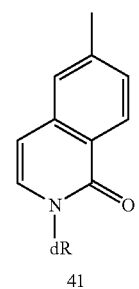
41

TABLE 1-continued

Universal and Degenerative Bases

Universal and Degenerative Base Structures
<sup>a</sup>is a degenerative base

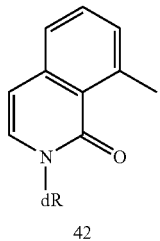

42

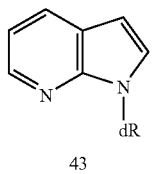

43

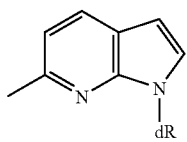

44

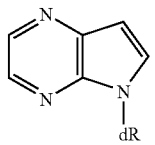

45

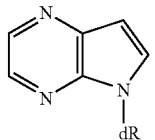

46

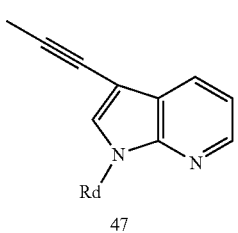

47

TABLE 1-continued

Universal and Degenerative Bases

Universal and Degenerative Base Structures
<sup>a</sup>is a degenerative base

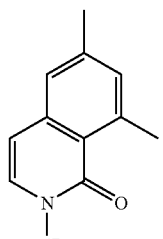

48

Promiscuous (Indiscriminative) Bases

The most preferred promiscuous (indiscriminative) bases for use in the present invention include the unsubstituted and substituted pyrazolo pyrimidines that are covalently attached from the 1-position on to the polymeric backbone and more specifically guanine analogue 6-amino-1H-pyrazolo[3,4-d]pyrimidin-4(5H)-one (49), substituted 6-amino-1H-pyrazolo[3,4-d]pyrimidin-4(5H)-one analogs, 1H-pyrazolo[3,4-d]pyrimidine-4,6-diamine (50) and substituted 1H-pyrazolo[3,4-d]pyrimidine-4,6-diamine analogs. Other promiscuous (indiscriminative) bases useful in the present invention include compounds listed in Table 2.

TABLE 2

Promiscuous (indiscriminative) Bases

Promiscuous (indiscriminative) Base Structures

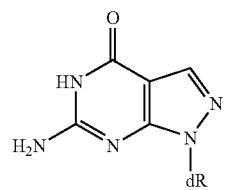

49

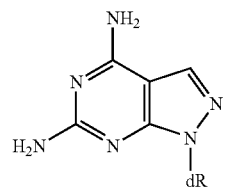

50

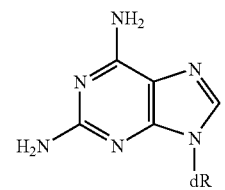

51

TABLE 2-continued

Promiscuous (indiscriminative) Bases

Promiscuous (indiscriminative) Base Structures

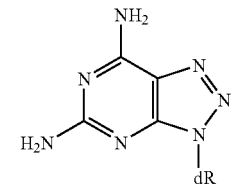

52

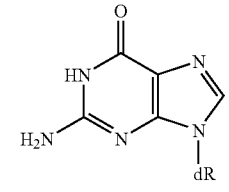

53

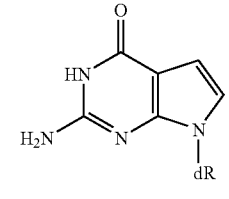

54

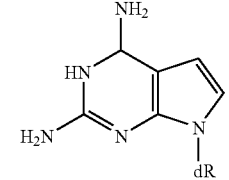

55

In another embodiment, universal and promiscuous (indiscriminative) bases based on the structures are contemplated. One or more substituents may be introduced in each of the ring structures that may include $(C_1-C_{12})$alkyl, $(C_2-C_{12})$alkenyl, $(C_2-C_{12})$alkynyl, $(C_2-C_{12})$heteroalkyl, $(C_3-C_{12})$heteroalkenyl, $(C_3-C_{12})$heteroalkynyl, —O—$(C_1-C_{12})$alkyl, —O—$(C_2-C_{12})$alkenyl, —O—$(C_2-C_{12})$alkynyl, —S—$(C_1-C_{12})$alkyl, —S—$(C_2-C_{12})$alkenyl, —S—$(C_2-C_{12})$alkynyl, heterocyclyl$(C_1-C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, aryl, heterocyclyl, halogen, —CN, and —CONH$_2$, and further including those substituents wherein the aliphatic portions (e.g., alkyl, alkenyl and alkynyl portions) are further substituted with one or two hydroxy, amino or halogen groups. The universal base can be synthesized by methods known in the art (Loakes, *Nucl. Acids Res.*, 29:2437-2447 (2001); Wu et al, *J. Am. Chem. Soc.*, 22:7621-7632 (2000) and Seela et al, *Nucl. Acids Res.*, 28:3224-3232 (2001). The promiscuous (indiscriminative) bases can be synthesized by known methods (see published applications WO 01/64958; WO 03/022859; and EP 0624161).

In one group of preferred embodiments, the pyrazolopyrimidine promiscuous (indiscriminative) bases have the formula

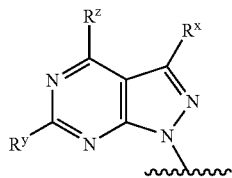

V wherein $R^y$ and $R^z$ are independently selected from the group consisting of OH and NH$_2$ and at least one of $R^y$ or $R^z$ is NH$_2$; and $R^x$ is a member selected from the group consisting of H, $(C_1-C_{12})$alkyl, $(C_2-C_{12})$alkenyl, $(C_2-C_{12})$alkynyl, $(C_2-C_{12})$heteroalkyl, $(C_3-C_{12})$heteroalkenyl, $(C_3-C_{12})$heteroalkynyl, —O—$(C_1-C_{12})$alkyl, —O—$(C_2-C_{12})$alkenyl, —O—$(C_2-C_{12})$alkynyl, —S—$(C_1-C_{12})$alkyl, —S—$(C_2-C_{12})$alkenyl, —S—$(C_2-C_{12})$alkynyl, heterocyclyl$(C_1C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, aryl, heterocyclyl, halogen, —CN and —CONH$_2$, and further include those $R^x$ groups wherein the aliphatic portions (e.g., alkyl, alkenyl and alkynyl portions) are further substituted with one or two hydroxy, amino or halogen groups. The wavy line indicates the point of attachment to the remainder of the probe.

In another group of embodiments one of more of carbon atoms of the basic ring structures of 49 and 50 is substituted by N. The synthesis of these compounds have been disclosed in the art (see, for example, Sugiyama et al, *Chem. Europ. J*, 6:369-378 (2000); and Hutzenlaub, et al., *J. Med. Chem.*, 15:879-883 (1972)).

Modified Bases

Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7-deazapurines and their derivatives and pyrazolopyrimidines (described in PCT WO 90/14353 and in U.S. Pat. No. 6,127,121, both of which are hereby incorporated herein by reference).

A variety of modified bases can be used in the present invention, for replacing normal bases. Benefits of the modified bases have been described elsewhere. Importantly, the modified bases can be used at positions that are not at sites of SNPs. However, the complete list of modified bases includes some bases that are also characterized as universal or promiscuous bases. Accordingly, the present invention provides that probes will have universal bases or promiscuous bases at SNP sites to be masked or rendered invisible, but may optionally have modified bases at other sites in the probe. The most preferred modified bases for use in the present invention include the guanine analogue 6-amino-1H-pyrazolo[3,4-d]pyrimidin-4(5H)-one (ppG or PPG, also Super G), the adenine analogue 4-amino-1H-pyrazolo[3,4-d]pyrimidine (ppA or PPA) and 3H-[1,2,3]triazolo[4,5-d]pyrimidine-5,7-diamine ((NH$_2$)$_2$PPA). The xanthine analogue 1H-pyrazolo[5,4-d]pyrimidin-4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the invention. Other modified bases useful in the present invention include 6-amino-3-prop-1-ynyl-5-hydropyrazolo[3,4-d]pyrimidine-4-one, PPPG; 6-amino-3-(3-hydroxyprop-1-yny)1-5-hydropyrazolo[3,4-d]pyrimidine-4-one, HOPPPG; 6-amino-3-(3-aminoprop-1-ynyl)-5-hydropyrazolo[3,4-d]pyrimidine-4-one, $NH_2PPPG$; 4-amino-3-(prop-1-ynyl)pyrazolo[3,4-d]pyrimidine, PPPA; 4-amino-3-(3-hydroxyprop-1-ynyl) pyrazolo[3,4-d]pyrimidine, HOPPPA; 4-amino-3-(3-aminoprop-1-ynyl)pyrazolo[3,4-d]pyrimidine, $NH_2PPPA$; 3-prop-1-ynylpyrazolo[3,4-d]pyrimidine-4,6-diamino, $(NH_2)_2PPPA$; 2-(4,6-diaminopyrazolo[3,4-d]pyrimidin-3-yl)ethyn-1-ol, $(NH_2)_2PPPAOH$; 3-(2-aminoethynyl)pyrazolo[3,4-d]pyrimidine-4,6-diamine, $(NH_2)_2PPPANH_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, $NH_2PC$; 5-[4-amino-3-(3-methoxyprop-1-ynyl)pyrazol[3,4-d]pyrinidinyl]-2-(hydroxymethyl)oxolan-3-ol, $CH_3OPPPA$; 6-amino-1-[4-hydroxy-5-(hydroxymethyl)oxolan-2-yl]-3-(3-methoxyprop-1-ynyl)-5-hydropyrazolo[3,4-d]pyrimidin-4-one, $CH_3OPPPG$; 4-(4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo[3,4-d]pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine $((NH_2)_2PPAI)$; 3-bromo-1H-pyrazolo[3,4-d]pyrimidine-4,6-diamine $((NH_2)_2PPABr)$; 3-chloro-1H-pyrazolo[3,4-d]pyrimidine-4,6-diamine $((NH_2)_2PPACl)$; 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

In addition to the modified bases noted above, the oligonucleotides can have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196, which is hereby incorporated herein by reference. Oligonucleotides containing 2',3'-dideoxy-3'-aminoribofuranosides are described in Chen et al. *Nucleic Acids Res.* 23:2661-2668 (1995). Synthetic procedures for locked nucleic acids (Singh et al, *Chem. Comm.,* 455-456 (1998); Wengel J., *Acc. Chem. Res.,* 32:301-310 (1998)) and oligonucleotides containing 2'-halogen-2'-deoxyribofuranosides (Palissa et al., *Z. Chem* 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., *Nucl. Acids Res.,* 23:2662-2668 (1995)). Combinations of oligonucleotide linkages are also within the scope of the present invention. Still other backbone modifications are known to those of skill in the art.

In one group of embodiments, the pyrazolopyrimidines are substituted from the 2-position instead (compounds 38-40) of the usual 3-position to the polymeric backbone.

In another group of embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. *Science* 254:1497-1500 (1991). PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855, each of which is hereby incorporated herein by reference. Alternate approaches to PNA and DNA/PNA chimera synthesis and monomers for PNA synthesis have been summarized. Uhlmann et al. *Angew. Chem. Int. Ed.* 37:2796-2823 (1998). Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal and promiscuous (indiscriminative) bases, sugar modification, backbone modification or a minor groove binder to balance the $T_m$ of a DNA, PNA or DNA/PNA chimera is in the scope of this invention. The synthetic methods necessary for the synthesis of modified base monomeric units required for nucleic acid, PNA and PNA/DNA chimeras synthesis are available in the art, see methods in this application and Uhlmann et al. *Angew. Chem. Int. Ed.* 37:2796-2823 (1998).

For the uses described herein, and as noted above, the oligonucleotides and modified oligonucleotides will preferably have from 5 to 100 bases, more typically from 5 to 50 or 5 to 30 bases, and usually from 5 to 20 bases. In some embodiments, the oligonucleotide portions of the probes/conjugates will have 5 to 15 bases. In some embodiments, the oligonucleotide portions will have in addition to one or more universal or promiscuous (indiscriminative) base, one or more modified base. In some embodiments, the oligonucleotides will have 6, 7, 8, 9, 10, 11, 12, 13, 14, 15, 16, 17, 18, 19 or 20 bases or modified bases that include at least one universal or promiscuous (indiscriminative) base at a site designed to "mask" a SNP.

The ability to design probes and primers in a predictable manner using an algorithm, that can direct the use or incorporation of universal or promiscuous (indiscriminative) base, modified bases, minor groove binders, fluorophores and/or quenchers, based on their thermodynamic properties have been described in co-pending application Ser. No. 10/032,307, filed Dec. 21, 2001, which is hereby incorporated herein by reference. Accordingly, the use of any combination of normal bases, unsubstituted pyrazolo[3,4-d] pyrimidine bases (e.g., PPG and PPA), 3-substituted pyrazolo[3,4-d]pyrimidines, modified purine, modified pyrimidine, 5-substituted pyrimidines, universal bases, promiscuous (indiscriminative) bases, sugar modification, backbone modification or a minor groove binder to balance the T$_m$ (e.g., within about 5-8° C.) of a hybridized product with a nucleic acid, PNA or DNA/PNA chimera is contemplated by the present invention. Moreover, the use of promiscuous bases or universal bases in primers will facilitate the application of each of the methods described herein for universal amplification with variable sequences (e.g., HIV mutations, closely related species, and the like). Additionally, the use of labeled primers directly or indirectly through ligands such as biotin to detect nucleic acid targets is well known in the art. Additionally, Scorpion primers are useful to detect mutations, even in the absence of probes (see, Thelwell, et al., *Nucl. Acids. Res.*, 28:3752-3761 (2000)).

New Universal Bases

A number of new universal bases can be prepared as outlined in Reaction Scheme 1, using synthetic methods known in the art. In Reaction Scheme 1, Tol is a p-tolyl group, DMT is a dimethoxytrityl group, CEP is cyanoethyl-diisopropylphosphoramidite group and R is —(CH$_2$)$_n$X where X is H, NH$_2$, OH, CN and n is an integer of from 1 to 6.

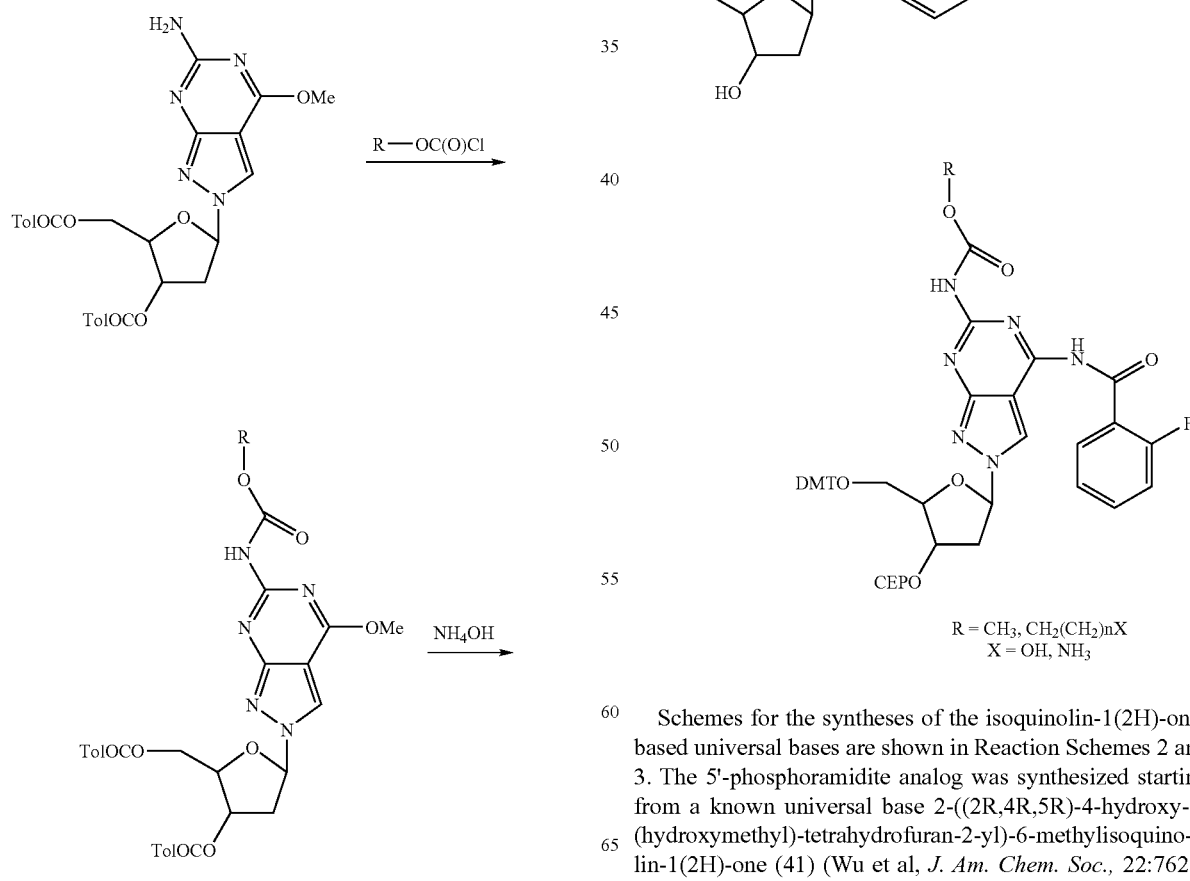

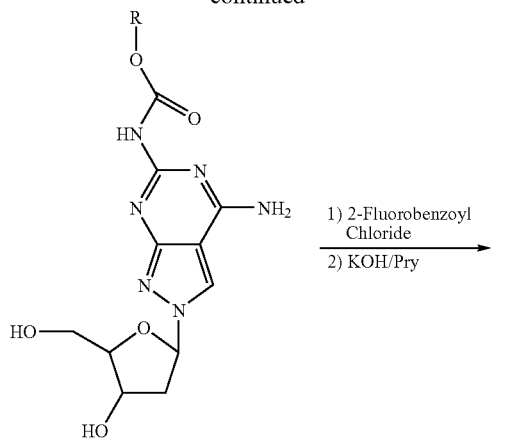

Schemes for the syntheses of the isoquinolin-1(2H)-one-based universal bases are shown in Reaction Schemes 2 and 3. The 5'-phosphoramidite analog was synthesized starting from a known universal base 2-((2R,4R,5R)-4-hydroxy-5-(hydroxymethyl)-tetrahydrofuran-2-yl)-6-methylisoquinolin-1(2H)-one (41) (Wu et al, *J. Am. Chem. Soc.*, 22:7621-7632 (2000)) by a reaction first with dimethylthexylsilyl chloride, followed by dimethoxytrityl chloride to yield the 3'-dimethoxyltrityl derivative (55). The reaction of 55 with 2-cyanoethyl tetraisopropylphosphorodiamidite(CEIPDA) in CH$_2$Cl$_2$ yielded the desired blocked 5'-phosphoramidte (56) as shown in Reaction Scheme 2.

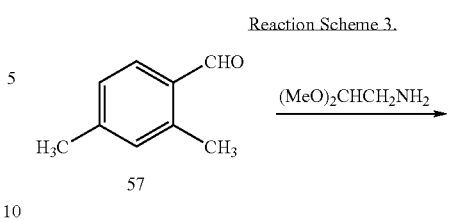

Reaction Scheme 3.

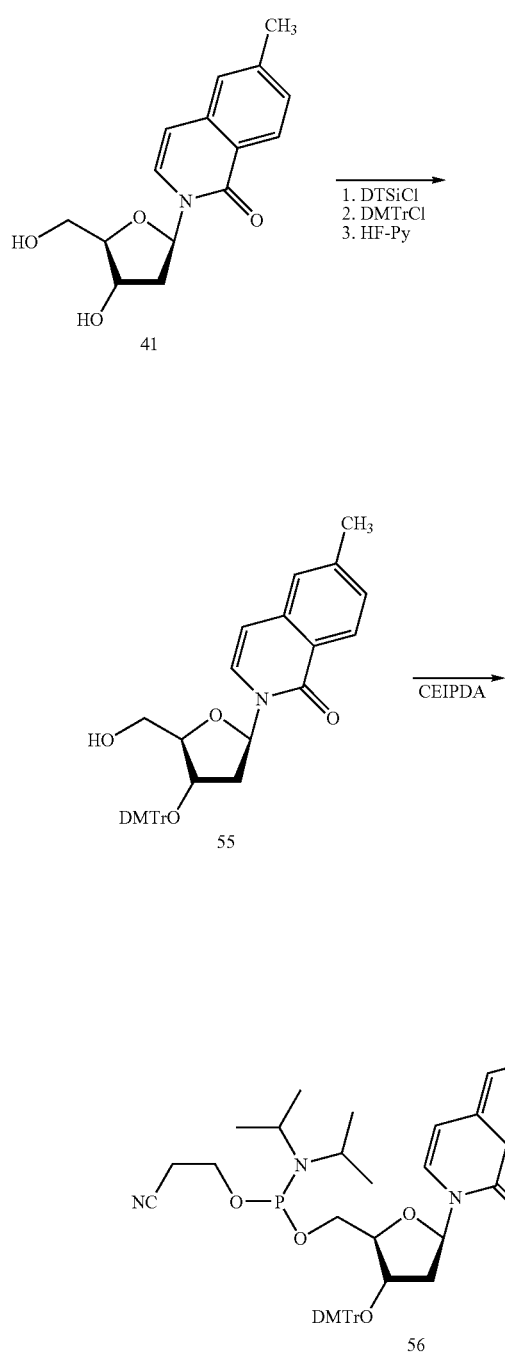

The synthesis of a new universal base phosphoramidite (65), an analog of 48, is shown in Reaction Scheme 3.

-continued

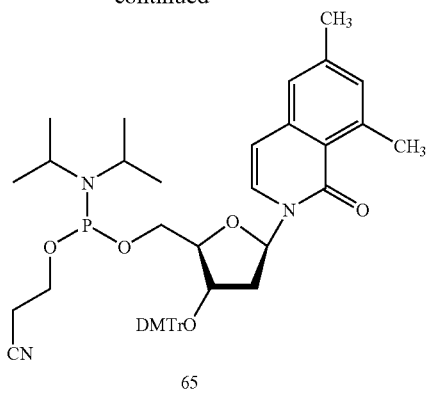

65

2,4-Dimethylbenzaldehyde (57) was reacted with 2,2-dimethoxyethylamine to yield the imine (58), followed by acid treatment to yield 6,8-dimethylisoquinoline (59). Oxidation with m-chloro-peroxybenzoic acid gave N-oxide (60), which was treated subsequently with acetic anhydride and aqueous NaOH to give 6,8-dimethylisoquinolin-1(2H)-one (61). Glycosylation of (61) with chloro-sugar (62) and following deprotection gave the nucleoside (63). The 3'-dimethoxytrityl protected nucleoside (64) was prepared next from (63), and converted to 5'phosphoramidite (65) by standard procedures.

In another embodiment using methods known in the art, the nucleoside analog (63) can be converted to the 3'-phosphoramidite analog.

Minor Groove Binders

Minor groove binder oligonucleotide conjugates (or "probes") are described in U.S. Pat. No. 6,312,894, which is hereby incorporated herein by reference. These conjugates form hyper-stabilized duplexes with complementary DNA. In particular, sequence specificity of short minor groove binder probes is excellent for high temperature applications such as PCR. Quite surprisingly, probes containing a minor groove binding-quencher compound at the 5'-end and a fluorophore at the 3'-end are particularly useful for assay methods using fluorogenic 2'-deoxynucleotides U.S. patent application Ser. No. 10/165,410, which is hereby incorporated herein by reference. These probes fluoresce upon hybridization to the complementary target. The 5'-MGB-quencher group has now been found to prevent 5'-nuclease digestion by Taq polymerase during homogeneous amplification. Moreover, the 5'-MGB-quencher-oligonucleotide-fluorophore (5'-MGB-Q-ODN-Fl) probes described herein display a dynamic range of 7 orders of magnitude, with an ultimate sensitivity of better than 5 copies per sample in real-time PCR amplification reactions.

The probes/conjugates of the present invention will also optionally have a covalently attached minor groove binder. A variety of suitable minor groove binders have been described in the literature. See, for example, Kutyavin, et al. U.S. Pat. No. 5,801,155, which is hereby incorporated herein by reference; Wemmer, D. E., and Dervan P. B., *Current Opinon in Structural Biology*, 7:355-361 (1997); Walker, W. L., Kopka, J. L. and Goodsell, D. S., *Biopolymers*, 44:323-334 (1997); Zimmer, C & Wahnert, U. *Prog. Biophys. Molec. Bio.* 47:31-112 (1986) and Reddy, B. S. P., Dondhi, S. M., and Lown, J. W., *Pharmacol. Therap.*, 84:1-111 (1999).

The minor groove binder-quencher-oligonucleotide-fluorophore conjugates of the present invention can be in a linear arrangement (as suggested by the formula 5'-M-Q-ODN-Fl-3') or in a branched arrangement wherein the quencher (Q) and the minor groove binder (M) are attached to a linking group that serves to join ODN, Q and M. Additionally, the quencher can be attached at the distal (relative to attachment to ODN) terminus of the minor groove binder (e.g., 5'-Q-M-ODN-Fl). Each of the arrangements are meant to be included when the linear abbreviation (M-Q-ODN-Fl) is used. Additionally, the MGB and Q portions each can be attached at either the 3' or 5' end of the oligonucleotide, or an internal position of the oligonucleotide, so long as such attachment does not interfere with the quenching mechanisms of the conjugate. Generally, this can be accomplished through the use of a suitable linking group (U.S. patent application Ser. No. 10/165,410, which is hereby incorporated herein by reference).

Suitable methods for attaching minor groove binders (as well as reporter groups such as fluorophores and quenchers described below) through linkers to oligonucleotides are described in, for example, U.S. Pat. Nos. 5,512,677; 5,419,966; 5,696,251; 5,585,481; 5,942,610 and 5,736,626, each of which is hereby incorporated herein by reference.

The minor groove binder is generally attached to the 3' or 5' position of the oligonucleotide portion via a suitable linking group. Attachment at the 5' end provides both a benefit of hybrid stability, since melting of an oligonucleotide duplex begins at the termini, but also reduces and/or prevents nuclease digestion of the probe during amplification reactions.

The location of a minor groove binder within a minor groove binder-oligonucleotide conjugate can also affect the discriminatory properties of such a conjugate. An unpaired region within a duplex will result in changes in the shape of the minor groove in the vicinity of the mispaired base(s). Since minor groove binders fit best within the minor groove of a perfectly-matched DNA duplex, mismatches resulting in shape changes in the minor groove would reduce binding strength of a minor groove binder to a region containing a mismatch. Hence, the ability of a minor groove binder to stabilize such a hybrid would be decreased, thereby increasing the ability of a minor groove binder-oligonucleotide conjugate to discriminate a mismatch from a perfectly-matched duplex. On the other hand, if a mismatch lies outside of the region complementary to a minor groove binder-oligonucleotide conjugate, discriminatory ability for unconjugated and minor groove binder-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of minor groove binder-oligonucleotides conjugates in this context lies in the fact that much shorter oligonucleotides compared to those used in the prior art (i.e., 20-mers or shorter), having greater discriminatory powers, can be used, due to the pronounced stabilizing effect of minor groove binder conjugation.

In one group of embodiments, the minor groove binder is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepines and analogs.

Further preferred minor groove binders are those selected from the formulae:

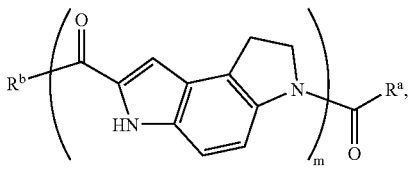

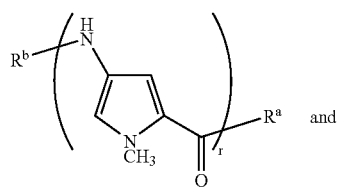

and

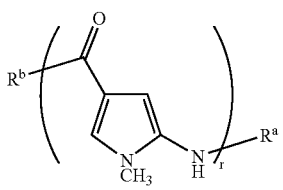

the subscript m is an integer of from 2 to 5; the subscript r is an integer of from 2 to 10; and each $R^a$ and $R^b$ is independently a linking group to the oligonucleotide (either directly or indirectly through a quencher), H, —$OR^c$, —$NR^c R^d$, —$COOR^c$ or —$CONR^c R^d$, wherein each $R^c$ and $R^d$ is selected from H, ($C_2$-$C_{12}$)heteroalkyl, ($C_3$-$C_{12}$)heteroalkenyl, ($C_3$-$C_{12}$)heteroalkynyl, ($C_1$-$C_{12}$)alkyl, ($C_2$-$C_{12}$)alkenyl, ($C_2$-$C_{12}$)alkynyl, aryl($C_1$-$C_{12}$)alkyl and aryl, with the proviso that one of $R^a$ and $R^b$ represents a linking group to ODN or Q. In an additional embodiment each of the rings in each structure can contain one or more additional substitutions selected from H, halogen, ($C_1$-$C_8$)alkyl, $OR_g$, $N(R_g)_2$, $N^+(R_g)_3$, $SR_g$, $COR_g$, $CO_2R_g$, $CON(R_g)_2$, $(CH_2)_m SO_3^-$, $(CH_2)_m CO_2^-$, $(CH_2)_m OPO_3^{-2}$, and $NHC(O)(CH_2)_m CO_2^-$, and esters and salts thereof, wherein each $R_g$ is independently H or ($C_1$-$C_8$)alkyl, and the subscript m is an integer of from 0 to 6. The symbol $R_h$ represents H or a group (typically the vestige of a linking group used in solid phase synthesis) having from 1-30 atoms selected from C, N, O, P, and S which is either cyclic, acyclic, or a combination thereof, and having additional hydrogen atoms to fill the available valences.

Particularly preferred minor groove binders include the trimer of 3-carbamoyl-1,2-dihydro-(3H)-pyrrolo[3,2-e]indole-7-carboxylate ($CDPI_3$) or a substituted dihydrocyclopyrroloindole triamide ($DPI_3$), the pentamer of N-methylpyrrole-4-carbox-2-amide ($MPC_5$) and other minor groove binders that exhibit increased mismatch discrimination. Additional minor groove binder moieties that will find use in the practice of the present invention are disclosed in co-owned U.S. Pat. No. 5,801,155, hereby incorporated herein by reference. In certain embodiments, the minor groove binders can have attached water solubility-enhancing groups (e.g., sugars, amino acids, carboxylic acid or sulfonic acid substituents, and the like). See U.S. patent application Ser. Nos. 09/693,213 and 10/302,607, both of which are hereby incorporated herein by reference.

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_o$) is described as the distance between the donor and acceptor molecules where the energy transfer is 50% efficient. Other mechanisms of fluorescence quenching are also known, such as, collisional and charge transfer quenching. There is extensive guidance in the art for selecting quencher and fluorophore pairs and their attachment to oligonucleotides (Haugland, R. P., HANDBOOK OF FLUORESCENT PROBES AND RESEARCH CHEMICALS, Ninth Edition, Molecular Probes, Eugene, Oreg., 2002, also Web Edition at www.probes.com/handbook; U.S. Pat. Nos. 3,996,345 and 4,351,760, each of which is hereby incorporated herein by reference). Preferred quenchers are described in co-owned U.S. Ser. No. 09/457,616 (filed Dec. 8, 1999), and which is hereby incorporated herein by reference. More particularly, Table 3 below contains structures of quenchers that can be readily modified to structures having suitable functional groups (e.g., Q-W with attachment sites for ODN and minor groove binder portions) for introduction into probes, based on the known chemical reactions cited (see, for example, Thiel, et al., *J. fur prakt. Chemie*, 328:497-514 (1986); U.S. Pat. Nos. 4,324,721 and 4,054,560; Timm, *Melliand Textilberichte*, 9:1090-1096 (1969); Hallas, *J.S.D.C.* 285-294 (1979); Beyer, et al., *J Prakt. Chem.*, 24:100-104 (1964); Hutchings, et al., *Chem. Europ. J.* 3:1719-1727 (1997) and Morley, et al., *J. Phys. Chem. A.*, 102:5802-5808 (1998); Haak, et al., *J. Chem. Res. Miniprint* 10:2701-2735 (1998) and Ruggli et al., *Helv. Chim. Acta*, 26:814-826 (1943). See also co-owned pending applications U.S. 2003/0096254 and U.S. 2002/0155484, each of which is hereby incorporated herein by reference). Additional structures (e.g., mono- and bis-azo dyes) with different combinations of substituents at various positions can be prepared based on compounds and methods known in the dye chemistry field (summarized in the Color Index, Issue 3 on CDD-ROM, pages 4009-4324; Society of Dyers and Colourists, Bradford, England; www.s-dc.org.uk; and see also WO 01/86001).

TABLE 3

| Structure Literature | $\lambda_{max}$ nm; $\epsilon$ M$^{-1}$cm$^{-1}$; Solvent | Linker-Modified Structure Q—W |
|---|---|---|
| (allyl-methyl-amino-phenyl)-azo-(cyano-nitro-benzylidene) structure | 464 | bis(hydroxyethyl)amino-phenyl-azo-phenyl-CH=CH-(cyano-nitro-nitro-phenyl) structure |
| phenyl-azo-(nitrophenyl-phenyl) structure | 440 | bis(hydroxyethyl)amino-phenyl-azo-biphenyl-nitro structure |
| diethylamino-phenyl-azo-(nitro-nitrophenyl) structure | 540; 40,000 MeOH | bis(hydroxyethyl)amino-phenyl-azo-(nitro-nitrophenyl) structure |
| diethylamino-phenyl-azo-(nitro-bromo-nitrophenyl) structure | 549; 37,000 EtOH | bis(hydroxyethyl)amino-phenyl-azo-(nitro-nitrophenyl) structure |
| diethylamino-phenyl-azo-(nitro-cyano-nitrophenyl) structure | 590; 48,978 CHCl$_3$ | bis(hydroxyethyl)amino-phenyl-azo-(nitro-cyano-nitrophenyl) structure |

TABLE 3-continued

| Structure Literature | $\lambda_{max}$ nm; $\epsilon$ M$^{-1}$cm$^{-1}$; Solvent | Linker-Modified Structure Q—W |
|---|---|---|
| | 601 40,738 CHCl$_3$ | |
| | 623 48,000 CHCl$_3$ | |
| | 656 100,000 CHCl$_3$ | |
| | 656 53,043 | |

TABLE 3-continued

| Structure Literature | λ_max nm; ε M$^{-1}$cm$^{-1}$; Solvent | Linker-Modified Structure Q—W |
|---|---|---|
| [structure: 5-nitro-benzisothiazole-azo-N,N-dimethylaniline] | 598 | [structure: 5-nitro-benzisothiazole-azo-N,N-bis(2-hydroxyethyl)aniline] |
| [structure: 3-nitro-5-acetyl-thiophene-azo-N,N-dimethylaniline] | 582 | [structure: 3-nitro-5-acetyl-thiophene-azo-N,N-bis(2-hydroxyethyl)aniline] |
| [structure: 3-nitro-5-acetyl-thiophene-azo-(2-methoxy-5-acetamido)-N,N-bis(2-hydroxyethyl)aniline] | 652 | [structure: 3-nitro-5-acetyl-thiophene-azo-(2-methoxy-5-acetamido)-N-(2-carboxyethyl)-N-(2-hydroxyethyl)aniline] |
| [structure: 4-nitrophenyl-azo-5-(N,N-dimethylamino)thiophene] | 554, 50,000 | [structure: 4-nitrophenyl-azo-5-(N,N-bis(2-hydroxyethyl)amino)thiophene] |

TABLE 3-continued

| Structure Literature | $\lambda_{max}$, nm; $\epsilon$ $M^{-1}cm^{-1}$; Solvent | Linker-Modified Structure Q—W |
|---|---|---|
| | 673.5 | |
| | 809 | |
| | 592 46,000 | |
| | 601 51,000 | |
| | 623 48,000 | |

TABLE 3-continued
| Structure Literature | $\lambda_{max}$ nm; $\epsilon$ $M^{-1}cm^{-1}$; Solvent | Linker-Modified Structure |
|---|---|---|
| 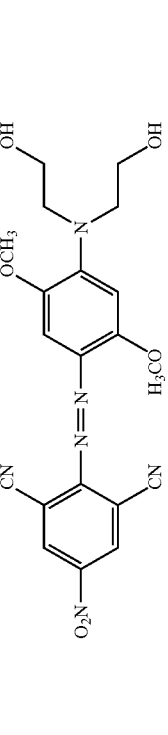 | 632 Predicted | 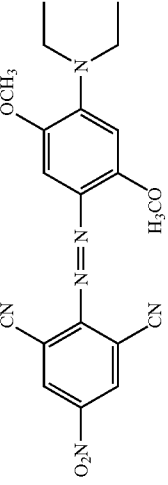 |

The quenchers above cover the range from about 400-800 nm, and many demonstrate improved quenching when attached to a MGB. While the modified versions illustrate —N(CH$_2$CH$_2$OH)$_2$ as a preferred linking group to be used to couple the quencher to oligonucleotides, minor groove binder or solid support, examples of other suitable linkers are known in the art or are provided herein.

Preferred quenchers for each of the aspects of the invention herein are selected from those in Table 3, as well as bis azo quenchers, including those from Biosearch Technologies, Inc. (provided as Black Hole™ Quenchers: BH-1, BH-2 and BH-3), Dabcyl, TAMRA and carboxytetramethyl rhodamine.

Fluorophores

Fluorophores useful in the present invention are generally fluorescent organic dyes that have been derivatized for attachment to the terminal 5' carbon of the oligonucleotide probe, preferably via a linking group. One of skill in the art will appreciate that suitable fluorophores are selected in combination with a quencher which is typically also an organic dye, which may or may not be fluorescent.

There is a great deal of practical guidance available in the literature for selecting appropriate fluorophore-quencher pairs for particular probes. See, for example, Clegg (cited above); Wu et al. (cited above); Pesce et al., editors, FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic (quenching) molecules and their relevant optical properties for choosing fluorophore-quencher pairs, e.g., Berlman, HANDBOOK OF FLUORESCENCE SPECTRA OF AROMATIC MOLECULES, 2ND EDITION (Academic Press, New York, 1971); Griffiths, COLOUR AND CONSTITUTION OF ORGANIC MOLECULES (Academic Press, New York, 1976); Bishop, editor, INDICATORS (Pergamon Press, Oxford, 1972); Haugland, HANDBOOK OF FLUORESCENT PROBES AND RESEARCH CHEMICALS (Ninth Edition, Molecular Probes, Eugene, Oreg., 2002, also Web Edition at www.probes.com/handbook); Pringsheim, FLUORESCENCE AND PHOSPHORESCENCE (Interscience Publishers, New York, 1949); and the like. Additionlly, methods for derivatizing fluorophores and quenchers for covalent attachment via common reactive groups are also well known. See, for example, Haugland (cited above); Ullman et al., U.S. Pat. No. 3,996,345; Khanna et al., U.S. Pat. No. 4,351,760; each of which is hereby incorporated herein by reference.

Preferred fluorophores are those based on xanthene dyes, a variety of which are available commercially with substituents useful for attachment of either a linking group or for direct attachment to an oligonucleotide. Another group of fluorescent compounds are the naphthylamines, having an amino group in the α- or β-position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. Still other suitable fluorophores include the resorufin dyes, rhodamine dyes, cyanine dyes and BODIPY dyes.

These dyes and appropriate linking methodologies for attachment to oligonucleotides are described in many references, e.g., Khanna et al. (supra); Marshall, *Histochemical J.*, 7:299-303 (1975); Menchen et al., U.S. Pat. No. 5,188,934; Menchen et al., European Patent Application 87310256.0; and Bergot et al., International Application PCT/US90/05565.

More particularly, the fluorophores described herein can be attached to the oligonucleotide portions using, for example, chemical or enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. Nos. 5,824,796; 5,210,015; Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; and Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774-1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767, hereby incorporated herein by reference. Examples of modifying enzymes include, but are not limited to, DNA polymerases, reverse transcriptases, RNA polymerases, etc. Examples of enzymes which are able to add a label to an already-existing oligonucleotide include, but are not limited to, kinases, terminal transferases, ligases, glycosylases, etc.

For each of the aspects of the present invention, preferred fluorophores are selected from cyanines, xanthenes, BODIPY analogs, 5-FAM™, 6-FAM™, TET™, JOE™, HEX™, VIC™, NED™, TAMRA™, ROX™, Bothell Blue™ and Yakima Yellow™ (YY). These fluorophores are generally available from commercial sources such as Applied Biosystems Inc., Foster City, Calif. and Epoch Biosciences, Inc., Bothell, Wash.

Linking Groups

A variety of linking groups and methods are known to those of skill in the art for attaching fluorophores, quenchers and minor groove binders to the 5' or 3' termini of oligonucleotides. See, for example, Eckstein, editor, OLIGONUCLEOTIDES AND ANALOGUES: A PRACTICAL APPROACH (IRL Press, Oxford, 1991); Zuckerman et al., *Nucleic Acids Research*, 15:5305-5321 (1987); Sharma et al., *Nucleic Acids Research*, 19:3019 (1991); Giusti et al., *PCR Methods and Applications*, 2:223-227 (1993), Fung et al., U.S. Pat. No. 4,757,141; Stabinsky, U.S. Pat. No. 4,739,044; Agrawal et al., *Tetrahedron Letters*, 31:1543-1546 (1990); Sproat et al., *Nucleic Acids Research*, 15:4837 (1987); Nelson et al., *Nucleic Acids Research*, 17:7187-7194 (1989); and the like. Still other commercially available linking groups can be used that can be attached to an oligonucleotide during synthesis, e.g., available from Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, for example, Woo et al., U.S. Pat. No. 5,231, 191; Hobbs, Jr., U.S. Pat. No. 4,997,928; Reed, et al., PCT publication No. WO 01/42505; U.S. Ser. Nos. 09/876,830; 10/084,818; and 10/026,374, each of which is hereby incorporated herein by reference.

While a number of general linking methods are available, the selection of certain linking groups constitute one aspect of the invention, when selection is made in combination with other factors such as oligonucleotide length, minor groove binders, fluorophore-quencher pairs, and the like. For example, in the present invention, the use of minor groove binders allows the preparation of probes having fewer nucleotide bases. In general, probes having fewer than about 15 bases have been considered unusable due to poor signaling and/or hydridization to target polynucleotides. Additionally, smaller probes (e.g., those of 15 or fewer bases) have been avoided for beacon assays as the quencher/fluorophore often are not sufficiently separated to provide a suitable signal upon hybridization.

In the present invention, shorter probes having attached minor groove binders are found to be useful, and sufficient spacing between the fluorophore and quencher can be obtained by selection of an appropriate linking group. Accordingly, the present invention provides novel probe/conjugates that are both efficient, inexpensive and useful in real-time assays.

The probes and conjugates of the present invention will generally have one or two types of linking groups. As provided in formula I, the letter K represents a divalent linking group, while the letter W represents a trivalent linking group. The particular linking groups are generally selected for their ease of synthesis, utility in solid phase synthesis, stability during probe construction and use, and the physical parameters each imparts to the probe or conjugate such as providing adequate separation between the fluorophore and the quencher; or providing a tether of suitable length to allow the minor groove binder portion to non-covalently interact with the minor groove formed upon probe hybridization.

More particularly, K is a direct bond between a fluorophore and the oligonucleotide portion of the probe/conjugate, or is a divalent linking group having from 1 to 30 main chain atoms that are selected from C, O, N, S, P and Si. Selection of a suitable linking group is generally made with consideration of the ODN length of the probe. Typically, shorter linking groups can be used when the ODN is longer than about 15-18 nucleotides, while longer linking groups are more useful when shorter probes are desired and/or constructed. In one group of preferred embodiments, K is a linking group having a formula selected from $-(O-(CH_2)_p)_q-$ wherein the subscript p is an integer of from 2 to 14 and the subscript q is an integer of from 1 to 10, with the proviso that the overall length of K is less than about 50 atoms. Preferably, K is selected from $-(OCH_2CH_2)_3-$, $-OCH_2CH_2)_6-$, $-(O(CH_2)_{12})-$ and $-(O(CH_2)_{12})_2-$. In another group of embodiments, K is preferably a linking group having the formula:

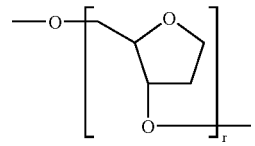

wherein the subscript r is an integer of from 1 to 5, preferably 1 or 2, most preferably 2.

The trivalent linking group W can encompass a variety of structures in order to provide suitable attachment and flexibility between the ODN, Q and M. In one group of embodiments, W is a trivalent functionality having the formula:

wherein the nitrogen atom is directly attached to an aromatic ring of a mono azo- or bis azo-dye (quencher, Q) and typically considered as part of the quencher, and the components $A^1$ and $A^2$ are independently selected from a bond or a linking/spacer portion having from 1 to about 50 atoms selected from C, N, S, P, Si and O, and additional hydrogen atoms to fill the available valences. Additionally, each of $A^1$ and $A^2$ can have cyclic components, acyclic (linear or branched) components, or a combination thereof.

Methods of Use

The probes/conjugates of the present invention provide numerous advantages over existing probes and conjugates, including superior mismatch discrimination improving genotyping. The probes/conjugates of the invention are particularly useful wherein their hybridization to a target sequence is detected in real-time (or coincident) with an amplification process such as, for example, PCR. Additionally, in one embodiment, the probes/conjugates of the present invention are not digested by 5'-nuclease activity. Accordingly, the amplification reactions can be archived and reevaluated by melting curve analysis. The probes/conjugates of the inventions are also useful in the case where they are digested by an enzyme such as a 5'-nuclease enzyme to genotype targets. Detection of mismatches by enzymatic cleavage of a fluorophore or a quencher from a hybridizing probe/conjugate is described in U.S. patent application Ser. No. 10/645,353, hereby incorporated herein by reference. The probes/conjugates of the present invention are particularly useful in genotyping when used in other amplification systems.

The probes/conjugates of the present invention are useful in other techniques in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; and techniques in which two or more oligonucleotides are hybridized to a target nucleic acid and interactions between the multiple oligonucleotides are measured. Conditions for hybridization of oligonucleotides, and factors which influence the degree and specificity of hybridization, such as temperature, ionic strength and solvent composition, are well-known to those of skill in the art. See, for example, Sambrook et al., supra; Ausubel, et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al. (1991) *Nucleic Acids Res.* 19:5143-5151. In still other methods, multiple probes can be used to detect alternate target site regions (e.g., th identify difficult sequences or to differentiate species and subspecies of the target).

Hybridization of probes and/or conjugates to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

It is understood that $T_m$ determined for the probes/conjugates is a function of the thermodynamic parameters of the duplex, concentration of the probe and target, nearest neighbors and probe length. For this reason the $T_m$s reported have been determined with probes of the same length, known probe and target concentration and same nearest neighbors.

For those probes/conjugates which incorporate universal bases, it is understood that the universal base forms "base pairs" with each of the natural DNA or RNA bases with little or no discrimination. It is understood that little or no discrimination can be measured in terms of $T_m$ differences when a probe containing a universal base hybridizes to four identical complementary targets except that each of the four targets contains either A, C, G or T in a base position complementary to the universal base. Preferably the difference in $T_m$ of the probe/target duplex of the four targets each target containing A, C, G or T complementary to the universal base is about 5° C., 4° C. or 3° C. Most preferably the $T_m$ difference is smaller than about 2° C. or 1° C. or less.

In the case of those probes/conjugates which incorporate promiscuos bases, it is understood that the universal base forms two hydrogen bonds with two or more of each of the natural DNA or RNA bases with similar thermodynamic properties. It is understood that little or no discrimination or similar thermodynamic properties can be measured in terms of $T_m$ differences when a probe containing a promiscuous (indiscriminative) base hybridizes to two or more identical complementary targets except that each of the more than two targets contains any two or more A, C, G or T in a base position complementary to the promiscuous (indiscrimina-tive) base. Preferably the difference in $T_m$ of the probe/target duplex of the more than two targets each of the target containing any two or more A, C, G or T complementary to the promiscuous (indiscriminative) base is about 5° C., 4° C. or 3° C. Most preferably the $T_m$ difference is smaller than about 2° C. or 1° C. or less.

For those probes/conjugates which incorporate modified bases, it is understood that the modified bases will retain the base-pairing specificity of their naturally-occurring analogues. For example, PPPG analogues are complementary to cytosine, while PPPA analogues are complementary to thymine and uracil. The PPPG and PPPA analogues not only have a reduced tendency for so-called "wobble" pairing with non-complementary bases, compared to guanine and adenine, but the 3-substituted groups increase binding affinity in duplexes. Similarly, modified pyrimidines hybridize specifically to their naturally occurring counter partners.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, concentration of organic solvents such as formamide and dimethylsulfoxide and chaotropes.

Thus, in the formation of hybrids (duplexes) between a probe/conjugate and its target sequence, the probe/conjugate is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined by methods that are well-known in the art. A preferred method is to determine the $T_m$ of the hybrid duplex. This is accomplished, as described supra, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature where 50% of bases of the hybrid duplexe are unstacked. Alternatively, if $T_m$s are known, a hybridization temperature (at fixed ionic strength, pH and probe/target concentration) can be chosen that it is below the $T_m$ of the desired duplex and above the $T_m$ of an undesired duplex. In this case, determination of the degree of hybridization is accomplished simply by testing for the presence of hybridized probe.

In some embodiments, the probe/conjugate is capable of acting as a primer, and the degree of hybridization of the probe/conjugate can also be determined by measuring the levels of the extension product of the primer. In this embodiment, either the primer can be labeled, or one or more of the precursors for polymerization (normally nucleoside triphosphates) can be labeled. Extension product can be detected, for example, by size (e.g., gel electrophoresis), affinity methods with hybridization probes as in real time PCR, or any other technique known to those of skill in the art.

Primer extension ("minisequencing", "genetic bit analysis") assays are commonly used for SNP typing and have can also be used in other genotyping and mutation screening applications (Pastinen T. et al., *Genome Res.*, 10: 1031-42 (2000)). In the present invention, the presence of minor groove binders and, in some cases, modified bases can improve primer extension assays. For example, the added duplex stability provided by minor groove binder, or 5-substituted pyrimidine or 3-substituted pyrazolo[3,4-d]pyrimidine enables extensions to be performed at elevated temperatures. This is advantageous as problematic secondary structures in target molecules can be eliminated at elevated temperatures. Also, hybridization of target to primer is faster at higher temperature. Thermostable polymerases such as Taq polymerase and Bst DNA polymerase can be used in such reactions. While minor groove binders and modified bases can provide probes and primers have the advantages noted above, the use of a modified base will typically be in a position other than the 3'-terminal position in order to avoid primer extension inhibition.

Furthermore, minor groove binders and modified bases improve the specificity of assays by eliminating one class of false postitive signals. Primer sequences that form hairpin structures or homodimers are prone to template-independent extension (the 5' end of the primer functions as template), resulting in false positive signal. Minor groove binders and modified bases on "templates" inhibit extension by DNA polymerases. Thus, minor groove binders on the 5' end, or modified bases on the 3' end or middle of a primer, can prevent extension (false positives) from primer hairpins or primer dimers. Finally, PPG can be used to eliminate non-canonical structures formed by G-rich oligonucleotides, enabling primer extension assays in such sequences.

Other assays in which the present modified oligonucleotides are particularly useful are described in U.S. Pat. No. 6,312,894, hereby incorporated herein by reference.

Still other amplification assays in which the present probes/conjugates are useful include the amplification assays based on the invasive cleavage of oligonucleotide probes by flap endonucleases (Lyamichev et al., *Nature Biotechnol.*, 17:292-296 (1999)); self-sustained sequence replication type assays (Mueller et al, *Histochem. Cell Biol.*, 108:431-437 (1997)), 5'-nuclease assays (Livak, Gen. Analysis: Bioenginering, 14: 143-149 (1999), molecular beacon assays (U.S. Pat. No. 6,485,902), and Rolling Circle assays (U.S. Pat. No. 6,344,329), the teachings of each of which are hereby incorporated herein by reference. Modified probe/conjugates of the invention include universal or promiscuous (indiscriminative) bases and optionally modified bases. Non-natural backbones are also included such as monomers used in peptide nucleic acids, locked nucleic acids, and the like.

In view of the above, the present invention provides a method for continuous monitoring of polynucleotide amplification of a target nucleic acid sequence having at least two single nucleotide polymorphisms wherein a first single nucleotide polymorphism is to be distinguished and a second single nucleotide polymorphism is not distinguished, each of said polymorphisms being in a probe region of said target nucleic acid, the method comprising:

(a) combining a sample containing said target nucleic acid with one or more oligonucleotide primers adjacent to or overlapping with said probe region of the target sequence, a polymerizing enzyme, nucleotide substrates, and an oligonucleotide conjugate having a formula:

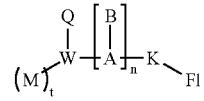

wherein M is a minor groove binder; the subscript t is 0 or 1; Q is a quencher; W is a linking group; K is a bond or a linking group; Fl is a fluorophore; and $[A-B]_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In a related aspect, the present invention provides a method for distinguishing in a sample between wild-type, mutant and heterozygous target polynucleotides in a target polynucleotide sequence having at least two single nucleotide polymorphisms wherein a first polymorphism is to be distinguished and a second single nucleotide polymorphism is not distinguished, each of said first and second polymorphisms being in a probe region of said target polynucleotides, the method comprising:

(a) contacting said sample containing said target polynucleotide sequence with a first probe and a second probe that each distinguish a first polymorphism of interest, wherein the first probe preferentially hybridizes to the wild-type target polynucleotide and the second probe preferentially hybridizes to the mutant target polynucleotide, each of the first and second probes having an independently selected formula:

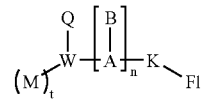

wherein M is a minor groove binder; the subscript t is 0 or 1; Q is a quencher; W is a linking group; K is a bond or a linking group; Fl is a fluorophore; and $[A-B]_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture; and (b) measuring the fluorescence produced on hybrid formation, whereby hybrid formation indicates the presence or absence of each of the wild-type, mutant and heterozygous target polynucleotides.

In still another aspect, the present invention provides a method for distinguishing in a sample between wild-type, mutant and heterozygous target polynucleotides in a target polynucleotide sequence having at least two single nucleotide polymorphisms wherein a first polymorphism is to be distinguished and a second single nucleotide polymorphism is not distinguished, each of said first and second polymorphisms being in a probe region of said target polynucleotides, the method comprising:

(a) contacting said sample containing said target polynucleotide sequence with a first probe and a second probe that each distinguish a first polymorphism of interest, wherein the first probe preferentially hybridizes to the wild-type target polynucleotide and the second probe preferentially hybridizes to the mutant target polynucleotide, each of the first and second probes having an independently selected formula:

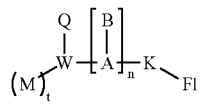

wherein M is a minor groove binder; the subscript t is 0 or 1; Q is a quencher; W is a linking group; K is a bond or a linking group; Fl is a fluorophore; and $[A\text{-}B]_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture; and (b) measuring the fluorescence using melting curve analysis of hybrid formation to determine the presence or absence of each of the wild-type, mutant and heterozygous target polynucleotides.

In still another aspect, the present invention provides a method for distinguishing in a sample between wild-type, mutant and heterozygous target polynucleotides in a target polynucleotide sequence having at least two single nucleotide polymorphisms wherein a first polymorphism is to be distinguished and a second single nucleotide polymorphism is not distinguished, each of said first and second polymorphisms being in a probe region of said target polynucleotides, the method comprising:

(a) contacting a sample containing at least one target polynucleotide sequence that comprises one or more polymorphisms not intended to be distinguished with a probe that hybridizes to both said wild-type target and said mutant target polynucleotide, wherein said probe preferentially hybridizes with the wild-type target polynucleotide in comparison to the mutant target polynucleotide, the probe having a formula:

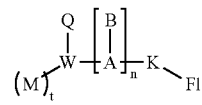

wherein M is a minor groove binder; the subscript t is 0 or 1; Q is a quencher; W is a linking group; K is a bond or a linking group; Fl is a fluorophore; and $[A\text{-}B]_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, a peptidic backbone or a variant thereof used in nucleic acid preparation; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture; and (b) measuring the fluorescence produced on hybrid formation, whereby hybrid formation indicates the presence or absence of each of the wild-type, mutant and heterozygous target polynucleotides.

For each of the methods above, probes are preferably those of formulae II, IIIa, IIIb, and IV along with the variations wherein positions of the fluorophore and quencher are reversed, as well as those wherein the minor groove binder and quencher are attached at the 3'-position, and the fluorophore is attached at the 5'-position. In still other embodiments, primers are used in amplification that contain modified bases, universal bases or promiscuous bases. Related aspects of the invention are those wherein probes of formula II, IIIa, IIIb, and IV are employed having universal or promiscuous bases at sites complementary to each SNP in a probe region of a target nucleic acid.

EXAMPLES

Example 1

This example demonstrates that a polymorphism can be genotyped in the presence of a second polymorphism in close proximity of the allele of interest, by substitution with a universal base in the probe position involved in second polymorphism. Generally, genotyping of a double polymorphism with single probe by traditional melting curve analysis has provided results that are inconclusive. Use the methods below provide a more accurate genotyping than has previously been achieved.

Materials and Methods 1.1 Templates

Human genomic DNAs were purchased from Coriell Institute of Medical Research, Camden, N.Y. Genotyping was previously done in our laboratory using restriction length polymorphism and TaqMan methods.

1.2 Oligonucleotides

Sequences of oligonucleotides used are shown in FIG. 1. Primers were synthesized using standard phosphoramidite chemistry. The 5'-MGB-Q Eclipse probes were prepared by automated DNA synthesis on a MGB-Q-modified glass support (MGB™ ligand is DPI3 a trademark of Epoch Biosciences, Bothell, Wash.) using 5'-β-cyanoethyl phosphoramidites (Glen Research, VA) designed for synthesis of oligonucleotide segments in 5'→3' direction. Oligonucleotide synthesis was performed on an ABI 394 synthesizer according to the protocol supplied by the manufacturer using a 0.02M iodine solution. PPG phosphoramidites were synthesized based on literature methods, but can also be purchased from Glen Research, Sterling, Va. 6-Carboxyfluorescein (FAM), Yakima Yellow™ (YY, from Epoch Biosciences, Inc., Bothell, Wash.) and 6-carboxy-4,7,2',7'-tetrachlorofluorescein (TET) reporting dyes were introduced at the last step of the synthesis using the corresponding phosphoramidites (Glen Research, Sterling, Va. Standard 5'-DMT phosphoramidites were used in this instance. All oligonucleotides were purified by reverse phase HPLC.

1.3 $T_m$ Prediction

MGB Eclipse™ Design Software 3.0 (Epoch Biosciences, Bothell, Wash.) was used to design the 5'-MGB-Q-ODN-Fl probes. One of the features of the software is the ability to design probes containing more than three consecutive Gs, known to be poor detection probes due to G:G self-association, and indicating an appropriate substitution of G with PPG. Additionally, the software can now design probes that incorporate Super A and Super T modified bases in AT-rich sequences to improve duplex stability. The software was used to design probes and primers. The amplicon, primers and probes are shown in FIG. 1 and Table 4.

1.4 Real Time PCR

Real-Time PCR Using MGB Eclipse Probes

Real-time PCR was conducted on either an ABI Prism® 7900 (Applied Biosystems, Foster City, Calif.), or on a Rotor-Gene 3000 (Corbett Research, Sydney, Australia) thermocycling fluorometer (Afonina et al, Ligand Assay, 25:268-275 (2002)). On both instruments, 50 cycles of three step PCR (95° C. for 5 s, 58° C. for 20 s and 76° C. for 30 s) after 2 min at 50° C. and 2 min at 95° C. were performed. For ABI 7900 commercially available 2× Jump Start PCR Mastermix with 2 mM final $Mg^{++}$ concentration (Sigma #D 74403) supplemented with Jump Start Taq-Polymerase (Sigma Catalog #90 4184) to a final amount of 0.37 U/μl reaction was used to set up this PCR reaction. Final concentration of both probes was 0.2 μM; concentration of limiting primer was 0.1 μM and excess primer was 2 μM. Each 5 μl reaction contained 10 ng of genomic DNA lyophilized in the plates with a speed vac prior to reaction set up. For the Rotor-Gene, the set-up was essentially the same except that the final volume of the reaction was increased to 10 μl, and sample DNA was added in 1× TE or water to the total amount of 10 ng/reaction.

Genotyping Analysis Using Fluorogenic Melt Curves and MGB Eclipse Probes

PCR setup for melt curve assays was the same as described for real-time experiments, although the PCR can be performed outside the thermocycling fluorometer. Details for melt curve analysis on the ABI 7900 are outlined below, and step-by-step instructions are provided in a User Manual available at www.epochbio.com. After completion of PCR, the plate is transferred to the ABI 7900, and the SDS software is set for dissociation curve analysis using fluorescein and tetrachlorofluorescein detection. The thermal profile is set using an initial denaturing temp of 95° C. for 30 seconds, an annealing temp of 30° C., and a final temp of 80° C. The ramp rate is set to 10% which is ~1 degree per 10 seconds. After reaching the final temp, the collected data are saved for analysis. The melt curve data can be graphically visualized as the first derivative of the melt curve over temperature. For automated genotyping, the data are exported to Microsoft Excel, and analyzed using the MGB Eclipse Melt Macro available from Epoch Biosciences (www.epochbio.com). The macro can automatically determine the $T_m$ of fluorescein and tetrachlorofluorescein probes if control samples or samples positive for each allele are present on the plate. Alternately, the user can manually set the probe $T_m$ if control samples are not available, as may be the case with rare alleles. User input may be required to adjust signal and $T_m$ threshold values after examining the melting curves. With this input, the macro automatically assigns genotype calls to individual samples and provides a tabular output of genotyping results.

The primers and probes shown in FIG. 1 were used to genotype a genomic target that contains two polymorphisms in the probe sequence. The [G/T] allele of interest could be genotype in the presence of a second allele N by melt curve analysis as shown in FIG. 2. Heterozygous samples showed a melting curve in both fluorescent channels in the $T_m$ window ranges set in the macro, while the wilde-type and mutant allele melting curves with the correct $T_m$s, were only present in their respective fluorescent channels.

Example 2

This example illustrates the evaluation of nitroindole (13) and nitropyrrole (9) as universal based in a model system. Eight targets were prepared to evaluate a probe with a polymorphism of interest in the presence of two additional polymorphisms in the probe sequence region. The probe and target sequences are shown in Table 4.

TABLE 4

Probe and target sequences to evaluate the base pair characteristics of nitroindole (13) and nitropyrole (9).
Probe Sequence
3'-CTTCTC$N_4$GATTCC$NB$AG-Q-MGB-5' (SEQ ID NO:8)

| | | $T_m$ ° C. Duplex | |
|---|---|---|---|
| Target # | Target Sequence 5'→3' | Nitroindole (13) | Nitropyrrole (9) |
| 1 | TTC CTA GGA ATC GGA GAA G (SEQ ID NO:9) | 50.3 | 44.3 |
| 2 | TTC CTT GGA ATC GGA GAA G (SEQ ID NO:10) | 52.2 | 44.9 |
| 3 | TTC CTC GGA ATC GGA GAA G (SEQ ID NO:11) | 56.1 | 48 |
| 4 | TTC CTG GGA ATC GGA GAA G (SEQ ID NO:12) | 53.1 | 45.1 |
| 5 | TTC CTA GGA ATC AGA GAA G (SEQ ID NO:13) | 51.3 | 47.6 |
| 6 | TTC CTT GGA ATC AGA GAA G (SEQ ID NO:14) | 51.3 | 48 |

TABLE 4-continued

Probe and target sequences to evaluate the base pair characteristics of nitroindole (13) and nitropyrole (9).
Probe Sequence
3'-CTTCTCN₄GATTCCNBAG-Q-MGB-5' (SEQ ID NO:8)

| Target # | Target Sequence 5'→3' | T_m ° C. Duplex Nitroindole (13) | Nitropyrrole (9) |
|---|---|---|---|
| 7 | TTC CTC GGA ATC AGA GAA G (SEQ ID NO:15) | 55.8 | 50.4 |
| 8 | TTC CTG GGA ATC AGA GAA G (SEQ ID NO:16) | 52.7 | 47.6 |

N₁ base evaluates the ability to hybridize to the G and A base of the polymorphism of interest.
N₂ base evaluates the ability to hybridize to the four natural bases.
N_A and N_B are both substituted at the same time by either universal base 9 or 13.

As shown both 9 and 13 hybridized with all 4 bases and had a $T_m$ leveling effect.

Example 3

This example describes the determination of the melting temperature of a probe:target duplex.

Thermodynamic parameters of duplex formation were derived by the Van't Hoff analysis methods. The shape of each melting curve was fitted to the two-state model with linear base lines (Xia, T. et al., *Biochem.*, 37, 14719-14735 (1998)) using a nonlinear least-square program (Lokhov, S. G. and Pyshnyi, D. V., *FEBS* 420, 134-138 1997)). Unless otherwise stated, $T_m$ of DNA duplexes were measured in 1×PCR buffer at a concentration of 5×10⁻⁷ M as described earlier (Kutyavin, I. V. et al., *Nucleic Acids Res.*, 28, 655-661 (2000)).

Example 4

This example illustrates the determination of the thermodynamic nearest neighbor parameters of the promiscuous (indiscriminative) base PPG. The theory and methods used are those disclosed in U.S. application Ser. No. 09/796,988 and PCT publication WO 01/64958, which are incorporated herein by reference in their entireties.

TABLE 5

The sequences of targets and probes to evaluate the influence of nearest-neighbors on $\Delta G°$ and $T_m$ of PPG

| # | SEQ ID NO: | | AgN |
|---|---|---|---|
| | | | -AgA- |
| 10 | 17 | TTTAGGTTTTTGGATTT | g/T |
| 11 | 18 | TTTAGGTTTTATGGATTT | g/A |
| 12 | 19 | TTTAGGTTTTGTGGATTT | g/G |
| 13 | 20 | TTTAGGTTTTCTGGATTT | g/C |

TABLE 5-continued

The sequences of targets and probes to evaluate the influence of nearest-neighbors on $\Delta G°$ and $T_m$ of PPG

Figure 6A:
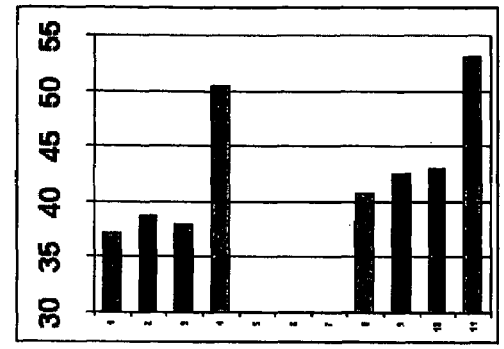
FIG. 6. Shows the thermodynamic properties for a) —AgN—, b) —TgN— and c) CgN— nearest-neighbors.
Figure 6A:
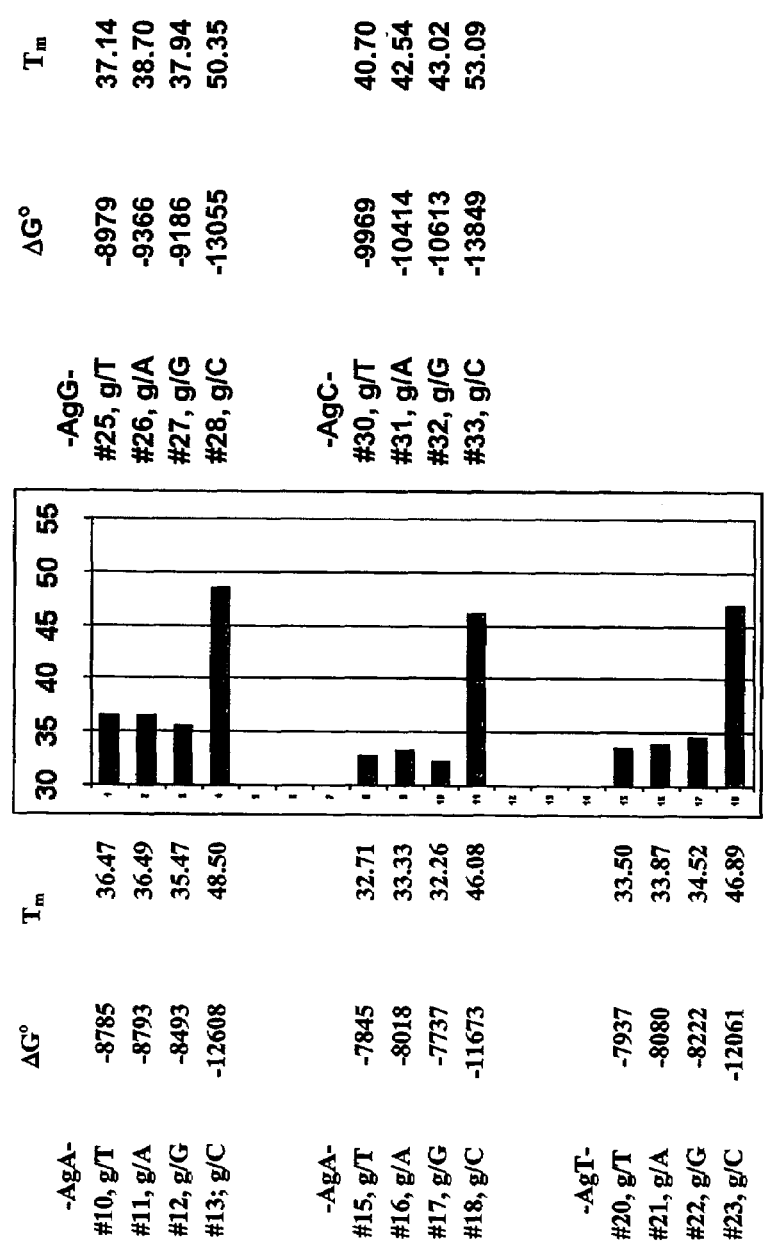

| # | SEQ ID NO: | | AgN |
|---|---|---|---|
| 14 | 21 | TCCAgAAAACCT | |
| | | | -AgA- |
| 15 | 22 | TTTAGTTTCCTTTGATTT | g/T |
| 16 | 23 | TTTAGTTTCCTATGATTT | g/A |
| 17 | 24 | TTTAGTTTCCTGTGATTT | g/G |
| 18 | 25 | TTTAGTTTCCTCTGATTT | g/C |
| 19 | 26 | TCAgAGGAAACT | |
| | | | -AgT- |
| 20 | 27 | TTTAGGATTATTGGATTT | g/T |
| 21 | 28 | TTTAGGATTAATGGATTT | g/A |
| 22 | 29 | TTTAGGATTAGTGGATTT | g/G |
| 23 | 30 | TTTAGGATTACTGGATTT | g/C |
| 24 | 31 | TCCAgTAATCCT | |
| | | | -AgG- |
| 25 | 32 | TTTAGACTTCTTGGATTT | g/T |
| 26 | 33 | TTTAGACTTCATGGATTT | g/A |
| 27 | 34 | TTTAGACTTCGTGGATTT | g/G |
| 28 | 35 | TTTAGACTTCCTGGATTT | g/C |
| 29 | 36 | TCCAgGAAGTCT | |
| | | | -AgC- |
| 30 | 37 | TTTAGAGTTGTTCGATTT | g/T |
| 31 | 38 | TTTAGAGTTGATCGATTT | g/A |
| 32 | 39 | TTTAGAGTTGGTCGATTT | g/G |
| 33 | 40 | TTTAGAGTTGCTCGATTT | g/C |
| 34 | 41 | TCGAgCAACTCT | | is probe and target number;
"g" is PPG (Super G). and
N is A, C, G or T.
N substitutions in the targets are shown in bold The probes and targets were used to determine the $\Delta G°$ and $T_m$ are shown in Table 5 for a number or nearest neighbors in sets of four targets and one probe. Each set for example includes four targets (eg. #10 to #13) and one probe (14) yielding four duplexes, three with mismatches and one match 14. FIGS. 6a) to c) therefore show in addition to $\Delta G°$ and $T_m$ data also a bar graph for $T_m$ in groups of four, three mismatches and one match. The results corresponding to the targets and probes listed in Table 5 are shown in FIG. 6a). The -AgA- sequence was evaluated with probe 14 and targets 10 to 13 as well as within a different sequence environment with probe 19 and targets 15 to 18. As shown in FIG. 6a) the ratios of the average $T_m$ of the three mismatches with that of the match for the -AgA- in different sequence environments were similar. This indicates that the nearest-neighbor motifs' thermodynamic contribution is independent of the rest of the sequence.

Figure 6B:
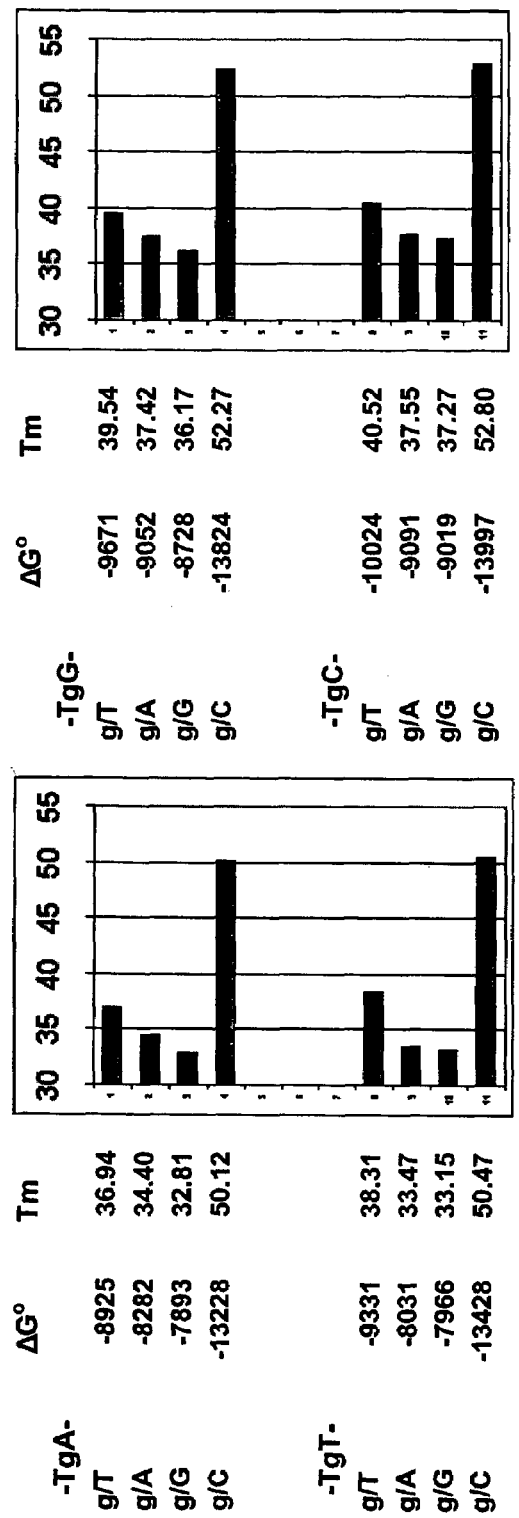
Figure 6C:
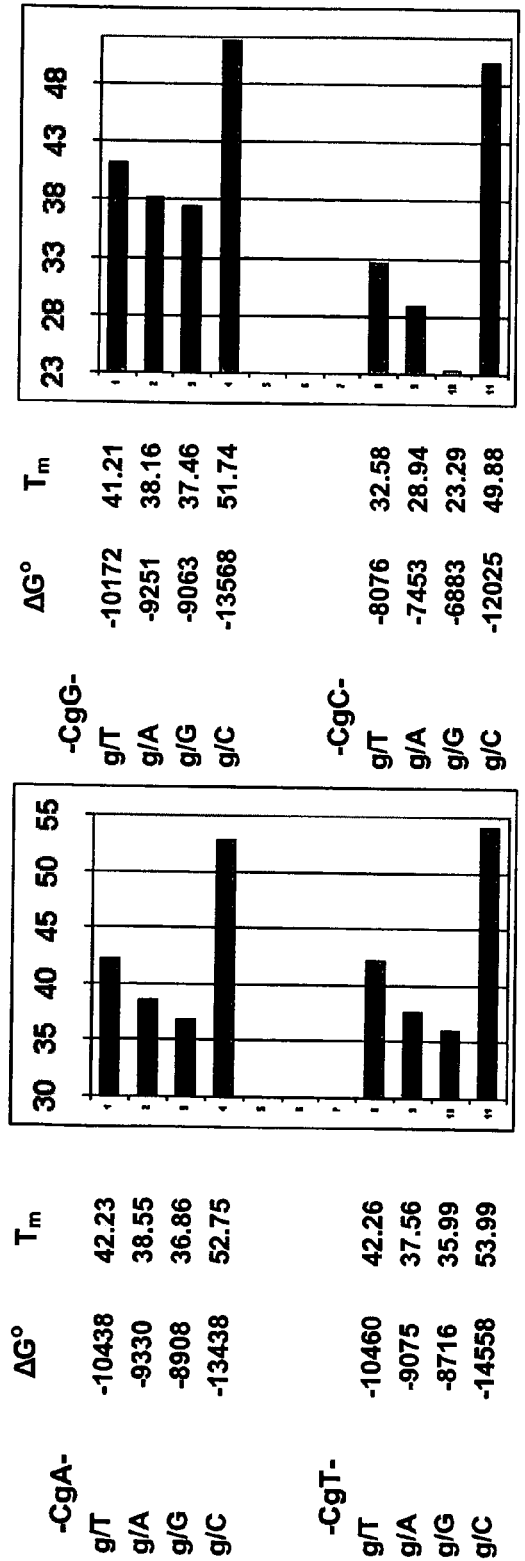

Similarly other probes and targets (sequences not shown) were used to determine the ΔG° and $T_m$s for additional nearest-neighbors and the results are shown in FIG. 6b) and 6c). The duplex $T_m$ difference between that of a normal matched probe and a probe substituted with a promiscuous (indiscriminative) base in FIG. 6, is similar or less than that observed with probes 9 and 13 substituted with the universal bases nitropyrole and nitroindole (Table 4), respectively.

Example 5

This example illustrates the use of a universal base 41 and 42 in probes to illustrate that a polymorphism can be made "invisible by substitution in a base corresponding to that of the target mutation. A portion of a SNP occurring in the BARD 1-03 gene sequence (http://snp500cancer.nci.nih.gov) is shown below.

```
Target:   3' . . . TGATATAGGT[G/A]CACG . . . 5' (SEQ
ID NO:42)

Probes: MGB-Q-ACTATATCCA N GTGC-Fl (SEQ ID NO:43)
```

Figure 7:
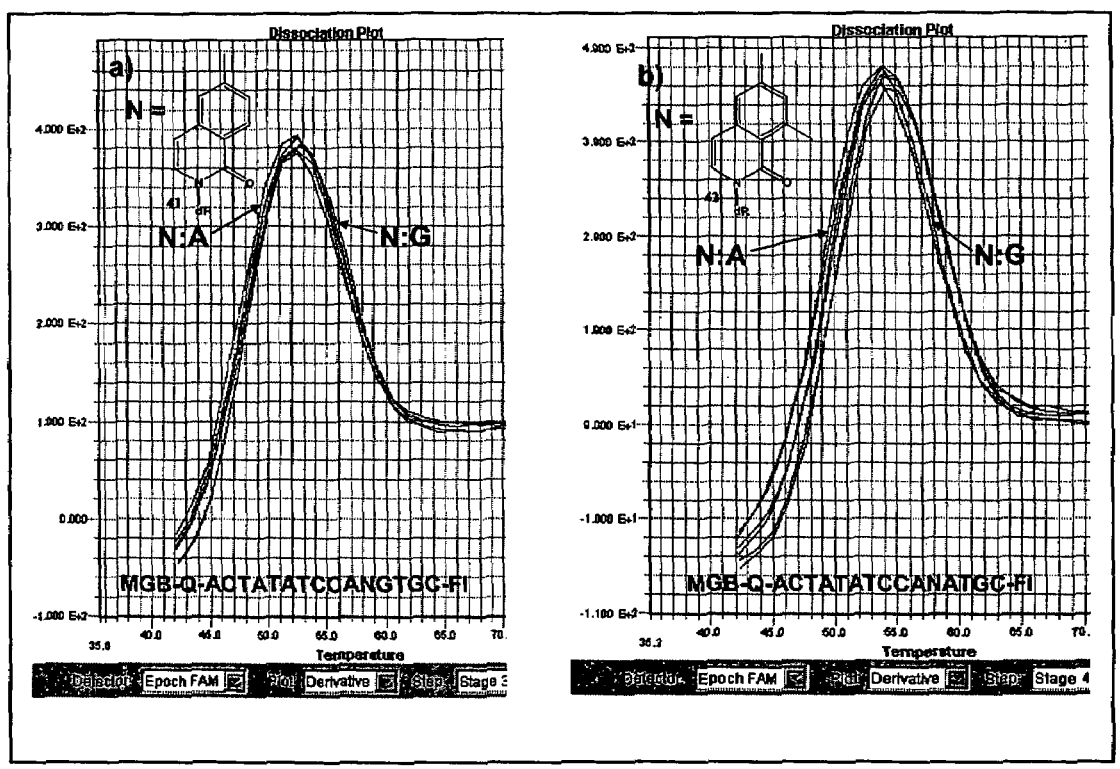
FIG. 7. Melting curves analysis of the sample BARD1-03 DNA containing a single polymorphism in the probe binding area, with probes labeled with fluorescein (SEQ ID NOS: 6 and 7), complementary to the wild-type and mutant targets of the polymorphism, respectively. The base corresponding to the polymorphism was substituted with either universal base 41 or 48.

The [G/A] polymorphism is made "invisible" by substitution of the corresponding position in the probe with universal base N. FIG. 7 shows a melting curve analysis of the probe when N is substituted with either universal base 41 or 42. In each case the probe was analyzed against both wild-type and mutant targets. As shown the sharp single melting curves (see FIGS. 7a and 7b) indicates that the two modified bases hybridize with similar thermostability to both wild-type and mutant targets.

Example 6

This example illustrates the use and comparison of a universal base 40 and a promiscuous (indiscriminative) base V (where $R^z$=$R^y$=—NH$_2$, $R^x$ is hydroxybutynyl and the backbone component is a deoxyribose) in probes to address the genotyping of double SNP occurring in the BARD1-03 gene with melting curve analysis. The portion of the BARD1-03 sequence with a double polymorphism (R=G/A) in the probe area and the probe sequences are shown below:

```
Target:   3' . . . TGATATAGGTRCACG . . . 5' (SEQ ID
NO:42)

Probes: MGB-Q-ACTATATCCANGTGC-Fl^A (SEQ ID NO:44)

MGB-Q-ACTATATCCANATGC-Fl^B (SEQ ID NO:45)
```

Figure 8:
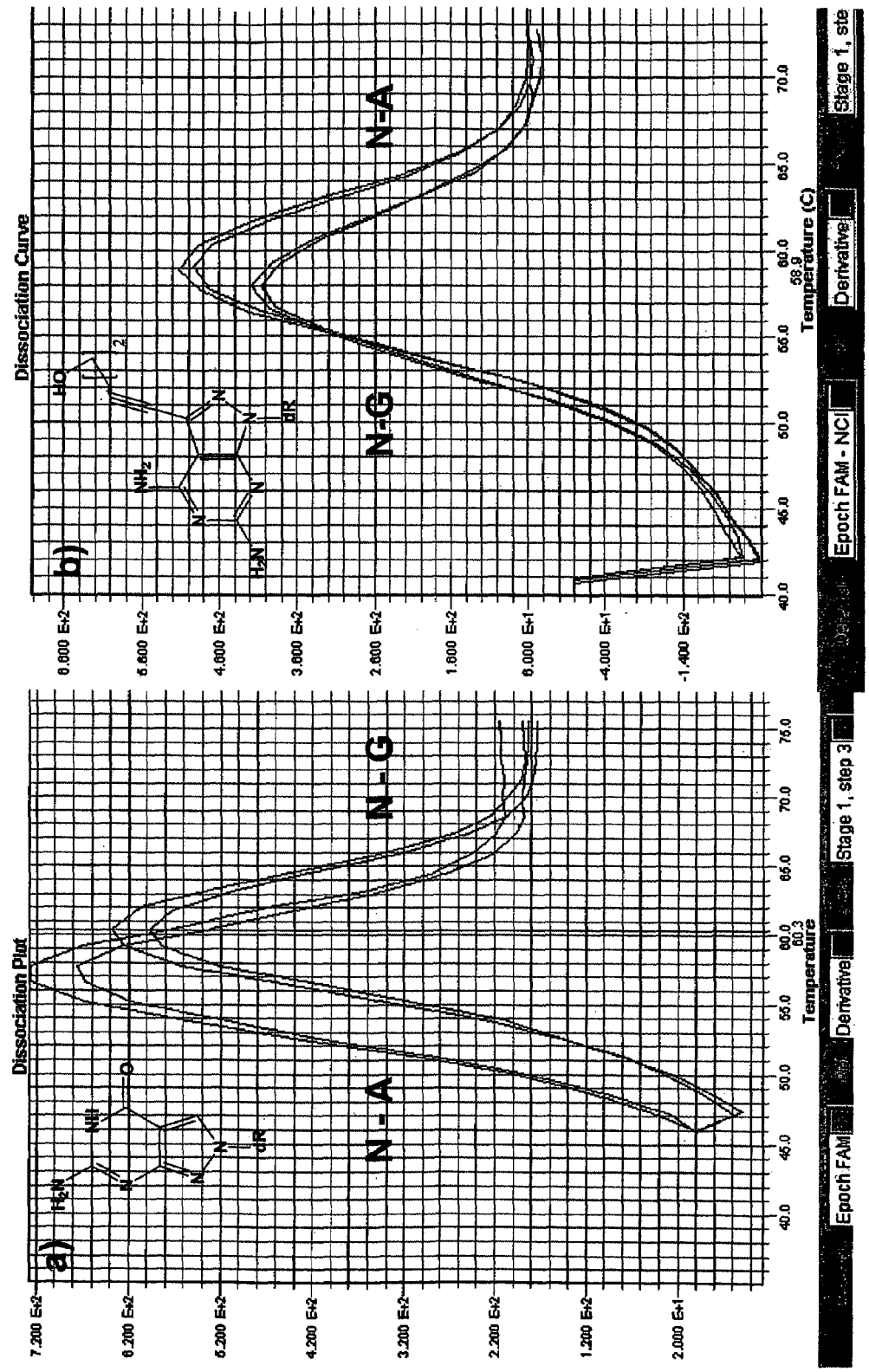
FIG. 8. Melting curves analysis of the sample BARD1-03 DNA containing a double polymorphism in the probe binding area, with probes labeled with fluorescein and tetrachlorofluorescein, complementary to the wild-type and mutant targets of the first polymorphism, respectively. The base corresponding to the second polymorphism was substituted with either universal base 40 or promiscuous (indiscriminative) base (V, where $R^z$=$R^y$=—NH$_2$, $R^x$ is hydroxybutynyl and $R^d$ is deoxyribose).

The polymorphism of interest is shown in bold underlined while the [R=G/A] polymorphism is made "invisible" by substitution of the corresponding position in the probe with universal or promiscuous (indiscriminative) base N, respectively. In FIG. 8 is shown a melting curve analysis of the BARD1-03 polymorphism of interest (bold underlined above) when N is substituted with either universal base 40 or promiscuous (indiscriminative) base (V where $R^z$=$R^y$=—NH$_2$, $R^x$ is hydroxybutynyl and the backbone component is deoxyribose). As shown, the sharp single melting curves in FIG. 8a) and b) indicates that the second polymorphism is "invisible". However in case of universal base 40 there is about a 2.8° C. $T_m$ difference between the NA and the NG probes used in FIG. 8a). The promiscuous (indiscriminative) base used in FIG. 8b) showed a $T_m$ difference between the NA and NG probes of only 0.8° C.

Example 7

This example illustrates the detection of two targets with a single mismatch with only one probe. A single probe was developed to detect both *Mycobacterium chelonae* and *M. abscessus* which differ only by a single mismatch in the probe area. The target and probe sequences are shown below. In this example two single probes substituted a) with PPG (49) and b) with a substituted pyrazolopyrimidine derivative (V where $R^z$=—$R^y$=—NH$_2$, $R^x$ is hydroxybutynyl and the backbone component is deoxyribose) is shown below.

```
Target 1:   TTTCTCTCAAAGACATC (SEQ ID NO:46)

Target 2:   TTTCTTTCAAAGACATC (SEQ ID NO:47)

Figure 9:
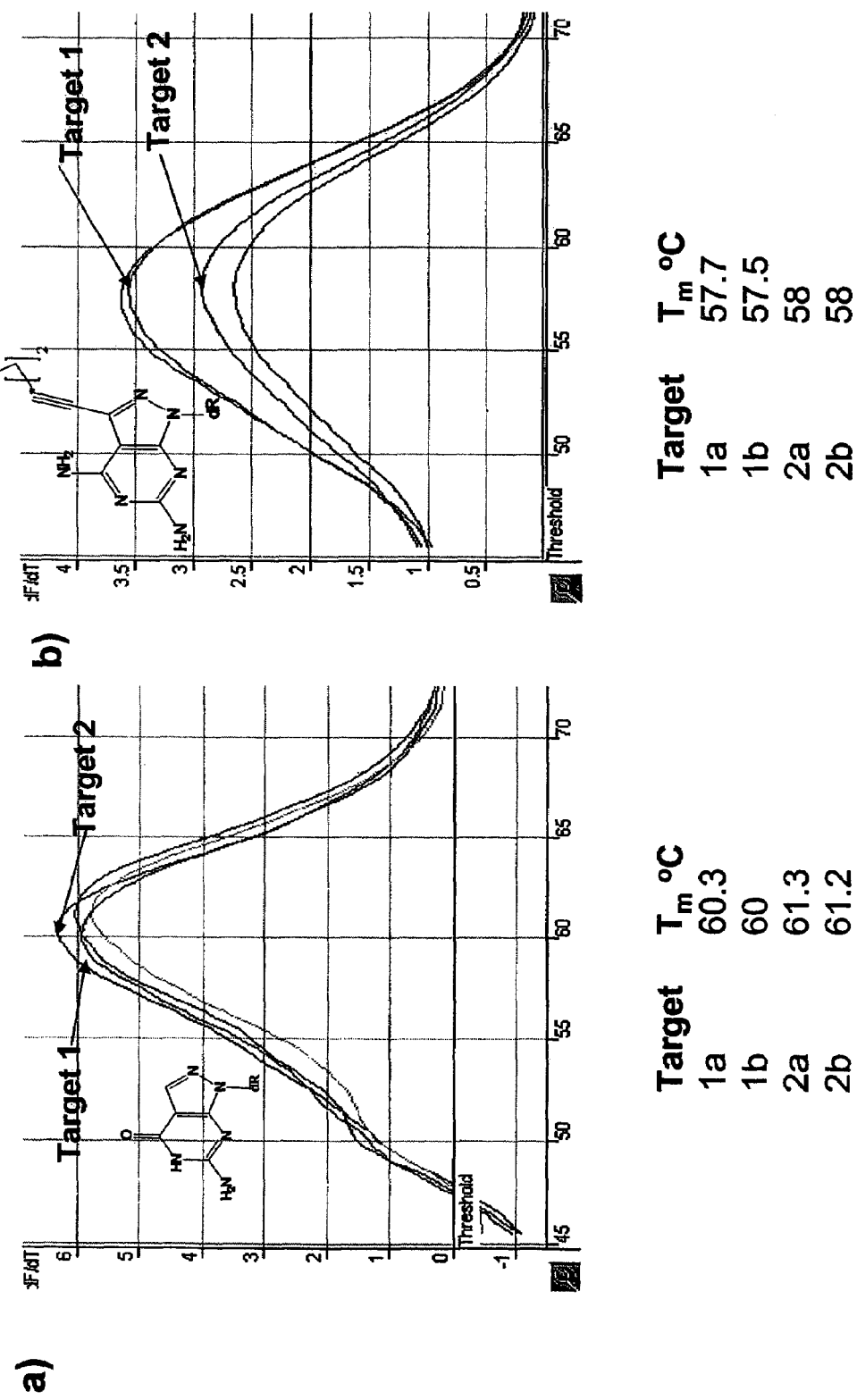
FIG. 9. Shows the detection of both *Mycobacterium chelonae* and *M. abscessus* which differ only by a single mismatch in the probe area, with a single probe.

Probe:      MGB-Q-AAAGNGAGTTTCTGTAG-TET (SEQ ID
            NO:48),
``` where N is either PPG (49) or a substituted pyrazolopyrimidine (V where $R^z$=$R^y$=—NH$_2$, $R^x$ is hydroxybutynyl and the backbone component is deoxyribose). The probes 49 and V were evaluated for their ability to detect both targets efficiently. The results of the melting curve analysis are shown in FIG. 9. FIG. 9a) represents the data obtain with 49 and 9b) the data obtained with the substituted pyrazolopyrimidine (V).

Example 8

This example demonstrates the synthesis of universal base 5'phosphoramidite (56)

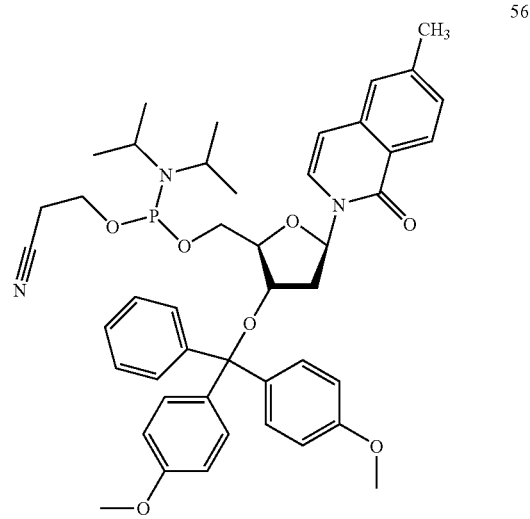

2-((2R, 4R,5R)-4-(bis(4-methoxyphenyl)(phenyl)methoxy)-tetrahydro-5-(hydroxymethyl)furan-2-yl)-6-methylisoquinolin-1(2H)-one (55). A 125 ml round bottom flask was charged with magnetic stirring bar, compound (41) (1.03 g, 2.0 mmol) in anhydrous pyridine (10 ml) and dimethylthexylsilyl chloride (0.59 ml, 0.536 g, 3.0 mmol) was added. Resultant mixture was magnetically stirred at room temperature for one day. Dimethoxytrityl chloride (0.88 g, 2.6 mmol) was added and reaction mixture was magnetically stirred for one more day. Reaction mixture was cooled with ice-water bath and prepared in advance solution of HF-Py complex (~2.0 g, ~1.4 g HF, ~70 mmol) in pyridine (10 ml) was added through a syringe during 10 min. Resultant mixture was magnetically stirred at room temperature for 2 days more. Reaction mixture was diluted with EtOAc (200 ml) and carefully poured into saturated aqueous sodium bicarbonate (100 ml). Organic phase was separated, washed with brine (50 ml), dried over $Na_2SO_4$, filtered, and concentrated in vacuum. Residue was coevaporated twice with toluene and purified by column chromatography to give pure desired product (55) (0.78 g, 1.36 mmol, yield=68%) as white foam. $^1$H NMR (dmso-$d_6$): 8.08 (d, J=8.2 Hz, 1H), 7.60 (d, J=7.6 Hz, 1H), 7.50-7.20 (m, 11H), 6.92 (d, J=8.0 Hz, 4H), 6.64 (t, J=7.2 Hz, 1H), 6.55 (d, J=7.5 Hz, 1H), 4.95 (t, J=5.1 Hz, 1H), 4.30 (bt, J=4.0 Hz, 1H), 3.82 (bt, J=4.0 Hz, 1H), 3.74 (s, 3H), 3.73 (s, 3H), 2.42 (s, 3H), 1.68 (m, 2H), 1.24 (m, 2H).

Universal base 5'phosphoramidite (56). A 50 ml round bottom flask was charged with compound (2) (0.25 g, 0.43 mmol), diisopropylammonium tetrazolide (0.081 g, 0.47 mmol), and stirring bar. Flask was evacuated and filled with argon. Then anhydrous $CH_2Cl_2$ (5 ml) was added followed by 2-cyanoethyl tetraisopropylphoshordiamidite (0.259 g, 0.86 mmol). Resultant mixture was stirred under argon at room temperature for 2 h. Reaction mixture was diluted with $CH_2Cl_2$ (50 ml) and quenched with saturated aqueous sodium bicarbonate (10 ml). Organic solution was separated, washed with brine (2×10 ml) and dried over $Na_2SO_4$. Solution was filtered and concentrated in vacuum. Residue was purified by column chromatography (column was prewashed with 5% $Et_3N$ in hexane followed by pure hexane; 30% EtOAc in Hex) to give pure desired product (56) (0.28 g, 0.36 mmol, yield=84%) as white foam. $^{31}$P NMR ($CDCl_3$): 144.56 (s), 144.20 (s).

Example 9

This example demonstrates the synthesis of universal base 5'phosphoramidite (65)

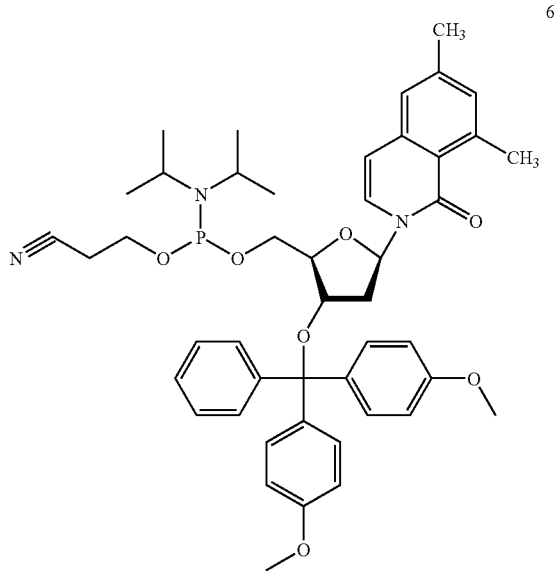

6,8-Dimethylisoquinolin-1(2H)-one (61): Compound (61) was prepared according to published synthetic route (Briet et al, *Tetrahedron* 58:5761-5766 (2002)) starting from commercially available 3,5-dimethylbenzaldehyde (57) through (60). $^1$H NMR (dmso-$d_6$): 10.91 (bs, 1H), 7.21 (s, 1H), 7.10-7.00 (m, 2H), 6.36 (d, J=7.0 Hz, 1H), 2.76 (s, 3H), 2.33 (s, 3H).

2-((2R, 4R, 5R)-tetrahydro-4-hydroxy-5-(hydroxymethyl)furan-2-yl)-6,8-dimethylisoquinolin-1(2H)-one (63): A 0.25 L round bottom flask was charged with magnetic stirring bar, compound (61) (1.0 g, 5.77 mmol), acetonitrile (10 ml), and DMF (20 ml). Mixture was cooled to +0° C. with ice-water bath and sodium hydride (0.150 g, 5.95 mmol) was added in one portion. After 5 min reaction mixture was let warmed to room temperature and was magnetically stirred during 1.5 h. Compound (62) (2.245 g, 5.77 mmol) was added in one portion and reaction mixture was magnetically stirred for 6 h at room temperature. One more portion of compound (62) (0.453 g, 1.17 mmol) was added and reaction mixture was stirred for 2 h more at room temperature. Reaction mixture was concentrated in vacuum, water (50 ml) was added and the mixture was extracted with $CH_2Cl_2$ (2×50 ml). Organic solution was washed with brine (2×20 ml), dried over $MgSO_4$, filtered from drying agent and concentrated in vacuum. Residue was separated on silica column (0-2% EtOAc in DCM) to give pure toluyl protected intermediate (0.64 g, 1.22 mmol, yield=21%) as white foam. Column was further washed with EtOAc to give pure starting material (61) (0.62 g, 3.58 mmol, yield=62%) as off-white solid. Toluyl protected intermediate (2.7 g, 5.14 mmol) was placed in 0.5 L round bottom flask charged in advance with magnetic stirring bar, methanol (40 ml), and THF (8 ml). Resultant mixture was cooled to +0° C. and freshly prepared sodium methoxide from sodium (0.345 g, 15.0 mmol) and methanol (20 ml) was added in one portion. Reaction mixture was magnetically stirred for 1 h at +0° C. Reaction mixture was quenched with ammonium chloride (1.07 g, 20 mmol) and concentrated in vacuum. Residue was separated on silica column (hexane/EtOAc/MeOH=4:4:1) to give desired product (63) (1.36 g, purity ~90%, ~4.2 mmol, yield=82%) as slightly purple solid. Product contained ~10% toluic acid according to $^1$H NMR. $^1$H NMR (dmso-$d_6$): 7.62 (d, J=7.5 Hz, 1H), 7.22 (s, 1H), 7.06 (s, 1H), 6.53 (t, J=6.7 Hz, 1H), 6.50 (d, J=7.5 Hz, 1H), 5.40-5.00 (bm, 2H), 4.28 (m, 1H), 3.84 (m, 1H), 3.61 (m, 2H), 2.76 (s, 3H), 2.35 (s, 3H), 2.20 (m, 1H), 2.00 (m, 1H).

2-((2R, 4R, 5R)-4-(bis(4-methoxyphenyl)(phenyl)methoxy)-tetrahydro-5-(hydroxymethyl)furan-2-yl)-6,8-dimethylisoquinolin-1(2H)-one (64). Compound (64) was prepared similar to compound (55). $^1$H NMR (dmso-d6): 7.54 (d, J=7.6 Hz, 1H), 7.50-7.16 (m, 10H), 7.06 (s, 1H), 6.92 (d, J=8.3 Hz, 4H), 6.60 (dd, J=8.8, 5.8 Hz, 1H), 6.45 (d, J=7.6 Hz, 1H), 4.91 (t, J=5.0 Hz, 1H), 4.29 (d, J=4.5 Hz, 1H), 3.74 (s, 3H), 3.73 (s, 3H), 3.72 (m, 1H), 3.35 (m, 1H), 3.18 (m, 1H), 2.75 (s, 3H), 2.34 (s, 3H), 2.20 (m, 2H).

5'-Phosphoramidite of universal base (65). Compound (65) was prepared similar to compound (56). $^{31}$P NMR ($CDCl_3$): 144.56 (s), 144.16(s).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for continuous monitoring of polynucleotide amplification of a target nucleic acid sequence having at least two single nucleotide polymorphisms wherein a first single nucleotide polymorphism is to be distinguished and a second single nucleotide polymorphism is not distinguished, each of said polymorphisms being in a probe region of said target nucleic acid, the method comprising:

(a) combining a sample containing said target nucleic acid with one or more oligonucleotide primers adjacent to or overlapping with said probe region of the target sequence, a polymerizing enzyme, nucleotide substrates, and an oligonucleotide conjugate having a formula:

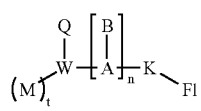

wherein M is a minor groove binder; the subscript t is 0 or 1; Q is a quencher; W is a linking group; K is a bond or a linking group; Fl is a fluorophore; and $[A-B]_n$ represents a nucleic acid oligomer having n units, wherein n is an integer of from 5 to 50; each A independently represents a nucleic acid backbone component selected from the group consisting of a sugar phosphate backbone, a modified sugar phosphate backbone, a locked nucleic acid backbone, and a peptidic backbone; and each B independently represents a nucleic acid base, a modified base or a base analog and wherein the base at the site complementary to said second single nucleotide polymorphism, is a universal or promiscuous (indiscriminative) base and the oligonucleotide portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

2. The method of claim 1, wherein the minor groove binder (M) is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepine analogs.

3. The method of claim 1, wherein the minor groove binder (M) is a substituted dihydrocyclopyrroloindole triamide ($DPI_3$).

4. The method of claim 1, wherein the minor groove binder (M) is attacked to the 5' end of the oligonucleotide conjugate.

5. The method of claim 1, wherein the minor groove binder (M) is attached to the 3' end of the oligonucleotide conjugate.

6. The method of claim 1, wherein Q is a quencher with an absorption spectra between about 400 to 800 nm, and Fl is a fluorophore with emission wavelengths between about 400 to 800 nm.

7. The method of claim 1, wherein said fluorophore (Fl) is selected from the group consisting of coumarins, resorufins, xanthenes, benzoxanthenes, cyanines and bodipy analogs.

8. The method of claim 1, wherein said quencher (Q) is selected from the group consisting of mono azo and bis azo dyes.

9. The method of claim 1, wherein said sugar phosphate backbone (A) comprises 8-25 nucleotides in length.

10. The method of claim 1, wherein the fluorescence is produced directly upon hybridization of the probe with said target nucleic acid sequence.

11. The method of claim 1, wherein the fluorescence is produced upon enzymatic cleavage of the quencher or the fluorophore from the conjugate probe upon hybridization with a target nucleic acid sequence.

12. The method of claim 1, wherein the universal base is selected from the group provided in Table 1.

13. The method of claim 1, wherein the promiscuous base is selected from the group provided in Table 2.

14. The method of claim 1, wherein the promiscuous (indiscriminative) base has the formula:

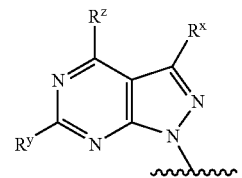

wherein $R^y$ and $R^z$ are independently selected from the group consisting of OH and $NH_2$ and at least one of $R^y$ or $R^z$ is $NH_2$; and $R^x$ is a member selected from the group consisting of H, ($C_1$-$C_{12}$)alkyl, ($C_2$-$C_{12}$)alkenyl, ($C_2$-$C_{12}$)alkynyl, ($C_2$-$C_{12}$)heteroalkyl, ($C_3$-$C_{12}$)heteroalkenyl, ($C_3$-$C_{12}$)heteroalkynyl, —O—($C_1$-$C_{12}$)alkyl, —O—($C_2$-$C_{12}$)alkenyl, —O—($C_2$-$C_{12}$)alkynyl, —S—($C_1$-$C_{12}$)alkyl, —S—($C_2$-$C_{12}$)alkenyl, —S—($C_2$-$C_{12}$)alkynyl, heterocyclyl($C_1$-$C_{12}$)alkyl, heterocyclyl($C_2$-$C_{12}$)alkenyl, heterocyclyl($C_2$-$C_{12}$)alkynyl, aryl($C_1$-$C_{12}$)alkyl, aryl($C_2$-$C_{12}$)alkenyl, aryl($C_2$-$C_{12}$)alkynyl, aryl, heterocyclyl, halogen, —CN and —$CONH_2$, wherein the aliphatic portions of $R^x$ are further substituted with one or two hydroxy, amino or halogen groups; and the wavy line indicates the point of attachment to the remainder of the probe.

* * * * *

SEQUENCE LISTING

<160> NUMBER OF SEQ ID NOS: 48

<210> SEQ ID NO 1
<211> LENGTH: 98
<212> TYPE: DNA
<213> ORGANISM: Artificial Sequence
<220> FEATURE:
<223> OTHER INFORMATION: Description of Artificial Sequence:double
      polymorphism human genomic target amplicon
<220> FEATURE:
<221> NAME/KEY: modified_base
<222> LOCATION: (28)
<223> OTHER INFORMATION: n = g, a, c or t, second natural polymorphism
<220> FEATURE:
<221> NAME/KEY: modified_base
<222> LOCATION: (56)
<223> OTHER INFORMATION: n = g, a, c or t

<400> SEQUENCE: 1
atattctttg ccaggtattt cctctctnkc atctcatctt gtaaaattat atccanagga     60
tgtaatatta tgcccatgcg atactaaggc gagaagtt                             98

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:synthesized
      phosphoramidite primer
<220> FEATURE:
<221> NAME/KEY: modified_base
<222> LOCATION: (1)..(20)
<223> OTHER INFORMATION: phosphoramidite replaces phosphodiester
      linkages
<220> FEATURE:
<221> NAME/KEY: modified_base
<222> LOCATION: (2)
<223> OTHER INFORMATION: n = 4-(4,6-diamino-1H-pyrozolo[3,4-d]pyrimidin-
      3-yl)-but-3-yn-1-ol (Super A) nucleotide

<400> SEQUENCE: 2
ancttctcgc cttagtatcg                                                  20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:synthesized
      phosphoramidite primer
<220> FEATURE:
<221> NAME/KEY: modified_base
<222> LOCATION: (1)..(19)
<223> OTHER INFORMATION: phosphoramidite replaces phosphodiester
      linkages
<220> FEATURE:
<221> NAME/KEY: modified_base
<222> LOCATION: (3)
<223> OTHER INFORMATION: n = 4-(4,6-diamino-1H-pyrozolo[3,4-d]pyrimidin-
      3-yl)-but-3-yn-1-ol (Super A) nucleotide
<220> FEATURE:
<221> NAME/KEY: modified_base
<222> LOCATION: (13)
<223> OTHER INFORMATION: n = 4-(4,6-diamino-1H-pyrozolo[3,4-d]pyrimidin-
      3-yl)-but-3-yn-1-ol (Super A) nucleotide

<400> SEQUENCE: 3
atnttctttg ccnggtatt                                                   19

```
<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:Probe Fa
      synthesized phosphoramidite probe oligonucleotide
      with minor groove binder, quencher and fluorophore
<220> FEATURE:
<221> NAME/KEY: modified_base
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = g linked to substituted
      dihydrocyclopyrroloindole minor groove binder
      (MGB) and a quencher (Q)
<220> FEATURE:
<221> NAME/KEY: modified_base
<222> LOCATION: (8)
<223> OTHER INFORMATION: n = 6-amino-2-(4-hydroxy-5-hydroxymethyl-
      tetrahydro-furan-2-yl)-2,5-dihydro-pyrazolo[3,4-d]
      pyramidin-4-one (compound U-40) nucleotide
<220> FEATURE:
<221> NAME/KEY: modified_base
<222> LOCATION: (15)
<223> OTHER INFORMATION: n = g linked to fluorescein (Fa)

<400> SEQUENCE: 4
nagatgcnag agagn                                                     15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:Probe Fb
      synthesized phosphoramidite probe oligonucleotide
      with minor groove binder, quencher and fluorophore
<220> FEATURE:
<221> NAME/KEY: modified_base
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = g linked to substituted
      dihydrocyclopyrroloindole minor groove binder
      (MGB) and a quencher (Q)
<220> FEATURE:
<221> NAME/KEY: modified_base
<222> LOCATION: (8)
<223> OTHER INFORMATION: n = 6-amino-2-(4-hydroxy-5-hydroxymethyl-
      tetrahydro-furan-2-yl)-2,5-dihydro-pyrazolo[3,4-d]
      pyramidin-4-one (compound U-40) nucleotide
<220> FEATURE:
<221> NAME/KEY: modified_base
<222> LOCATION: (15)
<223> OTHER INFORMATION: n = g linked to tetrachlorofluorescein (Fb)

<400> SEQUENCE: 5
nagatganag agagn                                                     15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:BARD1-03
      single polymorphism probe
<220> FEATURE:
<221> NAME/KEY: modified_base
```

```
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (11)
<223> OTHER INFORMATION: n = 6-methyl-2-isoquinoline-1-one nucleotide or
      6,8-dimethylisoquinolin-1(2H)-one nucleotide
<220> FEATURE:
<221> NAME/KEY: modified_base
<222> LOCATION: (15)
<223> OTHER INFORMATION: n = c linked to fluorescein

<400> SEQUENCE: 6
nctatatcca ngtgn                                                       15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:BARD1-03
      single polymorphism probe
<220> FEATURE:
<221> NAME/KEY: modified_base
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (11)
<223> OTHER INFORMATION: n = 6-methyl-2-isoquinoline-1-one nucleotide or
      6,8-dimethylisoquinolin-1(2H)-one nucleotide
<220> FEATURE:
<221> NAME/KEY: modified_base
<222> LOCATION: (15)
<223> OTHER INFORMATION: n = c linked to fluorescein

<400> SEQUENCE: 7
nctatatcca natgn                                                       15

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence:synthetic
      probe sequence
<220> FEATURE:
<221> NAME/KEY: modified_base
<222> LOCATION: (1)..(16)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = g linked to substituted
      dihydrocyclopyrroloindole minor groove binder
      (MGB) and a quencher (Q)
<220> FEATURE:
<221> NAME/KEY: modified_base
<222> LOCATION: (3)
<223> OTHER INFORMATION: n = 3-nitropyrrole nucleotide or 5-nitroindole
```

```
      nucleotide
<220> FEATURE:
<221> NAME/KEY: modified_base
<222> LOCATION: (10)
<223> OTHER INFORMATION: n = 3-nitropyrrole nucleotide or 5-nitroindole
      nucleotide

<400> SEQUENCE: 8
nanccttagn ctcttc                                                    16

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:synthetic
      target #1

<400> SEQUENCE: 9
ttcctaggaa tcggagaag                                                 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:synthetic
      target #2

<400> SEQUENCE: 10
ttccttggaa tcggagaag                                                 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:synthetic
      target #3

<400> SEQUENCE: 11
ttcctcggaa tcggagaag                                                 19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:synthetic
      target #4

<400> SEQUENCE: 12
ttcctgggaa tcggagaag                                                 19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:synthetic
      target #5

<400> SEQUENCE: 13
ttcctaggaa tcagagaag                                                 19

<210> SEQ ID NO 14
<211> LENGTH: 19
```

```
<212> TYPE: DNA
<213> ORGANISM: Artificial Sequence
<220> FEATURE:
<223> OTHER INFORMATION: Description of Artificial Sequence:synthetic
      target #6

<400> SEQUENCE: 14
ttccttggaa tcagagaag                                                19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:synthetic
      target #7

<400> SEQUENCE: 15
ttcctcggaa tcagagaag                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:synthetic
      target #8

<400> SEQUENCE: 16
ttcctgggaa tcagagaag                                                19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:-AgA- g/T
      target #10

<400> SEQUENCE: 17
tttaggtttt ttggattt                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:-AgA- g/A
      target #11

<400> SEQUENCE: 18
tttaggtttt atggattt                                                 18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:-AgA- g/G
      target #12

<400> SEQUENCE: 19
tttaggtttt gtggattt                                                 18

<210> SEQ ID NO 20
<211> LENGTH: 18
<212> TYPE: DNA
```

<213> ORGANISM: Artificial Sequence
<220> FEATURE:
<223> OTHER INFORMATION: Description of Artificial Sequence:-AgA- g/C
      target #13

<400> SEQUENCE: 20
tttaggtttt ctggattt                                                 18

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence:synthetic
      -AgA- probe #14
<220> FEATURE:
<221> NAME/KEY: modified_base
<222> LOCATION: (1)..(12)
<223> OTHER INFORMATION: phosphoramidite replaces phosphodiester
      linkages
<220> FEATURE:
<221> NAME/KEY: modified_base
<222> LOCATION: (5)
<223> OTHER INFORMATION: n = promiscuous (indiscriminative) base
      6-amino-1H-pyrazolo[3,4-d]pyrimidin-4(5H)-one
      (ppG, PPG, Super G or compound 49) nucleotide

<400> SEQUENCE: 21
tccanaaaac ct                                                       12

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:-AgA- g/T
      target #15

<400> SEQUENCE: 22
tttagtttcc tttgattt                                                 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:-AgA- g/A
      target #16

<400> SEQUENCE: 23
tttagtttcc tatgattt                                                 18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:-AgA- g/G
      target #17

<400> SEQUENCE: 24
tttagtttcc tgtgattt                                                 18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:-AgA- g/C target #18

<400> SEQUENCE: 25
tttagtttcc tctgattt                                                       18

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence:synthetic
      -AgA- probe #19
<220> FEATURE:
<221> NAME/KEY: modified_base
<222> LOCATION: (1)..(12)
<223> OTHER INFORMATION: phosphoramidite replaces phosphodiester
      linkages
<220> FEATURE:
<221> NAME/KEY: modified_base
<222> LOCATION: (4)
<223> OTHER INFORMATION: n = promiscuous (indiscriminative) base
      6-amino-1H-pyrazolo[3,4-d]pyrimidin-4(5H)-one
      (ppG, PPG, Super G or compound 49) nucleotide

<400> SEQUENCE: 26
tcanaggaaa ct                                                             12

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:-AgT- g/T
      target #20

<400> SEQUENCE: 27
tttaggatta ttggattt                                                       18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:-AgT- g/A
      target #21

<400> SEQUENCE: 28
tttaggatta atggattt                                                       18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:-AgT- g/G
      target #22

<400> SEQUENCE: 29
tttaggatta gtggattt                                                       18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:-AgT- g/C
      target #23

<400> SEQUENCE: 30

```
tttaggatta ctggattt                                              18

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence:synthetic
      -AgT- probe #24
<220> FEATURE:
<221> NAME/KEY: modified_base
<222> LOCATION: (1)..(12)
<223> OTHER INFORMATION: phosphoramidite replaces phosphodiester
      linkages
<220> FEATURE:
<221> NAME/KEY: modified_base
<222> LOCATION: (5)
<223> OTHER INFORMATION: n = promiscuous (indiscriminative) base
      6-amino-1H-pyrazolo[3,4-d]pyrimidin-4(5H)-one
      (ppG, PPG, Super G or compound 49) nucleotide

<400> SEQUENCE: 31
tccantaatc ct                                                    12

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:-AgG- g/T
      target #25

<400> SEQUENCE: 32
tttagacttc ttggattt                                              18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:-AgG- g/A
      target #26

<400> SEQUENCE: 33
tttagacttc atggattt                                              18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:-AgG- g/G
      target #27

<400> SEQUENCE: 34
tttagacttc gtggattt                                              18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:-AgG- g/C
      target #28

<400> SEQUENCE: 35
tttagacttc ctggattt                                              18
```

```
<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence:synthetic
      -AgG- probe #29
<220> FEATURE:
<221> NAME/KEY: modified_base
<222> LOCATION: (1)..(12)
<223> OTHER INFORMATION: phosphoramidite replaces phosphodiester
      linkages
<220> FEATURE:
<221> NAME/KEY: modified_base
<222> LOCATION: (5)
<223> OTHER INFORMATION: n = promiscuous (indiscriminative) base
      6-amino-1H-pyrazolo[3,4-d]pyrimidin-4(5H)-one
      (ppG, PPG, Super G or compound 49) nucleotide

<400> SEQUENCE: 36
tccangaagt ct                                                         12

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:-AgC- g/T
      target #30

<400> SEQUENCE: 37
tttagagttg ttcgattt                                                   18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:-AgC- g/A
      target #31

<400> SEQUENCE: 38
tttagagttg atcgattt                                                   18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:-AgC- g/G
      target #32

<400> SEQUENCE: 39
tttagagttg gtcgattt                                                   18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:-AgC- g/C
      target #33

<400> SEQUENCE: 40
tttagagttg ctcgattt                                                   18

<210> SEQ ID NO 41
<211> LENGTH: 12
```

```
<212> TYPE: DNA
<213> ORGANISM: Artificial Sequence
<220> FEATURE:
<223> OTHER INFORMATION: Description of Artificial Sequence:synthetic
      -AgC- probe #34
<220> FEATURE:
<221> NAME/KEY: modified_base
<222> LOCATION: (1)..(12)
<223> OTHER INFORMATION: phosphoramidite replaces phosphodiester
      linkages
<220> FEATURE:
<221> NAME/KEY: modified_base
<222> LOCATION: (5)
<223> OTHER INFORMATION: n = promiscuous (indiscriminative) base
      6-amino-1H-pyrazolo[3,4-d]pyrimidin-4(5H)-one
      (ppG, PPG, Super G or compound 49) nucleotide

<400> SEQUENCE: 41
tcgancaact ct                                                          12

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence:BARD1-03
      gene double SNP target

<400> SEQUENCE: 42
gcacrtggat atagt                                                       15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence:synthetic
      BARD1-03 probe
<220> FEATURE:
<221> NAME/KEY: modified_base
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (11)
<223> OTHER INFORMATION: n = universal bases 6-methyl-2-isoquinoline-1-
      one (compound 41) nucleotide or
      8-methyl-2-isoquinoline-1-one (compound 42)
      nucleotide
<220> FEATURE:
<221> NAME/KEY: modified_base
<222> LOCATION: (15)
<223> OTHER INFORMATION: n = c linked to fluorophore

<400> SEQUENCE: 43
nctatatcca ngtgn                                                       15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence:synthetic
      BARD1-03 probe
<220> FEATURE:
<221> NAME/KEY: modified_base
```

```
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (11)
<223> OTHER INFORMATION: n = universal base 6-amino-2-(4-hydroxy-5-
      hydroxymethyl-tetrahydro-furan-2-yl)-2,5-dihydro-pyrazolo[3,4-d]
      pyramidin-4-one (compound 40) nucleotide or
      promiscuous (indiscriminative) base 4-(4,6-diamino-1H-
      pyrazolo[3,4-d]pyrimidin-3-yl)but-3-yn-1-ol nucleotide
<220> FEATURE:
<221> NAME/KEY: modified_base
<222> LOCATION: (15)
<223> OTHER INFORMATION: n = c linked to fluorescein (Fl-A)

<400> SEQUENCE: 44
nctatatcca ngtgn                                                  15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence:synthetic
      BARD1-03 probe
<220> FEATURE:
<221> NAME/KEY: modified_base
<222> LOCATION: (1)..(15)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (11)
<223> OTHER INFORMATION: n = universal base 6-amino-2-(4-hydroxy-5-
      hydroxymethyl-tetrahydro-furan-2-yl)-2,5-dihydro-pyrazolo[3,4-d]
      pyramidin-4-one (compound 40) nucleotide or
      promiscuous (indiscriminative) base 4-(4,6-diamino-1H-
      pyrazolo[3,4-d]pyrimidin-3-yl)but-3-yn-1-ol nucleotide
<220> FEATURE:
<221> NAME/KEY: modified_base
<222> LOCATION: (15)
<223> OTHER INFORMATION: n = c linked to tetrachlorofluorescein (Fl-B)

<400> SEQUENCE: 45
nctatatcca natgn                                                  15

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence:
      Mycobacterium chelonae and Mycobacterium abscessus single
      mismatch Target 1

<400> SEQUENCE: 46
tttctctcaa agacatc                                                17

<210> SEQ ID NO 47
<211> LENGTH: 17
```

-continued

```
<212> TYPE: DNA
<213> ORGANISM: Artificial Sequence
<220> FEATURE:
<223> OTHER INFORMATION: Description of Artificial Sequence:
      Mycobacterium chelonae and Mycobacterium abscessus single
      mismatch Target 2

<400> SEQUENCE: 47
tttctttcaa agacatc                                                    17

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence:
      Mycobacterium chelonae and Mycobacterium abscessus single
      mismatch Probe
<220> FEATURE:
<221> NAME/KEY: modified_base
<222> LOCATION: (1)..(17)
<223> OTHER INFORMATION: phosphoramidite replaces phosphodiester
      linkages
<220> FEATURE:
<221> NAME/KEY: modified_base
<222> LOCATION: (1)
<223> OTHER INFORMATION: n = a linked to substituted
      dihydrocyclopyrroloindole minor groove binder
      (MGB) and a quencher (Q)
<220> FEATURE:
<221> NAME/KEY: modified_base
<222> LOCATION: (5)
<223> OTHER INFORMATION: n = promiscuous (indiscriminative) bases
      6-amino-1H-pyrazolo[3,4-d]pyrimidin-4(5H)-one
      (ppG, PPG, Super G or compound 49) nucleotide or
      4-(4,6-diamino-1H-pyrazolo[3,4-d]pyrimidin-3-yl)
      butt-3-yn-1-ol nucleotide
<220> FEATURE:
<221> NAME/KEY: modified_base
<222> LOCATION: (17)
<223> OTHER INFORMATION: n = g linked to
      6-carboxy-4,7,2',7'-tetrachlorofluorescein (TET)

<400> SEQUENCE: 48
naagngagtt tctgtan                                                    17
```